United States Patent
Orimoto et al.

(10) Patent No.: US 10,721,929 B2
(45) Date of Patent: Jul. 28, 2020

(54) HETEROCYCLIC COMPOUND AND HARMFUL-ARTHROPOD-CONTROLLING AGENT CONTAINING SAME

(71) Applicant: Sumitomo Chemical Company, Limited, Tokyo (JP)

(72) Inventors: Kohei Orimoto, Takarazuka (JP); Masaru Shimomura, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/333,166

(22) PCT Filed: Sep. 15, 2017

(86) PCT No.: PCT/JP2017/033478
§ 371 (c)(1),
(2) Date: Mar. 13, 2019

(87) PCT Pub. No.: WO2018/052119
PCT Pub. Date: Mar. 22, 2018

(65) Prior Publication Data
US 2019/0223436 A1  Jul. 25, 2019

(30) Foreign Application Priority Data

Sep. 16, 2016 (JP) .............................. 2016-182085
Jan. 25, 2017 (JP) .............................. 2017-011705

(51) Int. Cl.
*C07D 487/04* (2006.01)
*A01N 43/40* (2006.01)
(Continued)

(52) U.S. Cl.
CPC ............. *A01N 43/40* (2013.01); *A01N 43/90* (2013.01); *C07D 409/04* (2013.01); *C07D 471/04* (2013.01); *C07D 487/04* (2013.01)

(58) Field of Classification Search
CPC .. C07D 409/04; C07D 471/04; C07D 487/04; A01N 43/40; A01N 43/90
See application file for complete search history.

(56) References Cited

U.S. PATENT DOCUMENTS

| 5,306,827 A | 4/1994 | Barnes et al. |
| 5,739,083 A | 4/1998 | Endo et al. |

FOREIGN PATENT DOCUMENTS

| JP | H05262726 A | 10/1993 |
| JP | H08193067 A | 7/1996 |

(Continued)

OTHER PUBLICATIONS

Int'l Search Report dated Dec. 5, 2017 in Int'l Application No. PCT/JP2017/033478.
(Continued)

*Primary Examiner* — Deepak R Rao
(74) *Attorney, Agent, or Firm* — Panitch Schwarze Belisario & Nadel LLP

(57) ABSTRACT

A compound represented by Formula (I) is provided.

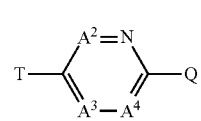

In Formula (I), Q represents a group represented by Formula Q1, Q2, or Q3, and T represents a chain hydrocarbon group, an alkoxyalkyl group, an alkylsulfanylalkyl group, an alkylsulfinylalkyl group, or an alkylsulfonylalkyl group, which has a halogen atom; a cycloalkylalkyl group or a cycloalkyl group, which has a substituent; $OR^1$, $S(O)_m R^1$, $OS(O)_2 R^1$, $CH_2 OR^1$, $NR^1 R^{29}$, $C(O)R^1$, $C(O)NR^1 R^{29}$, $NR^{29}C(O)R^1$, $N{=}CR^1 R^{30}$, or a group represented by any one of Formulas T-1 to T-12.

Q1

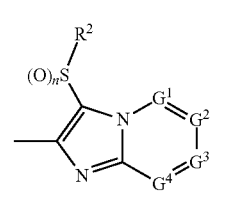

Q2

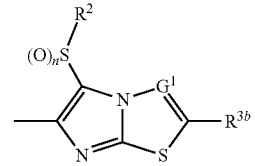

Q3

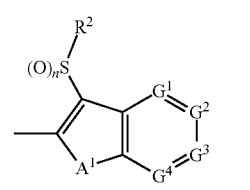

T-1

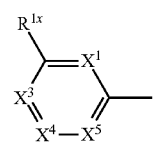

T-2

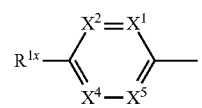

(Continued)

-continued

T-3

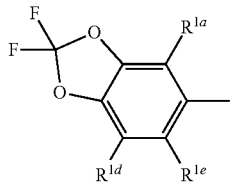

T-4

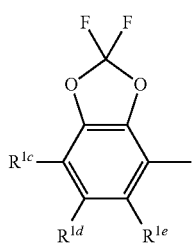

T-5

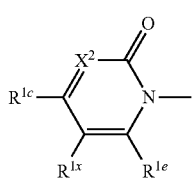

T-6

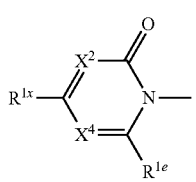

T-7

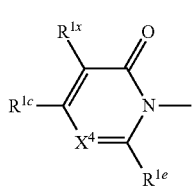

T-8

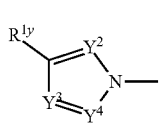

-continued

T-9

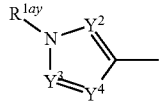

T-10

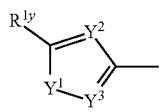

T-11

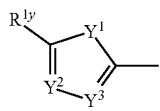

T-12

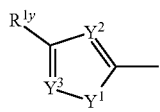

14 Claims, No Drawings

(51) Int. Cl.
  *A01N 43/90* (2006.01)
  *C07D 409/04* (2006.01)
  *C07D 471/04* (2006.01)

(56) References Cited

FOREIGN PATENT DOCUMENTS

| | | | |
|---|---|---|---|
| JP | H09165375 | A | 6/1997 |
| JP | H09506876 | A | 7/1997 |
| JP | 2015003906 | A | 1/2015 |
| JP | 2016528189 | A | 9/2016 |
| WO | 2010117932 | A1 | 10/2010 |
| WO | 2010117939 | A1 | 10/2010 |
| WO | 2015000715 | A | 1/2015 |
| WO | 2015087458 | A1 | 6/2015 |
| WO | 2015091945 | A1 | 6/2015 |
| WO | 2016142327 | A1 | 9/2016 |

OTHER PUBLICATIONS

Extended European Search Report dated Mar. 19, 2020 in EP Application No. 17851018.6.

HETEROCYCLIC COMPOUND AND HARMFUL-ARTHROPOD-CONTROLLING AGENT CONTAINING SAME

CROSS-REFERENCE TO RELATED APPLICATIONS

This application is a Section 371 of International Application No. PCT/JP2017/033478, filed Sep. 15, 2017, which was published in the Japanese language on Mar. 22, 2018 under International Publication No. WO 2018/052119 A1, which claims priority under 35 U.S.C. § 119(b) to Japanese Application No. 2016-182085, filed Sep. 16, 2016, and Japanese Application No. 2017-011705, filed Jan. 25, 2017, the disclosures of which are incorporated herein by reference.

TECHNICAL FIELD

The present invention relates to a heterocyclic compound and a harmful-arthropod-controlling agent using the same.

BACKGROUND ART

For the purpose of controlling harmful arthropods, various compounds have been examined so far and are being put to practical use.

In addition, it is known that certain compounds have a harmful organism-controlling effect (See, for example, PLT 1 and PTL 2).

CITATION LIST

Patent Documents

[PTL 1] PCT International Publication No. WO 2010/117932
[PTL 2] PCT International Publication No. WO 2010/117939

SUMMARY OF THE INVENTION

Problems to be Solved by the Invention

An Object of the present invention is to provide, a compound having excellent controlling efficacy on harmful arthropods.

Means to Solve the Problems

The present invention is as follows.
[1] A compound represented by Formula (I):

$$T-\underset{A^3-A^4}{\overset{A^2=N}{\diagup\diagdown}}-Q \qquad (I)$$

in the formula,
Q represents a group represented by Formula Q1, a group represented by Formula Q2, or a group represented by Formula Q3, n represents 0, 1, or 2,
$G^1$ represents a nitrogen atom or $CR^{3a}$,
$G^2$ represents a nitrogen atom or $CR^{3b}$,
$G^3$ represents a nitrogen atom or $CR^{3c}$,
$G^4$ represents a nitrogen atom or $CR^{3d}$,
$R^{3a}$, $R^{3b}$, $R^{3c}$, and $R^{3d}$ each independently represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a 5- or 6-membered aromatic heterocyclic group optionally having one or more substituents selected from Group H, $OR^{12x}$, $NR^{11}R^{12}$, $NR^{11a}R^{12a}$, $NR^{29}NR^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15x}R^{16x}$, $NR^{24}NR^{11}C(O)NR^{15x}R^{16x}$, $N\!=\!CHNR^{15x}R^{16x}$, $N\!=\!S(O)_xR^{15}R^{16}$, $C(O)OR^{17}$, $C(O)R^{13}$, $C(O)NR^{15x}R^{16x}$, $C(O)NR^{11}S(O)_2R^{23}$, $CR^{30}\!=\!NOR^{17}$, $NR^{11}CR^{24}\!=\!NOR^{17}$, a cyano group, a nitro group, a hydrogen atom, or a halogen atom,
x represents 0 or 1,
$A^1$ represents $NR^5$, an oxygen atom, or a sulfur atom,
$A^2$ represents a nitrogen, atom or $CR^{4a}$,
$A^3$ represents a nitrogen atom or $CR^{4b}$,
$A^4$ represents a nitrogen atom or $CR^{4c}$,
$R^{4a}$, $R^{4b}$, and $R^{4c}$ each independently represents a hydrogen, atom, a C1-C6 chain hydrocarbon group optionally, having one or more halogen atoms, a nitro group, $OR^{18}$, $NR^{18}R^{19}$, a cyano group, or a halogen atom,
T represents a C1-C10 chain hydrocarbon group having one or more halogen atoms, a (C1-C5 alloy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N\!=\!CR^1R^{30}$, a group represented by Formula T-1, a group represented by Formula T-2, a group represented by Formula T-3, a group represented by Formula T-4, a group represented by Formula T-5, a group represented by Formula T-6, a group represented by Formula T-7, a group represented by Formula T-8, a group represented by Formula T-9, a group represented by Formula T-10, a group represented by Formula T-11, or a group represented by Formula T-12.

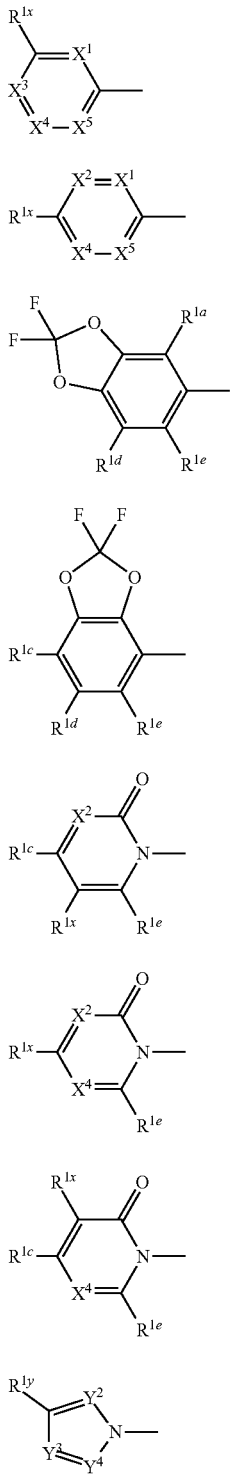

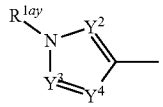

T-9

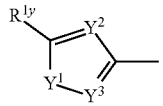

T-10

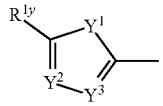

T-11

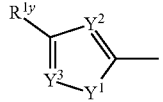

T-12

$X^1$ represents a nitrogen atom or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{1e}$,
$R^{1x}$ represents $OR^7$, $OS(O)_2R^7$, $S(O)_mR^7$, $NR^1R^{29}$, $NR^8S(O)_2R^7$, a C1-C5 chain hydrocarbon group having one or more halogen atoms, or a halogen atom,
$R^{1a}$, $R^{1b}$, $R^{1c}$, $R^{1d}$ and $R^{1e}$ each independently represents a hydrogen atom, a C1-C6 chain hydrocarbon group optionally having one or more halogen atoms, a C3-C6 cycloalkyl group optionally having one or more halogen atoms, or a halogen atom,
$Y^1$ represents $NR^{25}$, an oxygen atom, or a sulfur atom,
$Y^2$ represents a nitrogen atom or $CR^{26}$,
$Y^3$ represents a nitrogen atom or $CR^{27}$,
$Y^4$ represents a nitrogen atom or $CR^{28}$,
$R^5$ and $R^{25}$ each independently represents a hydrogen atom, a C1-C6 chain hydrocarbon group optionally having one or more halogen atoms, a C1-C6, alkoxy group optionally having one or more halogen atoms, a C3-C7 cycloalkyl group optionally having one or more halogen atoms, or a (C3-C7 cycloalkyl) C1-C6 alkyl group optionally having one or more halogen atoms,
$R^{26}$, $R^{27}$, and $R^{28}$ each independently represents a hydrogen atom, a C1-C6 chain hydrocarbon group optionally having one or more halogen atoms, a C3-C6 cycloalkyl group optionally having one or more halogen atoms, or a halogen-atom,
$R^{1y}$ represents $OR^7$, $OS(O)_2R^7$, $S(O)_mR^7$, $NR^8S(O)_2R^7$, cyano group, a C1-C5 chain hydrocarbon group having ones or more halogen atoms, or a halogen atom,
$R^{1ay}$ and $R^7$ each independently represents a C1-C6 chain hydrocarbon group having one or more halogen atoms,
$R^8$ represents a hydrogen atom, or a C1-C6 chain hydrocarbon group optionally having one or more halogen atoms,
m represents 0, 1, or 2,
$R^1$ represents a C1-C10 chain hydrocarbon group having one or more halogen atoms, a (C1-C5 alkoxy) C2-C5 alkyl group having one or more halogen atoms, (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl)-C1-C3 alkyl group having one or more substituents selected from Group G, or a C3-C7 cycloalkyl group having one or more substituents selected from Group G, $R^2$ represents a cyclopropyl group, a cyclopropylmethyl group, or a C1-C6 group optionally having one or more halogen-atoms, $R^{11}$, $R^{17}$, $R^{19}$, $R^{24}$, and $R^{29}$ each independently represents a hydrogen atom, or a C1-C6 chain hydrocarbon group optionally having-one or more halogen atoms, $R^{30}$ represents a hydrogen atom, a halogen atom, $OR^{31}$, $NR^{32}R^{33}$, or a C1-C6 chain hydrocarbon group optionally having one or more halogen atoms, $R^{18}$ and $R^{31}$ each independently represents a C1-C6 chain hydrocarbon group optionally having one or more halogen atoms, $R^{32}$ and $R^{33}$ each independently represents a hydrogen atom, or a C1-C6 chain hydrocarbon group optionally having one or more halogen atoms, $R^{12}$ represents a hydrogen atom, $S(O)_2R^{23}$, a C1-C6 chain hydrocarbon group optionally having one or more halogen atoms, or a C1-C6 alkyl group having one substituent selected from group F, $R^{12x}$ represents a C1-C6 chain hydrocarbon group optionally having one or more halogen atoms, a C1-C6 alkyl group having one substituent selected, from Group F, a C3-C7 cycloalkyl group optionally having, one or more substituents selected from Group J, a C3-C7 cycloalkenyl group optionally having one or more substituents selected from Group J, a phenyl group, a 6-membered aromatic heterocyclic group, in which the phenyl group and the 6-Membered aromatic heterocyclic group each independently optionally has one or more substituents selected from Group D, $S(O)_2R^{23}$, or a hydrogen atom, $R^{23}$ represents a C1-C6 chain hydrocarbon groups optionally having one or more halogen atoms, or a phenyl group optionally having one or more substituents selected from Group D, $R^{11a}$ and $R^{12a}$, together with the nitrogen atom which $R^{11a}$ and $R^{12a}$ are bonded, represent a 3- to 7-membered non-aromatic heterocyclic group, optionally having one more substituents selected from Group E, $R^{13}$ represents a hydrogen-atom, a C1-C6 chain hydrocarbon group optionally having one or more halogen, atoms, a C3-C7 cycloalkyl group optionally having one or more halogen atoms, a (C3-C6 cycloalkyl) C1-C3 alkyl group optionally having one or more halogen atoms, a phenyl group optionally having one or more substituents selected from Group D, or a 5- or 6-membered aromatic heterocyclic group optionally having one or more substituents selected from Group D.

$R^{14}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl C1-C3 alkyl group, in which the phenyl moiety in the phenyl C1-C3 alkyl group optionally has one or more substituents selected from Group D, $R^{15}$ and $R^{16}$ each independently represents a C1-C6 alkyl group optionally having one or more halogen atoms, $R^{15x}$ represents, a C1-C6 alkyl group optionally having one or more halogen atoms, or a hydrogen atom, $R^{16x}$ represents a C1-C6 chain hydrocarbon group optionally having one or more substituents selected from Group F, a C3-C7 cycloalkyl group optionally having one or more substituents selected from Group. J, or a hydrogen atom, Group B: a group consisting or a C1-C6 alkoxy group-optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more atoms, a C1-C6 alkylsulfinyl group optionally having one or more halogen atoms, a C1-C6 alkylsulfonyl group optionally having one or more, halogen atoms, a C3-C6 cycloalkyl group optionally having one or more halogen atoms, a cyano group, a hydroxy group, and a halogen, atom, Group C: a group consisting of a C1-C6 chain hydrocarbon group optionally having one or more halogen atoms, a C1-C6 alkoxy group optionally having one or more halogen atoms, a C3-C6 alkenyloxy group, optionally having one or more halogen atoms, a C3-C6 alkynyloxy group optionally having one or more halogenatoms, and halogen atom, Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, in which $R^{21}$ and $R^{22}$ each independently represents C1-C6 alkyl group optionally having, one or more, halogen atoms, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group, Group F: a group consisting of a C1-C6 alkoxy group optionally having one or more halogen atoms, an amino group, $NHR^{21}$, $NR^{21}R^{22}$, a cyano group, a phenyl group optionally having one or more substituents selected from Group D, a 5- or 6-membered aromatic heterocyclic group optionally having one or more substituents selected from Group D, a C3-C7 cycloalkyl group optionally having one or more halogen atoms, and a 3- to 7-membered non-aromatic heterocyclic group optionally having one or more substituents selected from Group C, Group G: a group consisting of a halogen atom and a C1 haloalkyl group, Group H: a group consisting of a halogen atom, a nitro group, a cyano group, an amino group, a 5- or 6-membered aromatic heterocyclic group, a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, and $C(O)OR^{10}$, Group J: a group consisting of C1-C6 alkyl group optionally having one or more halogen atoms, a halogen atom, and a cyano group, $R^9$ represents a C1-C6 all group optionally having one or more halogen atoms, or a C3-C6 cycloalkyl group optionally having one or more halogen atoms, and $R^{10}$ represents a hydrogen atom, a C1-C6 alkyl group optionally having one or more halogen atoms, or a C3-C6 cycloalkyl group optionally having one or more halogen atoms.

[2] The compound according to [1], which is represented by Formula (1):

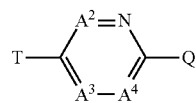  (I)

in the formula,

Q is a group represented by Formula Q1, a group represented by Formula Q2, or a group represented by Formula Q3,

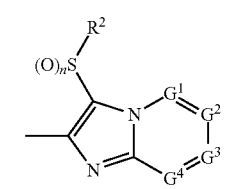  Q1

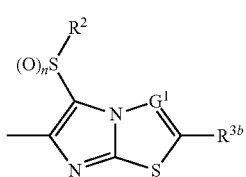  Q2

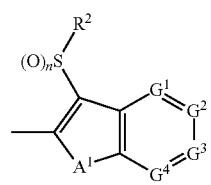  Q3 n is 0, 1, or 2, $G^1$ is a nitrogen atom or $CR^{3a}$,
$G^2$ is a nitrogen atom or $CR^{3b}$,
$G^3$ is a nitrogen atom or $CR^{3c}$,
$G^4$ is a nitrogen atom, or $CR^{3d}$,
$R^{3a}$, $R^{3b}$, $R^{3c}$, and $R^{3d}$ are each independently a $C_1$-$C_6$ chain hydrocarbon group optionally having one or more substituents selected from Group B, a C3-C7 cycloalkyl group optionally having one or more substituents selected from Group 8, a phenyl group optionally having one or more substituents selected from Group H, a 5- or 6-membered aromatic heterocyclic group optionally having one or more substituents selected front Group H, $OR^{12}$, $NR^{11}R^{12}$, $NR^{11a}R^{12a}$, $NR^{29}NR^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15x}R^{16x}$, $NR^{24}NR^{11}C(O)NR^{15}R^{16}$, $N{=}CHNR^{15}R^{16}$, $N{=}S(O)_xR^{15}R^{16}$, $C(O)OR^{17}$, a cyano group, a nitro group, a hydrogen atom, or a halogen atom, x is 0 or 1, $A^1$ is $NR^5$, an oxygen atom, or a sulfur atom,
$A^2$ is a nitrogen atom or $CR^{4a}$,
$A^3$ is a nitrogen atom or $CR^{4b}$,
$A^4$ is a nitrogen atom or $CR^{4c}$,
$R^{4a}$, $R^{4b}$, and $R^{4c}$ are each independently a hydrogen atom, a C1-C6 chain hydrocarbon group optionally having one or more halogen atoms, a nitro group, $OR^{18}$, $NR^{18}R^{19}$, a cyano group, or a halogen atom, T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 allylsulfonyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents-selected from Group G, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N{=}CR^1R^{30}$, a group represented by Formula T-1, a group represented by Formula T-2, a group represented by Formula T-3, a group represented by Formula T-4, a group represented by Formula T-5, a group represented by Formula T-6, a group represented by Formula T-7, a group represented by Formula T-8, a group represented by Formula T-9, a group represented by Formula T-10, a group represented by Formula T-11, or a group represented by Formula T-12,

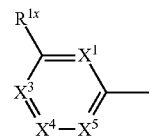  T-1

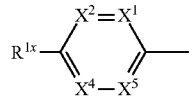  T-2

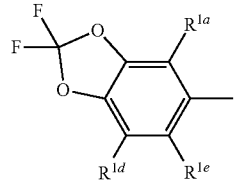  T-3

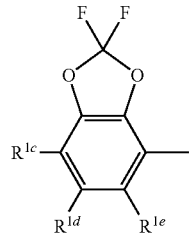  T-4

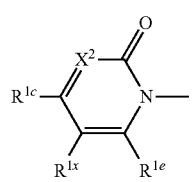  T-5

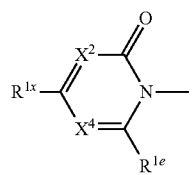  T-6

-continued

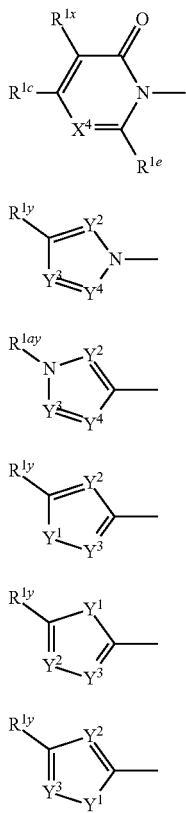

T-7

T-8

T-9

T-10

T-11

T-12

$X^1$ is a nitrogen atom or $CR^{1a}$,
$X^2$ is a nitrogen atom or $CR^{1b}$,
$X^3$ is a nitrogen atom or $CR^{1c}$,
$X^4$ is a nitrogen atom or $CR^{1d}$,
$X^5$ is a nitrogen atom or $CR^{1e}$,
$R^{1x}$ is $OR^7$, $OS(O)_2R^7$, $S(O)_mR^7$, $NR^1R^{29}$, $NR^8S(O)_2R^7$, a C1-C5 chain hydrocarbon group having one or more halogen atoms, or a halogen atom,
$R^{1a}$, $R^{1b}$, $R^{1c}$, $R^{1d}$, and $R^{1e}$ are each independently a hydrogen atom, a C1-C6 chain hydrocarbon group optionally having one or more halogen atoms, a C3-C6 cycloalkyl group optionally having one or more halogen atoms, or a halogen atom,
$Y^1$ is $NR^{25}$, an oxygen atom, or a sulfur atom,
$Y^2$ is a nitrogen atom or $CR^{26}$,
$Y^3$ is a nitrogen atom or $CR^{27}$,
$Y^4$ is a nitrogen atom or $CR^{28}$,
$R^5$ and $R^{25}$ are each independently a hydrogen atom, a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl) C1-C6 group optionally having one or more halogen atoms,
$R^{26}$, $R^{27}$, and $R^{28}$ are each independently a hydrogen atom, a C1-C6 chain hydrocarbon group optionally having one or more halogen atoms, a C3-C6 cycloalkyl group optionally having one or more halogen atoms, or a halogen atom,
$R^{1ay}$ is $OR^7$, $OS(O)_2R^7$, $S(O)_mR^7$, $NR^8S(O)_2R^7$, a cyano group, a C1-C5 chain hydrocarbon group having one or more halogen atoms, or halogen atom,
$R^{1ay}$ and $R^7$ are each, independently a C1-C6 chain hydrocarbon group having one or more halogen atoms,
$R^8$ is a hydrogen atom, or a C1-C6 chain hydrocarbon group optionally having one or more halogen atoms,
m is 0, 1, or 2,
$R^1$ is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfanyl) C2-C5 alkyl group having one or more halogen atoms, a (C1-C5 alkylsulfonyl) C2-C5 alkyl group having one or more halogen, atoms, a (C3-C7 cycloalkyl) C1-C3 alkyl group having one or more substituents selected from Group G. or a C3-C7 cycloalkyl group having one or more substituents selected from Group G,
$R^2$ is a cyclopropyl group, a cyclopropylmethyl group, or a C1-C6 alkyl group optionally having one or more halogen atoms,
$R^{11}$, $R^{17}$, $R^{19}$, $R^{24}$, and $R^{29}$ are each independently a hydrogen atom, or a C1-C6 chain hydrocarbon group optionally having one or more halogen atoms,
$R^{30}$ is a hydrogen atom, a halogen atom, $OR^{31}$, $NR^{32}R^{33}$ or a C1-C6 chain hydrocarbon group optionally having one or more halogen atoms,
$R^{18}$ and $R^{31}$ are each independently a C1-C6 chain hydrocarbon group optionally having one or more halogen atoms,
$R^{32}$ and $R^{33}$ are each independently a hydrogen atom or a C1-C6 chain hydrocarbon group optionally having one or more halogen atoms,
$R^{12}$ is a hydrogen, atom, $S(O)_2R^{23}$, a C1-C6 chain hydrocarbon group optionally having one or more halogen atoms, or a C1-C6 alkyl group having one substituent selected from Group F,
$R^{23}$ is a C1-C6 chain hydrocarbon group optionally having one or more halogen atoms, or a phenyl group optionally having one or more substituents selected from Group D,
$R^{11a}$ and $R^{12a}$, together with the nitrogen atom to which $R^{11a}$ and $R^{12a}$ are bonded, are a 3- to 7-membered non-aromatic heterocyclic group optionally having one or more substituents selected from Group E,
$R^{13}$ is a hydrogen atom, a C1-C6 chain hydrocarbon group optionally having one or more halogen, atoms, a C3-C7 cycloalkyl group optionally having one or more halogen atoms, a (C3-C6 cycloalkyl) C1-C3 alkyl-group optionally having one or more halogen atoms, a phenyl group optionally having one or more substituents selected from Group D, or a 5- or 6-membered aromatic heterocyclic group optionally having one or more substituents selected from Group D,
$R^{14}$ is a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one halogen atoms, or a phenyl C1-C3 alkyl group, in which the phenyl moiety in, the phenyl C1-C3 alkyl group optionally has one or more substituents selected from Group D,
$R^{15}$ and $R^{16}$ each independently represents a C1-C6 alkyl group optionally having one or more halogen atoms.
Group B: a group consisting of a C1-C6 alkoxy group-optionally having one or more halogen atoms, a C3-C6 alkenyloxy group optionally having one or more halogen atoms, a C3-C6 alkynyloxy group, optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, Group C: a group consisting of a C1-C6, chain hydrocarbon group optionally having one or more halogen atoms, a C1-C6 alkoxy group optionally having one or more halogen atoms, a C3-C6 alkenyloxy group optionally having one or more halogen-atoms, a C3-C6 alkynyloxy group optionally having-one or more halogen-atoms, and a halogen atom, Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more-halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, in which $R^{21}$ and $R^{22}$ each independently represents a C1-C6 alkyl group optionally having one or more halogen atoms, Group E: a group consisting of a C1-C6 chain hydrocarbon group optionally having one or more halogen atoms a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom an oxo group, a hydroxy group, a cyano group, and a nitro group, Group F: a group consisting of a C1-C6 alkoxy group optionally having one or more halogen atoms, an amino group $NHR^{21}$, $NR^{21}R^{22}$, cyano group, a phenyl group optionally having one or more substituents selected from Group D, a 5- or 6-membered aromatic heterocyclic group optionally having one or more substituents selected from Group D, a C3-C7 cycloalkyl group optionally having one or more halogen atoms, and a 3- to 7-membered non-aromatic heterocyclic group optionally having one or more substituents selected from Group C, Group G: a group consisting of a halogen atom and a C1-C6 haloalkyl group, Group H: a group consisting of a halogen atom a nitro group, a cyano group, an amino group, a 5- or 6-membered aromatic heterocyclic group, a C1-C6 alkyl group optionally having one or more halogen atoms, $OR^{10}$, $NR^9R^{10}$, $C(O)R^{10}$, $C(O)NR^9R^{10}$ $OC(O)R^9$, $OC(O)OR^9$, $NR^{10}C(O)R^9$, $NR^{10}C(O)OR^9$, and $C(O)OR^{10}$, $R^9$ is a C1-C6 alkyl group optionally having one or more halogen atoms, or a C3-C6 cycloalkyl group optionally having one or more halogen atoms, and $R^{10}$ represents a hydrogen atom, a C1-C6 alkyl group optionally having one or more halogen atoms, or a C3-C6 cycloalkyl group optionally having one or more halogen atoms.

[3] The compound according to [1] or [2],
wherein Q is a group represented by Formula Q1.

[4] The compound according to any one of [1] to [3], wherein $A^2$ is $CR^{4a}$ and $A^4$ is $CR^{4c}$,

[5] The compound according to any one of [1] to [3], wherein $A^2$ is $CR^{4a}$, $A^3$ is $CR^{4b}$, and $A^4$ is $CR^{4c}$.

[6] The compound according to any one of [1] to [3], wherein $A^2$ is $CR^{4a}$, $A^3$ is a nitrogen atom, and $A^4$ is $CR^{4c}$.

[7] The compound, according to any one of [1] to [6], wherein T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl)C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$. $S(O)_mR^1$, $OS(O)_2R^1$, or $NR^1R^{29}$.

[8] The compound according to anyone of [1] to [6],
wherein T is $OR^1$, and $R^1$ is a C1-C5 alkyl group having three or more fluorine atoms.

[9] The compound according to any one of [1] to [8],
wherein $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H, an amino group, $NR^{11}C(O)OR^{14}$, a hydrogen atom, or a halogen atom, and $R^{4a}$ and $R^{4c}$ are hydrogen atoms.

[10] The compound according to any one of [1] to [8],
wherein $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogenatoms, or a hydrogen atom, and $R^{4a}$ and $R^{4c}$ are hydrogen atoms.

[11] The compound according to any one of [1] to [10], wherein $R^2$ is an ethyl group.

[12] A harmful-arthropod-controlling composition containing:
the compound according to any one of [1] to [11]; and
an inactive carrier.

[13] A method for controlling a harmful arthropod, including:
applying an effective amount of the compound according to any one of [1] to [11] to the harmful arthropod or a habitat of the harmful arthropod.

[14] A composition containing:
one or more ingredients selected from the group consisting of Group (a), Group (b), Group (c), and Group (d); and
the compound according to anyone of [1] to [11],
Group (a): a group consisting of insecticidal active ingredients, acaricidal active ingredients, and nematicidal active ingredients,
Group (b): fungicidal active ingredients,
Group (c): plant growth-regulating ingredients, and
Group (d): phytotoxicity-decreasing ingredients.

Effects of the Invention

According to the present invention, it is possible to control a harmful arthropod.

EMBODIMENTS FOR CARRYING OUT THE INVENTION

A substituent in the present invention will be described.
The term "halogen atom" refers to a fluorine atom, a chlorine atom, a bromine atom, or an iodine atom.
The phrase "optionally having a substituent" means having or not having a substituent. In a case of having two or more substituents, such substituents may be the same or different from each other.
The phrase "optionally having a halogen atom" means having or not-having a halogen atom. In a case of having two or more halogen atoms such halogen atoms may be the same or different from each other.

In a case of "having one or more substituents", an upper limit of the number of the substituents can be determined by the number of chemically substitutable hydrogen atoms.

In a case of "having one or more halogen atoms", an upper limit of the number of the halogen atoms can be determined by the number of chemically substitutable hydrogen atoms.

The indication "CX-CY" in the present specification means that the number of carbon atoms is X to Y. For example, the indication "C1-C4" means that the number of carbon atoms is 1 to 4.

The term "chain hydrocarbon group" refers to an alkyl group, an alkenyl group, or an alkynyl group. A case where the "chain hydrocarbon group" is an alkenyl group or an alkynyl group means that the number of carbon atoms is two or more.

As the "alkyl group", for example, a methyl group, an ethyl group, a propyl group, an isopropyl group, a 1,1-dimethylpropyl group, a 1,2-dimethylpropyl group, a 1-ethylpropyl group, a butyl group, a secbutyl group a tert-butyl group, a pentyl group, a hexyl group, and an octyl group can be mentioned, and exemplification is made depending on the above-mentioned range of the number of carbon atoms.

As the "alkenyl group", for example, a vinyl group, a 1-propenyl group, a 2-propenyl group, a 1-methyl-1-propenyl group, a 1-methyl-2-propenyl group, a 1,2-dimethyl-1-propenyl group, 1-ethyl-2-propenyl group, a 3-butenyl group, a 4-pentenyl group, a 5-hexenyl group, and a 7-octenyl group can be mentioned, and exemplification is made depending on the above-mentioned range of the number of carbon atoms.

As the "alkynyl group", for example, an ethynyl group, a 1-propynyl group, a 2-propynyl group, a 1-methyl-2-propynyl group, a 1,1-dimethyl-2-propynyl group, a 1-ethyl-2-propynyl group, a 2-butynyl group, a 4-pentynyl group, a 5-hexynyl group, and a 7-octynyl group can be mentioned, and exemplification is made depending on the above-mentioned range of the number of carbon atoms.

Accordingly, for example, the term "C1-C1.0 chain hydrocarbon group having one or more halogen atoms" refers to a C1-C10 alkyl group having one or more halogen atoms, a C2-C10 alkenyl group having one or more halogen atoms, or a C2-C10 alkynyl group having one or more halogen atoms. Among these, a C1-C10 alkyl group having one or more halogen atoms is preferable.

As the "C1-C10 alkyl group having one or more halogen atoms", for example, a difluoromethyl group, a trifluoromethyl group, a 2,2,2-trifluoroethyl group, a 2-bromo-1,1,2,2-tetrafluoroethyl group, a perfluoroethyl group, a 2,2,3,3-tetrafluoropropyl group, a 2,2,3,4,4-hexafluorobutyl group, 2,2,3,3,4,4,4-heptafluorobutyl group, a 1-methyl-2,2,3,3-tetrafluoropropyl group, a 2,2,3,3,3-pentafluoropropyl group, a perfluoropropyl group, a perfluorobutyl group, a perfluoropentyl group, and a perfluorohexyl group can be mentioned.

As the "C1-C6 haloalkyl group"; for example, a trifluoromethyl group, a 2,2,2-trifluoroethyl group, a 2-bromo-1,1,2,2-tetrafluoroethyl group, a 2,2,3,3-tetrafluoropropyl group, a 1-methyl-2,2,3,3-tetrafluoropropyl group, and a perfluorohexyl group can be mentioned.

As the "cycloalkyl group", for example, a cyclopropyl group, a cyclobutyl group, a cyclopentyl group, a cyclohexyl group, and a cycloheptyl group can be mentioned, and exemplification is, made depending on the above-mentioned range of the number of carbon atoms.

As the "cycloalkenyl group", for example, a 1-cyclopropenylgroup, a 2-cyclopropenyl group, a 1-cyclobutenyl group, a 2-cyclobutenyl group, a 1-cyclopentenyl group, a 2-cyclopentenyl group, a 3-cyclopentenyl group, a 1-cyclohexenyl group, a 2-cyclohexenyl group, a 3-cyclohexenyl group, a 1-cycloheptenyl group, a 2-cycloheptenyl group, a 3-cycloheptenyl group, and a 4-cycloheptenyl group can be mentioned, and exemplification is made depending on, the above-mentioned range of the number of carbon atoms.

The term "alkoxy group" refers to an alkoxy group having the alkyl group, and, for example, a methoxy group, an ethoxy-group, a propoxy group, an isopropoxy group, a 1,1-dimethylpropoxy group, a 1,2-dimethylpropoxy group, a 1-ethylpropoxy group, a butoxy group, a sec-butoxy group, and a tert-butoxy group can be mentioned.

The term "alkylsultfanyl group" refers to an alkylsulfanyl group having the alkyl group, and, for example, a methylsulfanyl group, an ethylsulfanyl group, a propylsulfanyl group, an isopropylsulfanyl group, a 1,1-dimethylpropylsulfanyl group, a 1,2-dimethylpropylsulfanyl group, a 1-ethylpropylsulfanyl group, and a butylsulfanyl group can be mentioned.

The term "alkylsulfinyl group" refers to an alkylsulfinyl group having the alkyl group, and, for example, a methylsulfinyl group, an ethylsulfinyl group, a propylsulfinyl group, an isopropylsulfinyl group, a 1,1-dimethylpropylsulfinyl group, a 1,2-dimethylpropylsulfinyl group, a 1-ethylpropylsulfinyl group, and a butylsulfinyl group can be mentioned.

The term "alkylsulfonyl group" refers to an alkylsulfonyl group having the alkyl group, and, for example, a methylsulfonyl group, an ethylsulfonyl group, a propylsulfonyl group, an isopropylsulfonyl group, a 1,1-dimethylpropylsulfonyl group, a 1,2-dimethylpropylsulfonyl group, a 1-ethylpropylsulfonyl group, and a butylsulfonyl group can be mentioned.

The term "3- to 7-membered non-aromatic heterocyclic group" refers to a group that contains an aziridine ring, an azetidine ring, a pyrrolidine ring, an imidazoline ring, an imidazolidine ring, a dihydropyridine ring, a tetrahydropyridine ring, a piperidine ring, a tetrahydropyrimidine ring, a hexahydropyriinidine ring, a piperazine ring, an azepane ring, an oxazolidine ring, an isoxazoiidinering, a 1,3-oxizinane ring, a morpholiite ring, a 1,4-oxazepane ring, a thiazolidine ring, an isothiazolidine ring, a 1,3-thiazinane ring, a thiomorpholine ring, or a 1,4-thiazepane ring. As a 3- to 7-membered non-aromatic heterocyclic group optionally having one or more substituents selected from Group E, for example, the following groups can be mentioned.

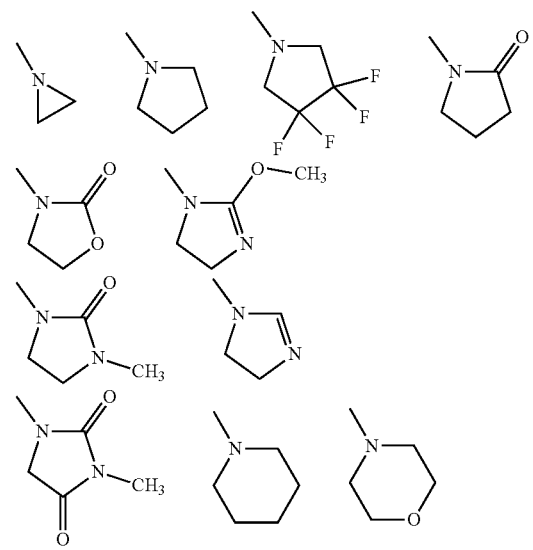

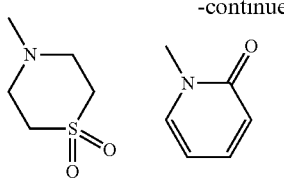

The term "(C1-C5 alkoxy) C2-C5 alkyl group having one or more halogen atoms" refers to a group in which (C1-C alkoxy) and/or (C2-C5 alkyl) has one or more halogen atoms, and, for example, a 2-(trifluoromethoxy) ethyl group, 2,2-difluoro-3-methoxypropyl, a 2,2-difluoro-3-(2,2,2-trifluoroethoxy) propyl group, and a 3-(2-chloroethoxy) propyl group can be mentioned.

The term "(C1-C5 alkylsulfanyl) C2-C5 alkyl group having one or more halogen atoms" refers to a group in which (C1-C5 alkylsulfanyl) and/or (C2-C5 alkyl) has one or more halogen atoms, and, for example, a 2,2-difluoro-2-(trifluoromethylthio) ethyl group can be mentioned.

The term "(C1-C5 alkylsulfinyl) C2-C5 alkyl group having one or more halogen atoms" refers to a group in which (C1-C5 alkylsulfinyl) and/or (C2-C5 alkyl) has one or more halogen atoms, and, for example, a 2,2-difluoro-2-(trifluoromethanesulfinyl) ethyl group can be mentioned.

The term "(C1-C5 alkylsulfonyl) C2-C5 alkyl group having one or more halogen atoms" refers to a group in which (C1-C5 alkylsulfonyl) and/or (C2-C5 alkyl) has one or more halogen atoms, and, for example, a 2,2-difluoro-2-(trifluoromethanesulfonyl) ethyl group can be mentioned.

The term "(C3-C6 cycloalkyl) C1-C3 alkyl group optionally having one or more halogen atoms" refers to a group in which (C3-C6 cycloalkyl) and/or (C1-C3 alkyl) optionally has one or more halogen atoms, and, for example, a (2,2-difluorocyclopropyl) methyl group, a 2-cyclopropyl-1,1,2,2-tetrafluoroethyl group, and a 2-(2,2-difluorocyclopropyl)-1,1,2,2-tetrafluoroethyl group can be mentioned.

The term "(C3-C7 cycloalkyl) C1-C6 alkyl group optionally having one or more halogen atoms" refers to a group in which (C3-C7 cycloalkyl) and/or (C1-C6 alkyl) optionally has one or more halogen atoms, and, for example, a (2,2-difluorocyclopropyl) methyl group, a 2-cyclopropyl-1,1,2,2-tetrafluoroethyl group, a 2-(2,2-difluorocyclopropyl)-1,1,2,2-tetrafluoroethyl group, and a 2-(2,2-difluorocyclopropyl)-1,1,2,2-tetrafluoropropyl group.

The term "(C3-C7 cycloalkyl) C1-C3 alkyl group having one or more substituents selected from Group G" refers to a group in which (C3-C7 cycloalkyl) and/or (C1-C3 alkyl) has one or more substituents selected from one or more Group G, and, for example, a (2,2-difluorocyclopropyl)-methyl group, a [1-(trifluoromethiyl)cyclopropyil]methyl group, a [2-(trifluotomethyl)cyclopropyl]methyl group, a 2-cylopropyl-1,1,2,2-tetrafluoroethyl group, a 2-cyclopropyl-3,3,3-trifluoropropyl group, and a 1,1,2,2-tetrafluoro-2-[2-(trifluoromethyl)cyclopropyl]ethyl group can be mentioned.

As the "C3-C7 cycloalkyl group having one or more substituents selected from Group G", for example, a 2,2-difluorocyclopropyl group, a 1-(2,2,2-trifluoroethyl)cyclopropyl group, and a 4-(trifluoromethyl)cyclohexyl group can be mentioned.

As the "phenyl C1-C3 alkyl group, in which the phenyl moiety in the phenyl C1-C3 alkyl group optionally has one or more substituents selected from Group D", for example, a benzyl group, a 2-fluorobenzyl group, a 4-chlorobenzyl group, a 4-(trifluoromethyl)benzyl group, and a 2-[4-(trifluoromethyl)phenyl]ethyl group can be mentioned, The term "5- or 6-membered aromatic heterocyclic group" refers to a 5-membered aromatic heterocyclic group or a 6-membered aromatic heterocyclic group. The 5-membered aromatic heterocyclic group refers to a pyrrolyl group, a furyl group, a thenyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. As the 5-membered aromatic heterocyclic group, a 5-membered aromatic heterocyclic group having 1 to 4 nitrogen atoms, that is a pyrrolyl group, a pyrazolyl group, an imidazolyl group, a 1,2,4-triazolyl group, a 1,2,3-triazolyl group, or a tetrazolyl group is preferable. The 6-membered aromatic heterocyclic group refers to a pyridyl group, a pyridazinyl group, a pyrimidinyl group, or a pyrazinyl group, In the present specification, in a case of a group described by a chemical formula in the text, in principle, an atom at the leftmost side has a bonding hand, and a valence thereof is determined depending on an atom to be bonded. Therefore, for example, a group represented by $OR^{12}$ refers to a monovalent group in which the oxygen atom at the leftmost has a bonding hand, and a group represented by $NR^{11}R^{12}$ refers to a monovalent group in which the nitrogen atom at the leftmost side has a bonding hand. In addition, for example, a group represented by $NR^5$ refers to a divalent group in which the nitrogen atom at the leftmost side has a bonding hand.

As embodiments of the compound of the present invention, the following compounds can be mentioned.

Embodiment 1

The compound of the present invention, in which $R^{3a}$, $R^{3b}$, $R^{3c}$, and $R^{3d}$ are each independently a hydrogen atom, a phenyl group optionally having one or more substituents selected from Group H, a 6-membered aromatic heterocyclic group selected from Group V in which the 6-membered aromatic heterocyclic group optionally has one or more substituents selected from Group H, or a 5-membered aromatic heterocyclic group selected from Group W in which the 5-membered aromatic heterocyclic group optionally has one or more substitutents selected from Group H:

Group V:

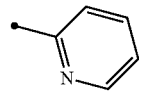

V-1

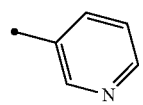

V-2

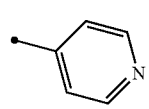

V-3

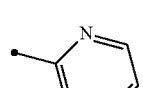

V-4

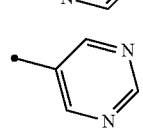

V-5

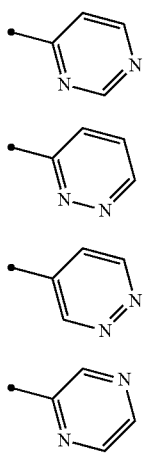
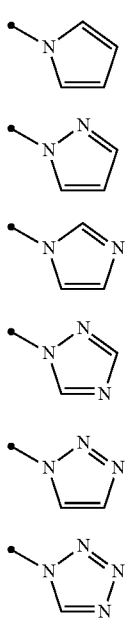
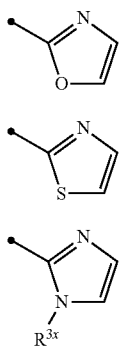
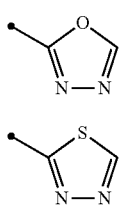
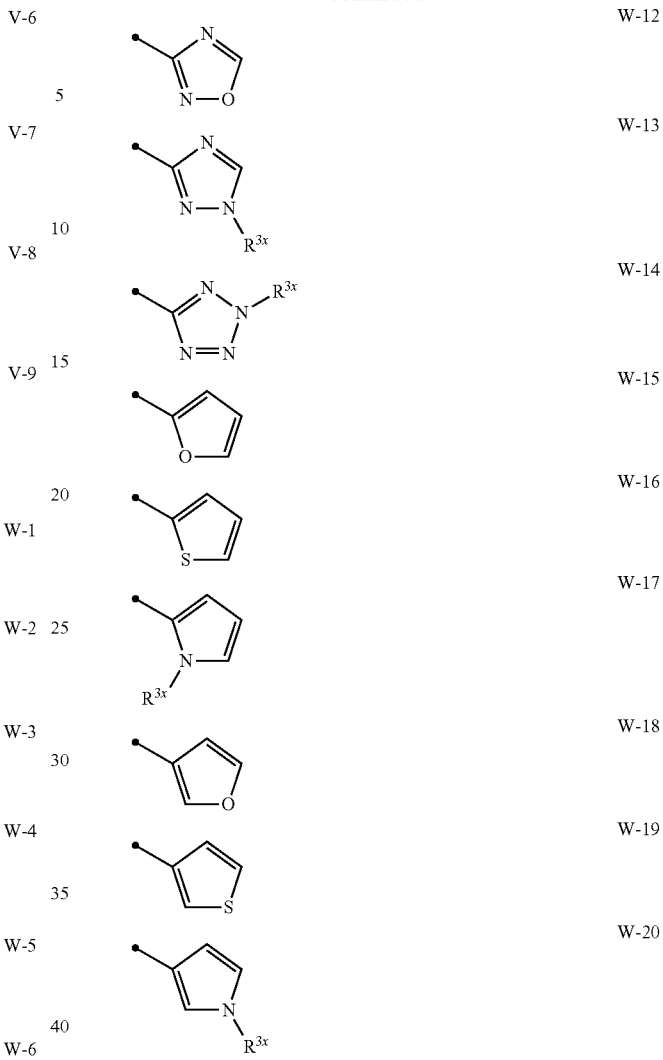

in the drawings, $R^{3x}$ represents a C1-C6 alkyl group optionally having one or more halogen atoms.

Embodiment 2

The compound of the present invention, in which $A^2$ is $CR^{4a}$ and $A^4$ is $CR^{4c}$.

Embodiment 3

The compound according to Embodiment 2, in which Q is a group represented by Formula Q1 or a group represented by Formula Q2.

Embodiment 4

The compound according to Embodiment 2, in which Q is a group represented by Formula Q1, $R^2$ is a C1-C6 alkyl group, $R^{3a}$, $R^{3b}$, $R^{3c}$, and $R^{3d}$ are each independently a C1-C6 alkyl group optionally having one or more halogen atoms, a phenyl group, a 6-membered aromatic heterocyclic group, a 5-membered aromatic heterocyclic group having 1 to 4 nitrogen atoms, in which the phenyl group, the 6-membered aromatic heterocycle group, and the 5-membered aromatic heterocyclic group having 1 to 4 nitrogen atoms each independently optionally has one or more substituents selected from Group H,
$NR^{11}R^{12}$, $NR^{11}C(O)OR^{14}$, a hydrogen atom, or a halogen atom.

Embodiment 5

The compound according to Embodiment 2, in which Q is a group represented by Formula Q1, $R^2$ is at C1-C6 alkyl group, $R^{3a}$, $R^{3b}$, $R^{3c}$, and $R^{3d}$ each independently represents a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms or halogen atoms.

Embodiment 6

The compound according to Embodiment 2, in which Q is a group represented by Formula Q1, $R^2$ is an ethyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms.

Embodiment 7

The compound of Embodiment 2, in which Q is a group, represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, a phenyl group, a pyridyl group, a pyrimidyl group, a pyrazolyl group, a triazolyl group, in which the phenyl group, the pyridyl group, the pyrimidinyl group, the pyrazolyl group, and the friazolyl group each independently optionally has one or more substituents selected from Group H,
an amino group $NR^{11}C(O)OR^{14}$, a hydrogen atom, or a halogen atom, and $R^{4a}$ and $R^{4c}$ are hydrogen atoms.

Embodiment 8

The compound according to Embodiment 2, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, or a hydrogen atom, and $R^{4a}$ and $R^{4c}$ are hydrogen atoms.

Embodiment 9

The compound according to Embodiment 2, in which Q is a group represented by Formula Q2, $R^2$ is a C1-C6 alkyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group; and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms or halogen atoms.

Embodiment 10

The compound according to Embodiment 2, in which Q is a group represented by Formula Q2, $R^2$ is an ethyl group, $R^{3a}$, $R^{3b}$, $R^{3c}$, and $R^{3d}$, are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms.

Embodiment 11

The compound of the present invention, in which $A^2$ is $CR^{4a}$, $A^3$ is $CR^{4b}$, and $A^4$ is $CR^{4c}$.

Embodiment 12

The compound according to Embodiment 11, in which Q is a group represented by Formula Q1 or a group represented by Formula Q2.

Embodiment 13

The compound according to Embodiment 11, in which Q is a group represented by Formula Q1, $R^2$ is a C1-C6 alkyl group, $R^{3a}$, $R^{3b}$, $R^{3c}$, and $R^{3d}$ are each independently a C1-C6 alkyl group optionally having one or more halogen atoms, a phenyl group, a 6-membered aromatic heterocyclic group, a 5-membered aromatic heterocyclic group having 1 to 4 nitrogen atoms, in which the phenyl group, the 6-membered aromatic heterocycle group, and the 5-membered aromatic heterocyclic group having 1 to 4 nitrogen atoms each independently optionally has one or more substituents selected from Group H,
$NR^{11}R^{12}$, $NR^{11}C(O)OR^{14}$, a hydrogen atom, or a halogen atom.

Embodiment 14

The compound according to Embodiment 11, in which Q is a group represented by Formula Q1, $R^2$ is a C1-C6 alkyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl groups, a triazolyl group, in which the phenyl group, the pyridyl group the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$, $R^{4b}$, and $R^{4c}$ are hydrogen atoms or halogen atoms.

Embodiment 15

The compound according to Embodiments 11, in which Q is a group represented by Formula Q1, $R^2$ is an ethyl group, $R^{3a}$, $R^{3b}$, $R^{3c}$, and $R^{3d}$ are each independently a C1-C6 alkyl group optionally, having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group; and the triazolyl group each independently optionally has one or more substituents from Group H,
an amino group, $NR^{11}C(O)OR^{14}$, a hydrogen atom, or a halogen atom, and $R^{4a}$, $R^{4b}$, and $R^{4c}$ are hydrogen atoms.

Embodiment 16

The compound according to Embodiment 11, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$, $R^{4b}$, and $R^{4c}$ are hydrogen atoms.

Embodiment 17

The compound according to Embodiment 11, in which Q is a group represented by Formula Q1, $R^2$ is an ethyl group $G^1$ and $G^4$ are CH's, $G^2$ is $CR^{3b}$, G, is $CR^{3c}$, $R^{3b}$ and $R^{3e}$ are each independently a C1-C6 alkyl group optionally having one or more halogen atoms, or a hydrogen atom and $R^{4a}$, $R^{4b}$, and $R^{4c}$ are hydrogen atoms.

Embodiment 8

The compound according to Embodiment 11, in which Q is a group represented by Formula Q2, $R^2$ is at C1-C6 alkyl group, $R^{3a}$, $R^{3b}$, $R^{3c}$, and $R^{3d}$ are each independently a C1-C6 alkyl group-optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$, $R^{4b}$, and $R^{4c}$ are hydrogen atoms or halogen atoms:

Embodiment 19

The compound according to Embodiment 11, in which Q is a group represented by Formula Q2, $R^2$ is an ethyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$, $R^{4b}$, and $R^{4c}$ are hydrogen atoms.

Embodiment 20

The compound of the present invention, in which $A^2$ is a nitrogen atom, $A^3$ is $CR^{4b}$ and $A^4$ is $CR^{4c}$.

Embodiment 21

The compound according to Embodiment 20, in which Q is a group represented by Formula Q1 or a group represented by Formula Q2.

Embodiment 22

The compound according to Embodiment 20, in which Q is a group represented by Formula Q1, $R^2$ is a C1-C6 alkyl group, $R^{3a}$, $R^{3b}$, $R^{3c}$, and $R^{3d}$ are each independently a C1-C6 alkyl group optionally having-one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4b}$ and $R^{4c}$ are hydrogen atoms or halogen atoms.

Embodiment 23

The compound according to Embodiment 20 in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3e}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4b}$ and $R^{4c}$ are hydrogen atoms.

Embodiment 24

The compound according to Embodiment 20, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, or a hydrogen atom, and $R^{4b}$ and $R^{4c}$ are hydrogen atoms.

Embodiment 25

The compound of Embodiment 20, in which Q is a group represented by Formula Q2, $R^2$ is an ethyl group $R^{3a}$, $R^{3b}$, $R^{3c}$ and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group and the triazoyl group each independently optionally has one or more substituents selected Group H, an amino group, $NR^{11}C(O)OR^{14}$, a hydrogen atom, or a halogen atom, and $R^{4b}$ and $R^{4c}$ are hydrogen atoms.

Embodiment 26

The compound of the present invention, in which $A^2$ is $CR^{4a}$, $A^3$ is a nitrogen atom, and $A^4$ is $CR^{4c}$.

Embodiment 27

The compound according to Embodiment 26, in which Q is a group represented by Formula Q1 or a group represented by Formula Q2.

Embodiment 28

The compound according to Embodiment 26, in which Q is a group represented by Formula Q1, $R^2$ is a C1-C6 alkyl group, and $R^{3a}$, $R^{3b}$, $R^{3c}$, and $R^{3d}$ are each independently a C1-C6 alkyl group optionally having one or more halogen atoms, a phenyl group, a 6-membered aromatic, heterocyclic group, a 5-membered aromatic heterocyclic group having 1 to 4 nitrogen atoms, in which the phenyl group, the 6-membered aromatic heterocycle group, and the 5-membered aromatic heterocyclic group having 1 to 4 nitrogen atoms each independently optionally has one or more substituents selected from Group H,
$NR^{11}R^{12}$, $NR^{11}C(O)OR^{14}$, a hydrogen atom, or a halogen atom.

Embodiment 29

The compound according to Embodiment 26, in which Q is a group represented by Formula Q, $R^2$ is a C1-C6 alkyl group, $R^{3a}$, $R^{3b}$, $R^{3c}$, and $R^{3d}$ are each independently a C1-C6 alkyl group, optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$ and $R^{4e}$ are hydrogen atoms or halogen atoms.

Embodiment 30

The compound according to Embodiment 26, in which Q is a group represented by Formula Q1, $R^2$ is an ethyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group a triazolyl group, in which the phenyl group, the pyridyl group, the pyrimidinyl group, the pyrazolyl group; and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms.

Embodiment 31

The compound according to Embodiment 26, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H, an amino group, $NR^{11}C(O)OR^{14}$, a hydrogen atom, or a halogen atom, and $R^{4a}$ and $R^{4c}$ are hydrogen atoms.

Embodiment 32

The compound according to Embodiment 26, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3e}$ are each independently a C1-C6 alkyl group optionally having one or more halogen atoms, or a hydrogen atom, and $R^{4a}$ and $R^4$ are hydrogen atoms.

Embodiment 33

The compound according to Embodiment 26, in which Q is a group represented by Formula Q2, $R^2$ is a C1-C6 alkyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group; and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms or halogen atoms.

Embodiment 34

The compound according to Embodiment 26, in which Q is a group represented by Formula Q2, $R^2$ is an ethyl group, $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom, and $R^{4a}$ and $R^{4c}$ are hydrogen atoms.

Embodiment 35

The compound of the present invention, in which $A^2$ is $CR^{4a}$, $A^3$ is $CR^{4b}$, and $A^4$ is a nitrogen atom.

Embodiment 36

The compound according to Embodiment 35, in which Q is a group represented by Formula Q1 or a group represented by Formula Q2.

Embodiment 37

The compound according to Embodiment 35, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, a phenyl group a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H,
an amino group, $NR^{11}C(O)OR^{14}$, a hydrogen atom, or a halogen atom and $R^{4a}$ and $R^{4b}$ are hydrogen atoms.

Embodiment 38

The compound according to Embodiment 35, in which Q is a group represented by Formula Q1, $R^2$ is an ethyl group, $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, or a hydrogen atom, and $R^{4a}$ and $R^{4b}$ are hydrogen atoms.

Embodiment 39

The compound of the present invention, in which T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more-halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$. $S(O)_mR^1$, $OS(O)_2R^1$, $NR^1R^2$, a group represented by Formula T-1, a group represented by Formula T-2, a group represented by Formula T-3, a group represented by Formula T-4, a group represented by Formula T-5, a group represented by Formula T-6, a group represented by Formula T-7, or a group represented by Formula T-8, and $R^1$, $R^{1x}$, $R^{1y}$, and $R^{1ay}$ are each independently a C1-C5 chain hydrocarbon group having one or more halogen atoms.

Embodiment 40

The compound of the present invention, in which T is a C1-C10 chain hydrocarbon group having one or more halogen atoms, a (C1-C5 alkoxy) C2-C5 alkyl group having one or more halogen atoms, a (C1-C5 alkylsulfanyl). C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group, having one or more substituents selected from Group G, a C3-C7 cycloalkyl group having one or more substituents selected from Group G, $OR^1$, $S(O)_mR^1$, $OS(O)_2R^1$, $NR^1R^{29}$, a group represented by Formula T-1, a group represented by Formula T-2, a group represented by Formula T-3, a group represented by Formula T-4, a group represented by Formula T-5, a group represented by Formula T-6, a group represented by Formula T-7, or a group represented by Formula T-8, and $R^1$, $R^{1x}$, $R^{1y}$, and $R^{1ay}$ are each independently a C1-C5 alkyl group having three or more fluorine atoms.

Embodiment 41

The compound of the present invention, in which T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfonyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$.

Embodiment 42

The compound of the present invention, in which T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$ and $R^1$ is a C1-C5 chain hydrocarbon group having one or more halogen atoms.

Embodiment 43

The compound of the present invention, in which T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$, and $R^1$ is a C1-C5 alkyl group having three or more fluorine atoms.

Embodiment 44

The compound of the present invention, in which T is a group represented by Formula T-1, a group represented by Formula T-2, a group represented by Formula T-3, a group represented by Formula T-4, a group represented by Formula T-5, a group represented by Formula T-6, a group represented by Formula T-7, or a group represented by Formula T-8, and $R^{1x}$ and $R^{1y}$ are each independently a C1-C5 alkyl group having three or more fluorine atoms.

Embodiment 45

The compound of the present invention, in which T is $OR^1$.

Embodiment 46

The compound of the present invention, in which T is $OR^1$, and $R^1$ is a C1-C5 chain hydrocarbon group having one or more halogen atoms.

Embodiment 47

The compound of the present invention, in which T is $OR^1$, and $R^1$ is a C1-C5 alkyl group having three or more fluorine atoms,

Embodiment 48

The compound according to any one of Embodiments 1 to 38, in which T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, $NR^1R^2$, a group represented by Formula T-1, a group represented by Formula T-2, a group represented by Formula T-3, a group represented by Formula T-4, a group represented by Formula T-5, a group represented by Formula T-6, a group represented by Formula T-7, or a group represented by Formula T-8, and $R^1$, $R^{1x}$, and $R^{1y}$ are each independently a C1-C5 chain hydrocarbon group having one or more halogen atoms.

Embodiment 49

The compound according to any one of Embodiments 1 to 38, in which T is a C1-C10 chain hydrocarbon group having one or more halogen atoms, a (C1-C5 alkoxy) C2-C5 alkyl group having one or more halogen atom, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O) R^1$, $NR^1R^{29}$, a group represented by Formula T-1, a group represented by Formula T-2, a group represented by Formula T-3, a group represented by Formula T-4, a group represented by Formula T-5, a group-represented by Formula T=6, a group represented by Formula T-7, or a group represented by Formula T-8, and $R^1$, $R^{1x}$, and $R^{1y}$ are each independently a C1-C5 alkyl group having three or more fluorine atoms.

Embodiment 50

The compound according to any one of Embodiments 1 to 38, in-which T is a C1-C10 chain-hydrocarbon group having one or more halogen atoms, a (C1-C5 alkoxy) C2-C5 alkyl group having one or more halogen-atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G a C3-C7 cycloalkyl group- having one or more substituents selected from Group G, $OR^1$, $S(O)_mR^1$, $OS(O)_2R^1$, or $NR^1R^{29}$.

Embodiment 51

The compound according to any one of Embodiments 1 to 38, in which T is a C1-C10 chain hydrocarbon group having-one or more halogen atoms, a (C1-C5 alkoxy) C2-C5 alkyl group having one or more halogen atoms, a (C1-C5 alkylsulfanyl) C2-C5 alkyl group having-one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group CG a C3-C7 cycloalkyl group having one or more substituents selected from Group G, $OR^1$, $S(O)_m^1$, $OS(O)_2R^1$, or $NR^1R^{29}$, and $R^1$ is a C1-C5 chain hydrocarbon group having one or more-halogen atoms.

Embodiment 52

The compound according to any one of Embodiments 1 to 38, in which T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G. $OR^1$, $S(O)_mR^1$, $OS(O)_2R^1$, or $NR^1R^{29}$, and $R^1$ is a C1-C5 alkyl group having three or more fluorine atoms.

Embodiment 53

The compound according to any one of Embodiments 1 to 38, in which T is a group represented by Formula T-1, a group represented by Formula T-2, a group represented by Formula T-3, a group represented by Formula T-4, a group represented by Formula T-5, a group represented by Formula T-6a group represented by Formula T-7, or a group represented by Formula T-8, and $R^1$, $R^{1x}$, and $R^{1y}$ are each independently a C1-C5 alkyl group having three or more fluorine atoms.

Embodiment 54

The compound according to any one of Embodiments 1 to 38, in which T is $OR^1$.

Embodiment 55

The compound according to any one of Embodiments 1 to 38, in which T is OR, and $R^1$ is a C1-C5 chain hydrocarbon group having one or more halogen atoms.

Embodiment 56

The compound according to any one of Embodiments 1 to 38, in which T is $OR^1$, and $R^1$ is a C1-C5 alkyl group having three or more fluorine atoms.

Embodiment 57

The compound or the present invention, in which Q is a group represented by Formula Q1, $G^1$ is $CR^{3a}$, $G^2$ is $CR^{3b}$, $G^3$ is $CR^{3c}$, $G^4$ is a nitrogen atom or $CR^{3d}$, $R^{3a}$, $R^{3b}$, $R^{3c}$, and $R^{3d}$ are each independently a hydrogen atom, a halogen atom, or a C1-C10 alkyl group having one or more halogen atoms, $R^2$ is a C1-C6 alkyl group optionally having one or more halogen atoms, $A^2$, $A^3$, and $A^4$ are CH's, or anyone of $A^2$, $A^3$, and $A^4$ is a nitrogen atom and the remainder thereof are CH's, and T is a group selected from Group K, Group K:

a group consisting of a C1-C10 chain hydrocarbon group having one or more halogen atoms such as a difluoromethyl group, a trifluoromethyl group, as 2,2,2-trifluoroethyl group, a perfluoroethyl group, a 2,2,3,3,3-pentafluoropropyl group, a perfluoropropyl group, a perfluorobutyl group, and a perfluoropentyl group;

a group represented by $OR^1$ such as a trifluoromethoxy group, a 1,2,2-tetrafluoroethoxy group, a 2,2-difluoroethoxy group, a 2,2,2-trifluoroethoxy group, a perfluoroethoxy group, a 1-methyl-2,2,2-trifluoroethoxy group, a 2,2,3,3-tetrafluoropropoxy group, a 2,2,3,3,3-pentafluoropropoxy group, a perfluoropropoxy group, a 2,2,3,4,4,4-hexafluorobutoxy group, a 2,2,3,3,4,4,4-heptafluorobutoxy group, a perfluorobutoxy group, and a 2,2,3,3,4,4,5,5,5-nonafluoropentyloxy group;

a group represented by $S(O)_mR^1$ such as a trifluoromethylsulfanyl group, a 2,2,2-trifluoroethylsulfanyl group, a perfluoroethylsulfariyl group, a 2,2,3,3,3-pentafluoropropylsulfanyl group, a perfluoropropylsulfanyl group, a 2,2,3,3,4,4,4-heptafluorobutylsulfanyl group, a perfluorobutylsulfanyl group, a trifluoromethylsulfinyl group, a 2,2,2-trifluoroethylsulfinyl group, a perfluoroethylsulfonyl group, a 2,2,3,3,3-pentaluoropropylsulfinyl group, a perfluoropropylsulfonyl group, a 2,2,3,3,4,4,4-heptafluorobutylsulfinyl group, a perfluorobutylsulfonyl group, a trifluoromethylsulfonyl group, a 2,2,2-trifluoroethylsulfonyl group, a perfluoroethylsulfonyl group, a 2,2,3,3,3-pentafluoropropylsulfonyl group, a perfluoropropylsulfonyl group, a 2,2,3,3,4,4-heptafluorobutylsulfonyl group, and a perfluorobutylsulfonyl group;

a group represented by $OS(O)_2R^1$ such as a trifluoromethylsulfonyloxy group, a perfluoroethylsulfonyloxy group, and a perfluoropropylsulfonyloxy group;

a group represented by $CH_2OR^1$ such as a trifluoromethoxymethyl group, a 2,2,2-trifluoroethoxymethyl group, and a perfluoroethoxymethyl group;

a group represented by $NR^1R^{29}$ such as a 2,2,2-trifluoroethylamino group, a 2,2,3,3,3-pentafluoropropylamino group, a 2,2,3,3,4,4-heptafluorobutylamino group, an N-methyl-2,2,2-trifluoroethylamino group, an N-methyl-2,2,3,3,3-pentafluoropropylamino group, an N-methyl-2,2,3,3,4,4,4-heptafluorobutylamino group, an N-ethyl-2,2,2-trifluoroethylamino group, an N-ethyl-2,2,3,3,3-pentafluoropropylamino group, and an N-ethyl-2,2,3,3,4,4,4-heptafluorobutylamino group;

a group represented by $C(O)R^1$ such as a trifluoromethylcarbonyl group, a perfluoroethylcarbonyl group, and a perfluoropropylcarbonyl group;

a group represented by $C(O)NR^1R^{29}$ such as N-methyl-N-(2,2,2-trifluoroethyl)carbamoyl group;

a group represented by $NR^{29}C(O)R^1$ such as an N-methyl-trifluoromethylcarbonylamino group;

a group represented by $N=CR^1R^{30}$ such as a 1-ethyl-3,3,3-trifluoropropylideneamino group;

a group represented by Formula T-1 such as a 3-trifluoromethylphenyl group, a 3,5-bis(trifluoromethyl)phenyl group, a 3-(trifluoromethylsulfanyl)phenyl group, a 3-(trifluoromethylsulfinyl)phenyl group, a 3-(trifluoromethylsulfonyl)phenyl group, a 4-trifluoromethyl-2-pyridyl group, a 4-(trifluoromethylsulfanyl)-2-pyridyl group, a 4-(trifluoromethylsulfinyl)-2-pyridyl group, a 4-(trifluoromethylsulfonyl)-2-pyridyl group, a 5-trifluoromethyl-3-pyridyl group, a 5-(trifluoromethylsulfanyl)-3-pyridyl group, a 5-(trifluoromethylsulfinyl)-3-pyridyl group, and a 5-(fluoromethylsulfonyl)-3-pyridyl group;

a group represented by Formula T-2 such as a 4-trifluoromethylphenyl group, a 4-(trifluoromethylsulfanyl)phenyl group, a 4-(trifluoromethylsulfinyl)phenyl group, a 4-(trifluoromethylsulfonyl)phenyl group, a 5-trifluoromethyl-2-pyridyl group, a 5-(trifluoromethylsulfanyl)-2-pyridyl group, a 5-(trifluoromethylsulfinyl)-2=pyridyl group, a 5-(trifluoromethylsulfanyl)-2-pyridyl group, a 6-trifluoromethyl-3-pyridyl group, a 6-(trifluoromethylsulfanyl)-3-pyridyl group a 6-(trifluoromethylsulfinyl)-3-pyridyl group, a 6-(trifluoromethiyl sulfonyl)-3-pyridyl group, a 5-(N-methyl-2,2-trifluoroethylamino)-2-pyridyl group, and a 6-(N-methyl-2,2,2-trifluoroethylamino)-3-pyridyl group;

a group represented by Formula T-3 such as a 2,2-difluoro-1,3-benzodioxol-5-yl group;

a group represented by Formula T-4 such as a 2,2-difluoro-1,3-benzodioxol-4-yl group;

a group represented by Formula T-6 such as a 2-oxo-4-(trifluoromethylsulfanyl)-1(2H)-pyridyl group, a 2-oxo-4-(trifluoromethylsulfinyl)-1(2H)-pyridyl group, and a 2-oxo-4-(trifluoromethylsulfonyl)-1(2H)-pyridyl group and a group, represented by Formula T-8 such as a 4-trifluoromethyl-1-imidazolyl group, a 3-trifluoromethyl-1-pyrazolyl group, a 4-trifluoromethyl-1-pyrazolyl group, and a 3-trifluoromethyl-1H-1,2,4-triazol-1-yl group.

Embodiment 58

The compound of the present invention, in which Q is a group represented by Formula Q1, $G^1$ is $CR^{3a}$, $G^2$ is $CR^{3b}$, $G^3$ is $CR^{3c}$, $G^4$ is a nitrogen atom or $CR^{3d}$, $R^{3a}$, $R^{3b}$, $R^{3c}$, and $R^{3d}$ are each independently a hydrogen atom or a group selected from Group L, $R^2$ is a C1-C6 alkyl group optionally having one or more halogen atoms, $A^2$, $A^3$, and $A^4$ are CH's, or any one of $A^2$, $A^3$, and $A^4$ is a nitrogen atom and the remainder thereof are CH's, and T is a group selected from Group K-1.

Group K-1:

a group consisting of a 2,2,3,3-tetrafluoropropoxy group, a 2,2,3,3,3-pentafluropropoxy group, a 2,2,3,4,4-hexafluorobutoxy group, a 2,2,3,3,4,4,4-heptafluorobutoxy group, a 4-trifluoromethyl-2-pyridyl group, a 5-trifluoromethyl-3-pyridyl group, and a 4-trifuoromethyl-1-pyrazolyl group, Group L:

a group consisting of a C1-C6 chain hydrocarbon group optionally having one or more substituents selected from Group B, such as a methyl group, an ethyl group, a propyl group, an isopropyl group, and a trifluoromethyl group;

a C3-C7 cycloalkyl group optionally having one or more substituents selected from Group E, such as cyclopropyl group and 1-cyanocyclopropyl group;

a phenyl group optionally having one or more substituents selected from Group H, such as a phenyl group, a 3-fluorophenyl group, a 4-fluorophenyl group, a 3-chlorophenyl group, a 4-chlorophenyl group, a 3,4-difluorophenyl group, a 3,5-difluorophenyl group, a 2,4-difluorophenyl group, a 3,4,5-trifluorophenyl group, a 3,4-dichlorophenyl group, a 3,5-dichlorophenyl group, a 3,5-dichloro-4-fluorophenyl group, a 3-cyanophenyl group, a 4-cyanophenyl group, a 3-trifluoromethylphenyl group, a 4-trifluoromethylphenyl group, a 3-dimethylaminophenyl group, a 4-dimethylaminophenyl group, a 4-(dimethylcarbamoyl)phenyl group, a 4-(acetylamino)phenyl group, and a 4-(1H-1,2,4-triazol-1-yl)phenyl group;

a 5- or 6-membered aromatic heterocyclic group optionally having one or more substituents selected from Group H, such as a 1-pyrrolyl group, a 3-fluoro-1-pyrrolyl group, a 3-chloro-1-pyrrolyl group, a 3-bromo-1-pyrrolyl group, a 3-nitro-1-pyrrolyl, group, a 3-amino-1-pyrrolyl group, a 3-methyl-1-pyrrolyl group, a 3-trifluoromethyl-1-pyrrolyl group, a 3-methoxy-1-pyrrolyl group, a 1-imidazolyl group, a 4-fluoro-1-imidazolyl group, a 4-chloroo-1-imidazolyl group, a 4-bromo-1-imidazolyl group, a 4-nitro-1-imidazolyl group, a 4-amino-1-imidazolyl group, a 4-methyl-1-imidazolyl group, a 4-trifluoromethyl-=imidazolyl group, a 4-methoxy-1-imidazolyl group, a 1-pyrazolyl group, a 4-fluoro-1-pyrazoyl group, a 4-chloro-1-pyrazolyl group, a 4-bromo-1-pyrazolyl group, a 4-nito 1-pyrazolyl group, a 3-methyl-1-pyrazolyl group, a 1-methyl-4-pyrazolyl group, a 3-trifluoromethyl-1-pyrazolyl group, a 4-trifluoromethyl-1-pyrazolyl group, a 4-methoxy-1-pyrazolyl group, a 1H-1, 2,4-triazol-1-yl group, a 3-fluoro-1H-1,2,4-triazol-1-yl group, a 3-chloro-1H-1,2,4-triazol-1-yl group, a 3-bromo-1H-1,2,4-triazol-1-yl group, a 3-nitro-1H-1,2,4-triazole-1-yl group, a 3-amino-1H-1,2,4-triazole-1-yl group, a 3-methyl-1H-1,2,4-triazol-1-yl group, a 3-trifluoromethyl-1H-1,2,4-triazol-1-yl group, a 3-methoxy-1H-1,2,4-triazol-1-yl group, a 2-pyridyl group, a 3-pyridyl group, a 4-pyridyl group, a 4-fluoro-2-pyridyl group, a 3,5-difluoro-2-pyridyl group, a 5-fluoro-2-pyridyl group, a 4-chloro-2-pyridyl group, a 5-chloro-2-pyridyl group, a 6-fluoro-3-pyridyl group, a 6-chloro-3-pyridyl group, a 5-cyano-2-pyridyl group, a 4-cyano-2-oxo-1 (2H)-pyridyl group, a 5-(1H-1,2,4-triazol-1-yl)-2-pyridyl group, a 3-methyl-2-pyridyl group, a 4-methyl-2-pyridyl group, a 5-methyl-2-pyridyl group, a 6-methyl-2-pyridyl group, a 4-trifluoromethyl-2-pyridyl group, a 5-trifluoromethyl-2-pyridyl group, a 2,2,3,3,3-pentafluoropropoxy-2-pyridyl group, a 5-trifluoromethyl-3-pyridyl group, a 6-trifluoromethyl-3-pyridyl group, a 4-trifluoromethiyl-2-oxo-1(2H)-pyridyl group, a 2-oxo-1 (2H)-pyridyl group, a 2-pyrimidinyl group, a 5-pyrimidinyl group, a 5-fluoro-2-pyrimidinyl group, a 5-chloro-2-pyrimidinyl group, a 5-cyano-2-pyrimidinyl group, a 4-trifluoromethyl-2-pyrimidinyl group, a 5-trifluoromethyl-2-pyrimindinyl group, a 5-methoxy-2-pyrimidinyl group, a 2-pyrazinyl group, and a 4-pyridazinyl group;

a group represented by $OR^{12x}$ such as a methoxy group, an ethoxy group, a propoxy group, an isopropoxy group, a phenoxy group, a 2-fluorophenoxy group, a 2-pyridyloxy group, and a 3-pyridyloxy group;

a group represented by $NR^{11}R^{12}$ such as amino group;

a group represented by $NR^{11a}R^{12a}$ such as 2,2,2-trifluoroethylamino group;

a group represented by $NR^{11}C(O)R^{13}$ such as a cyclopropylcarbonylamino group and an N-methyl-cyclopropylcarbonylamino group;

a group represented by $C(O)OR^{17}$ such as an ethoxycarbonyl group;

a group represented by $CR^{30}=NOR^{17}$ such as a (hydroxyimino)methyl group, a (methoxyimino)methyl group, an (ethoxyimino)methyl group, a (2,2,2-trifluoroethoxyimino)methyl group, a 1-(hydroxyimino)ethyl group, a 1-(methoxyimino)ethyl group, an 1-(ethoxyimino)ethyl group, a 1-(2,2,2-trifluoroethoxyimino)ethyl group, and an amino(2,2,2-trifluoroethoxyimino)methyl group, a cyano group, a hydrogen atom; and a halogen atom such as a fluorine atom, a chlorine atom, and a bromine atom.

Embodiment 59

The compound according to Embodiment 58, in which any one of $R^{3a}$, $R^{3b}$, and $R^{3c}$ is a group selected from Group L, and the remainder thereof are hydrogen atoms.

Embodiment 60

The compound of the present invention, in which Q is a group represented by Formula Q2, $G^1$ is CH, $R^{3b}$ is a hydrogen atom, or a C1-C10 alkyl group having one or more halogen atoms, $R^2$ is a C1-C6 alkyl group optionally having one or more halogen atoms, $A^2$, $A^3$ and $A^4$ are, CH's, or any one of $A^2$, $A^3$, and $A^4$ is a nitrogen atom and the remainder thereof are CH's, and T is a group selected from Group K.

Embodiment 61

The compound of the present invention, in which Q is a group represented by Formula Q3, $G^1$ is $CR^{3a}$, $G^2$ is $CR^{3b}$, $G^3$ is $CR^{3b}$, $G^4$ is $CR^{3d}$, $R^{3a}$, $R^{3b}$, $R^{3c}$ and $R^{3d}$ are each independently a hydrogen atom, or a C1-C10 alkyl group having one or more halogen atoms, $R^2$ is a C1-C6 alkyl group optionally having one or more halogen atoms, $A^1$ is $NR^5$ or a sulfur atom, $R^5$ is a C1-C6 alkyl group optionally having one or more halogen atoms, $A^2$, $A^3$, and $A^4$ are CH's, or any one of $A^2$, $A^3$, and $A^4$ is a nitrogen atom and the remainder thereof are CH's, and T is selected from Group K.

Embodiment 62

The compound according to Embodiments 57, 60, and 61, in which the C1-C10 alkyl group having one or more halogen atoms is a trifluoromethyl group.

Embodiment 63

The compound of the present invention, in which $A^2$ is $CR^{4a}$, $A^3$ is $CR^{4b}$, $A^4$ is $CR^{4c}$, Q is a group represented by Formula Q1, $R^2$ is an ethyl group, $G^1$ and $G^4$ are nitrogen atoms or CH's, $G^2$ is $R^{3b}$, $G^3$ is $R^{3c}$, any one of $R^{3b}$ and $R^{3c}$ is a hydrogen atom and the other is a C1-C6 alkyl group optionally having one or more halogen atoms, a hydrogen atom, or a halogen atom, $R^{4a}$, $R^{4b}$, and $R^{4c}$ are hydrogen atoms, and T is a C1-C6 alkyl group optionally having one or more halogen atoms.

Embodiment 64

The compound of the present invention, in which Q is a group represented by Formula Q1, G is a nitrogen atom, $G^2$ is $CR^{3b}$, $G^3$ is $CR^{3c}$, $G^4$ is $CR^{3d}$. $R^{3b}$, $R^{3c}$, and $R^{3d}$ are each independently a hydrogen atom, a halogen atom, or a C1-C10 alkyl group having one or more halogen atoms, $R^2$ is a C1-C6 alkyl group optionally having one or more halogen atoms, $A^2$, $A^3$, and $A^4$ are CH's, or one of $A^2$, $A^3$, and $A^4$ is a nitrogen atom and the remainder thereof are CH's, and T is a group selected from Group K.

Embodiment 65

The compound of the present invention, in which Q is a group represented by Formula Q1, $G^1$ is a nitrogen atom, $G^2$ is $CR^{3b}$, $G^3$ is $CR^{3c}$, $G^4$ is $CR^{3d}$, $R^{3b}$, $R^{3c}$, and $R^{3d}$ are each independently a hydrogen atom or a group selected from Group L, $R^2$ is a C1-C6 alkyl group optionally having one or more halogen atoms, $A^2$, $A^3$, and $A^4$ are CH's, or any one of $A^2$, $A^3$, and $A^4$ is a nitrogen atom and the remainder thereof are CH's, and T is a group selected from Group K-1.

Embodiment 66

The compound according to Embodiment 65, in which any one of $R^{3b}$ and $R^{3c}$ is a group selected from Group L, and the remainder thereof is a hydrogen atom.

Embodiment 67

The compound according to Embodiment 64, in which the C1-C10 alkyl group having one or more halogen atoms is a trifluoromethyl group.

Embodiment 68

The compound of the present invention, in which $A^2$ is $CR^{4a}$, $A^3$ is $CR^{4b}$, $A^4$ is $CR^{4c}$, Q is a group represented by Formula Q1, $R^2$ is an ethyl group, $G^1$ is a nitrogen atom, $G^2$ is $CR^{3b}$, $G^3$ is $CR^{3c}$, $G^4$ is CH, any one of $R^{3b}$ and $R^{3c}$ is a hydrogen atom and the other is a C1-C6 alkyl group optionally having one or more halogen atoms, a hydrogen atom, or a halogen atom, $R^{4a}$, $R^{4b}$, and $R^{4c}$ are hydrogen atoms, and T is a C1-C6 alkyl group optionally having one or more halogen atoms.

Embodiment 69

The compound of the present invention, in which $A^2$ is $CR^{4a}$, $A^3$ is $CR^{4b}$, $A^4$ is a nitrogen atom, Q is a group represented by Formula Q1, $R^2$ is an ethyl group, $G^1$ is a nitrogen atom, $G^2$ is $CR^{3b}$, $G^3$ is $CR^{3c}$, $G^4$ is CH, any one of $R^{3b}$ and $R^{3c}$ is a hydrogen atom and the other is a C1-C6 alkyl group optionally having one or more halogen atoms, a hydrogen atom, or a halogen atom, $R^{4a}$ and $R^{4b}$ are hydrogen atoms, and T is a C1-C6 alkyl group optionally having one or more halogen atoms.

Embodiment 70

The compound of the present invention, in which $A^2$ is a nitrogen atom, $A^3$ is $CR^{4b}$, $A^4$ is $CR^{4c}$, Q is a group represented by Formula Q1, $R^2$ is an ethyl group, $G^1$ and $G^4$ are nitrogen atoms or CH's, $G^2$ is $CR^{3b}$, $G^3$ is $CR^{3c}$, any one of $R^{3b}$ and $R^{3c}$ is a hydrogen atom and the other is a C1-C6 alkyl group optionally having one or more halogen atoms, a hydrogen atom, or a halogen atom, $R^{4b}$ and $R^{4c}$ are hydrogen atoms, and T is a C1-C6 alkyl group optionally having one or more-halogen atoms.

Embodiment 71

The compound of the present invention, in which $A^2$ is $CR^{4a}$, $A^3$ is $CR^{4b}$, $A^4$ is a nitrogen atom, Q is a group represented by Formula Q1, $R^2$ is an ethyl group, $G^1$ and $G^4$ are nitrogen atoms or CH's, $G^2$ is $CR^{3b}$, $G^3$ is $CR^{3c}$, anyone of $R^{3b}$ and $R^{3c}$ is a hydrogen atom, and the other is a C1-C6 alkyl group optionally having one or more halogen atoms, a hydrogen atom, or a halogen atom, $R^{4a}$ and $R^{4b}$ are hydrogen atoms, and T is a C1-C6 alkyl group optionally having one or more halogen atoms.

Embodiment 71

The compound of the present invention, in which $A^2$ is $CR^{4a}$, $A^3$ is a nitrogen atom, $A^4$ is $CR^{4c}$, Q is a group represented by Formula Q1, $R^2$ is an ethyl group, $G^1$ and $G^4$ are nitrogen atoms or CH's, $G^2$ is $CR^{3b}$, $G^3$ is $CR^{3c}$, any one of $R^{3b}$ and $R^{3e}$ is a hydrogen atom and the other is a C1-C6 alkyl group optionally having one or more halogen atoms, a hydrogen atom, or a halogen atom, $R^{4a}$ and $R^4$ are hydrogen atoms, and T is a C1-C6 alkyl group optionally having one or more halogen atoms.

Next, a production method for the compound of the present invention will be described.

Production Method 1

In the compound of the present invention, a compound represented by Formula (II-1-b) (hereinafter referred to as Compound (II-1-b)) or a compound represented by Formula (II-1-c) (hereinafter referred to as Compound (II-1-c)) can be produced by oxidizing a compound represented by Formula (II-1-a) (hereinafter referred to as Compound (II-1-a)).

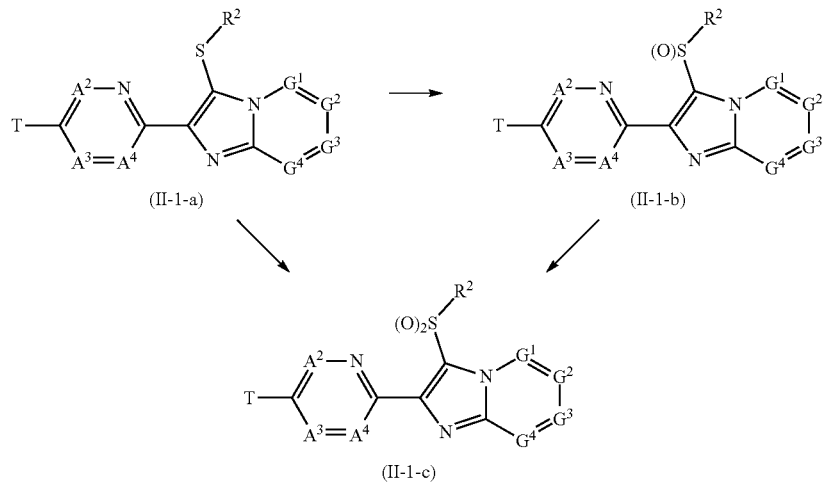

In the formulae, symbols have the same meanings as defined above,

First, a method for producing Compound (II-1-b) from Compound (II-1-a) will be described.

A reaction is usually carried out in a solvent. As the solvent used in the reaction, for example halogenated hydrocarbons (hereinafter referred to as halogenated hydrocarbons) such as dichloromethane and chloroform, nitriles (hereinafter referred to as nitriles) such as acetonitrile, alcohols (hereinafter referred to as alcohols) such as methanol and ethanol, acetic acid, water, and mixtures thereof can be mentioned.

As an oxidizing agent used in the reaction, for example, sodium periodate, m-chloroperbenzoic acid (hereinafter referred to as mCPBA), and hydrogen peroxide can be mentioned.

In a case where hydrogen peroxide is used as the oxidizing agent, a base or a catalyst may be added as necessary.

As the base used in the reaction, sodium carbonate can be mentioned.

As the catalyst used in the reaction, for example, tungstic acid and sodium tungstate can be mentioned.

For the reaction, the oxidizing agent is used in an amount of usually 1 to 1.2 mol. the base is used in an amount of usually 0.01 to 1 mol, and the catalyst is used in an amount of usually 0.01 to 0.5 mol, with respect to 1 mol of Compound (II-1-a).

A reaction temperature is usually in a range of −20° C. to 80° C. A reaction time is usually in a range of 0.1 to 12 hours.

After completion of the reaction, water is added to the reaction mixture, and the reaction mixture is extracted with an organic solvent, and an organic layer is washed with an aqueous solution of a reducing agent (for example, sodium sulfite and sodium thiosulfate) and an aqueous solution of a base (for example, sodium hydrogen carbonate). The organic layer is dried and concentrated, so that Compound (II-1-b) can be obtained.

Next, a method for producing Compound (II-1-c) from Compound (II-1-b) will be described.

A reaction is usually carried out in a solvent. As the solvent used in the reaction, for example, halogenated hydrocarbons, nitriles alcohols, acetic acid, water, and mixtures thereof can be mentioned. As an oxidizing agent used in the reaction, for example, mCPBA, and hydrogen peroxide can be mentioned.

In a case where hydrogen peroxide is used as the oxidizing agent a base or a catalyst may be added as necessary.

As the base used in the reaction, sodium carbonate can be mentioned.

As the catalyst used in the reaction, for example, sodium tungstate can be mentioned.

For the reaction, the oxidizing agent is used in an amount of usually 1 to 2 mol, the base is in an amount of usually 0.01 to 0.1 mol, and the catalyst is used in an amount of usually 0.01 to 0.5 mol, with respect to 1 mol of Compound (II-1-b).

A reaction temperature is usually in a range of −20° C. to 120° C. A reaction time is usually in a range of 0.1 to 12 hours.

After completion of the reaction, water is added to the reaction mixture, and the reaction mixture is extracted with an organic solvent, and an organic layer is washed with an aqueous solution of a reducing agent (for example, sodium sulfite and sodium thiosulfate) and an aqueous solution of a base (for example, sodium hydrogen carbonate). The organic layer is dried and concentrated, so that Compound (II-1-c) can be obtained.

In addition, Compound (II-1-c) can be produced in a one-step reaction (one pot) by reacting Compound (II-1-a) with anoxidizing agent.

The reaction can be carried out according to the method for producing Compound (II-1-c) from Compound (II-1-b) by using an oxidizing, agent in an amount of usually 2 to 5 mol with respect to 1 mol of Compound (II-1-a).

Production Method 2

In the compound of the present invention, a compound represented by Formula (II-2-b) and a compound represented by Formula (II-2-c) can be produced by oxidizing a compound represented by Formula (II-2-a).

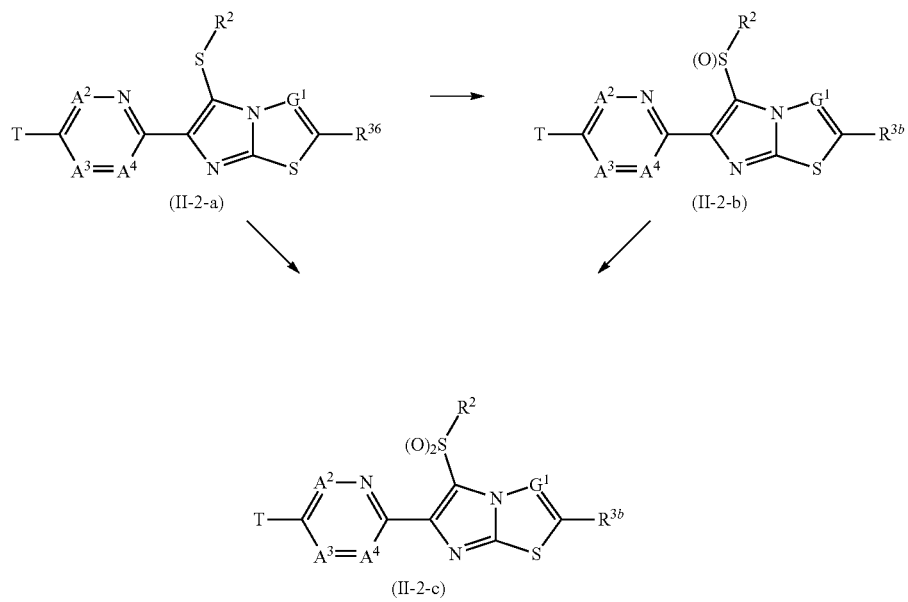

In the formulae, symbols have the same meanings as defined above,

These reactions can be carried out according to the methods described in the production method 1.

Production Method 3

In the compound of the present invention, a compound represented by Formula (II-3-b) and a compound represented by Formula (II-3-c) can be produced by oxidizing a compound represented by Formula ((II-3-a).

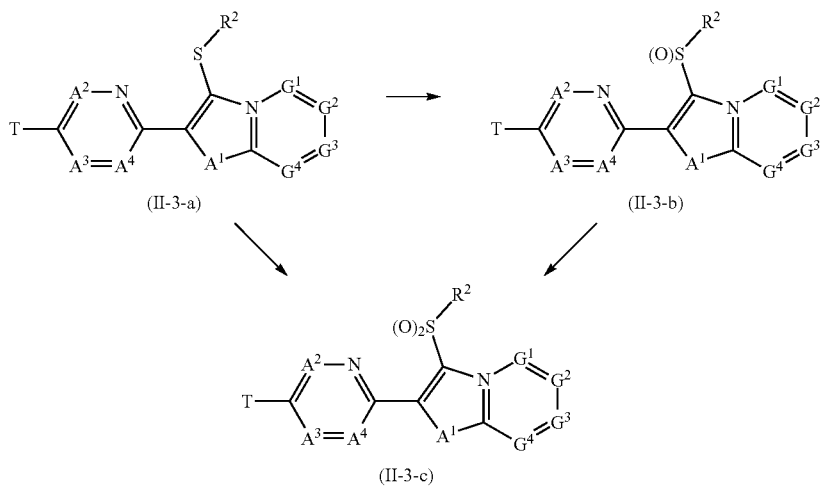

In the formulae, symbols have the same meanings as defined above

These reactions can be carried out according to the methods described in the production method 1.

Production Method 4

Compound (II-1-a) can be produced according to the following scheme.

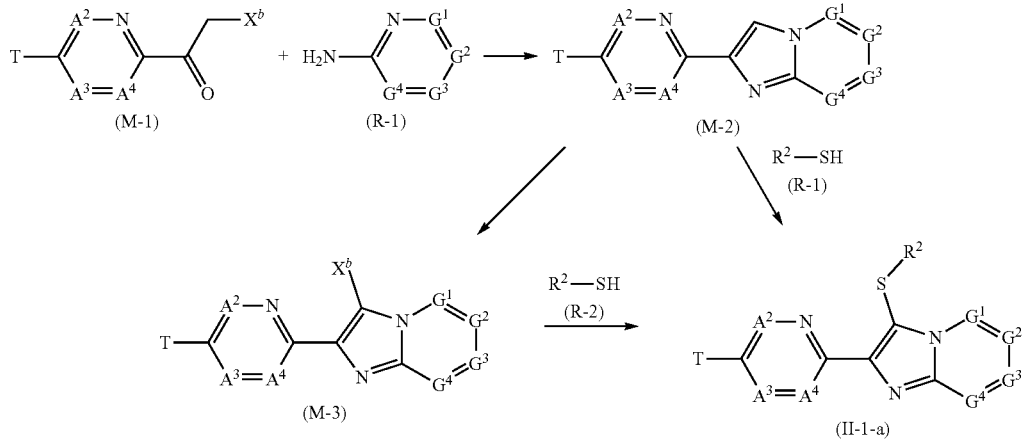

In the formulae, $X^b$ represents a chlorine atom, a bromine atom, or an iodine atom, and the other symbols have the same meanings as defined above.

First, a production method for a compound represented by Formula (M-2) (hereinafter referred to as Compound (M-2)) will be described.

Compound (M-2) can be produced by reacting a compound represented by Formula (M-1) (hereinafter referred to as Compound (M-1)) with a compound represented by Formula (R-1) (hereinafter referred to as Compound (R-1)).

The reaction is usually carried out in a solvent. As the solvent used in the reaction, for example, ethers (hereinafter referred to as ethers) such as tetrahydrofuran (hereinafter referred to as THF), 1,4-dioxane, ethylene glycol dimethyl ether (hereinafter referred to as DME), methyl tert-butyl ether (hereinafter referred to as MTBE), aromatic hydrocarbons (hereinafter referred to as aromatic hydrocarbons) such as toluene and xylene, an aprotic polar solvents (hereinafter referred to as aprotic polar solvents) such as dimethylformamide (hereinafter, referred to as DMF), N-methylpyrrolidone and dimethylsulfoxide (hereinafter referred to as DMSO), alcohols, nitriles, water, and mixtures thereof can be mentioned.

For the reaction, a base can be used as necessary. As the base used in the reaction, for example, organic bases (hereinafter referred to as organic bases) such as: triethylamine, diisopropylethylamine, pyridine, and 4-(dimethylamino) pyridine, alkali metal carbonates (hereinafter referred to as alkali metal carbonates) such as sodium carbonate and potassium carbonate can be mentioned.

For the reaction, Compound (R-1) is used in an, amount of usually 1 to 10 mol and the base is used in an amount of usually 0.1 to 5 mol, with respect to 1 mol of Compound (M-1).

A reaction temperature is usually in a range of −20° C. to 200° C. A reaction time is usually in a range of 0.1 to 48 hours.

After completion of the reaction, water is added to the reaction mixture, the reaction mixture is extracted with an organic solvent, and an organic layer is dried and concentrated, so that Compound (M-2) can be obtained.

Compound (R-1) can be a commercially available compound or can be produced using a known method.

Next, a production method for a compound represented by Formula (M-3) (hereinafter referred to as Compound (M-3)) will be described.

Compound (M-3) can be produced by reacting Compound (M-2) with a halogenating agent.

The reaction is usually carried out in a solvent. As the solvent used in the reaction; for example, alcohols, nitriles, ethers, aromatic hydrocarbons, aprotic polar solvents, halogenated hydrocarbons, water, and mixtures thereof can be mentioned.

As the halogenating agent, chlorine, bromine, iodine, N-chlorosuccinimide, N-bromosuccinimide, N-iodosuccinimide, and the like can be mentioned.

For the reaction, the halogenating agent is used in an amount of usually 1 to 20 mol with respect to 1 mol of Compound (M-2).

A reaction temperature is usually in a range of −20° C. to 200° C. A reaction time is usually in a range of 0.1 to 72 hours.

After completion of the reaction, water is added to the reaction mixture, the reaction mixture is extracted with an organic solvent, and an organic layer is dried and concentrated, so that Compound (M-3) can be obtained.

Next, a method for producing Compound (II-1-a) from Compound (M-2) will be described.

Compound (II-1-a) can be produced by reacting Compound (M-2) with a compound represented by Formula (R-2) (hereinafter referred to as Compound (R-2)) and a halogenating agent.

The reaction is usually carried out in a solvent. As the solvent used in the reaction, for example, alcohols, nitriles, ethers, aromatic hydrocarbons, aprotic polar solvents, halogenated hydrocarbons, water, and mixtures thereof can be mentioned.

As the halogenating agent, chlorine, bromine, iodine, N-chlorosuccinimide, N-bromosuccinimide, N-iodosuccinimide, and the like can be mentioned.

For the reaction, Compound (R-2) is used in an amount of usually 1 to 20 mol with respect to 1 mol of Compound (M-2).

A reaction temperature is usually in a range of −20° C. to 200° C. A reaction time is usually in a range of 0.1 to 72 hours.

After completion of the reaction, water is added to the reaction mixture, the reaction mixture is extracted with an organic solvent, and an organic layer is dried and concentrated, so that Compound (II-1-a) can be obtained. Compound (R-2) can be a commercially available compound or can be produced using a known method.

Next, a method for producing Compound (II-1-a) from Compound (M-3) will be described.

Compound (II-1-a) can also be produced by reacting Compound (M-3) with Compound (R-2) in the presence of a metal catalyst and a base.

The reaction is usually carried out in a solvent. As the solvent used in the reaction, for example, alcohols, nitriles, ethers, aromatic hydrocarbons, aprotic polar solvents, water, aid mixtures thereof can be mentioned.

As the metal catalyst used in the reaction, a palladium catalyst such as tetrakis(triphenylphospliine)-palladium (0), 1,1'-bis(diphenylphosphino) ferrocene palladium (II) dichloride, tris(dibenzylideneacetone) dipalladium (0), and palladium (II) acetate, a nickel catalyst such as bis(cyclooctadiene) nickel (0) and nickel (II) chloride, a copper catalyst such as copper (I) iodide and copper (I) chloride, and the like can be mentioned.

As the base used in the reaction, for example, alkali metal hydrides (hereinafter referred to as alkali metal hydrides) such as sodium hydride, alkali metal carbonates, and organic bases can be mentioned.

For the reaction, a ligand can also be used. As, the ligand used in the reaction, triphenylphosphine, xantphos, 2,2'-bis(diphenylphiosphino)-1,1'-binaphtlhyl, 1,1'-bis(diphenylphosphino) ferrocene, 2-dicyclohexylphosphino-2',4',6'-triisopropyibiphenyl, 2-dicyclohexylphosphino-2',6'-dimethoxybiphenyl, 1,2-bis(diphenylphosphino) ethane, 2,2'-bipyridine, 2-aminoethanol, 8-hydroxyquinoline, 1,10-phenanthroline, and the like can be mentioned.

For the reaction, Compound (R-2) is used in an amount of usually 1 to 20 mol, the metal catalyst is used in an amount of usually 0.01 to 0.5 mol, the ligand is used in an amount of usually 0.01 to 1 mol, and the base is used in an amount of usually 0.1 to 5 mol, with respect to 1 mol of Compound (M-3).

A reaction temperature is usually in a range of −20° C. to 200° C. A reaction time is usually in a range of 0.1 to 72 hours.

After completion of the reaction, water is added to the reaction mixture, the reaction mixture is extracted with an organic solvent, and an organic layer is dried and concentrated, so that Compound (II-1-a) can be obtained.

Production Method 5

Compound (II-1-a) can be produced by reacting Compound (R-1) with a compound represented by Formula (M-4) (hereinafter referred to as Compound (M-4)),

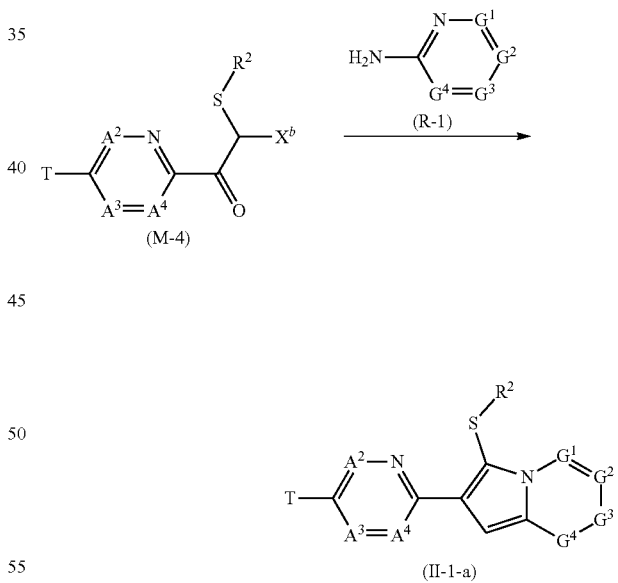

In the formulae, symbols have the same meanings as defined above.

The reaction can be carried out according to the method for producing Compound (M-2) from Compound (M-1) in the production method 4.

Production Method 6

A compound represented by Formula (II-2-a) (hereinafter referred to as Compound (II-2-a)) can be produced according to the following scheme.

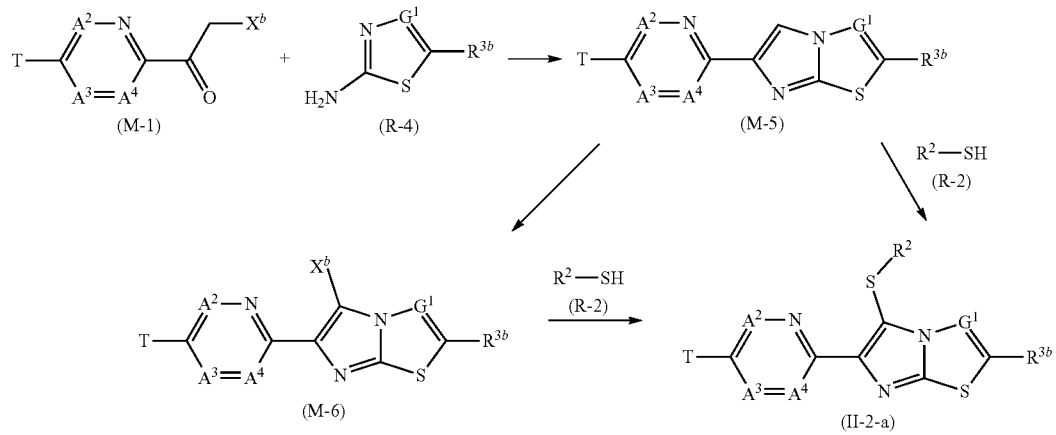

In the formulae, symbols have the same meanings as defined above.

A compound represented by Formula (M-5) (hereinafter referred to as Compound (M-5)) can be produced by reacting Compound (M-1) with a compound represented by Formula (R-4) (hereinafter referred to as Compound (R-4)).

Compound (II-2-a) can be produced by reacting Compound (M-5) with Compound (R-2) and a halogenating agent.

A compound represented by Formula (M-6) (hereinafter referred to as Compound (M-6)) can be produced by reacting Compound (M-5) with a halogenating agent.

Compound (II-2-a) can also be produced by reacting Compound (M-6) with Compound (R-2) in the presence of a metal catalyst and a base.

These reactions can be carried out according to the methods described in the production method 4.

Compound (R-4) can be a commercially available product or can be produced using a known production method.

Production Method 7

Compound (II-2-a) can be produced by reacting Compound (R-4) with Compound (M-4).

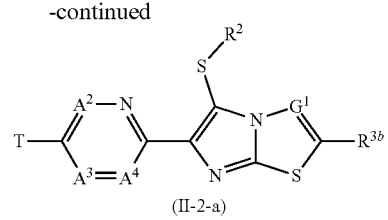

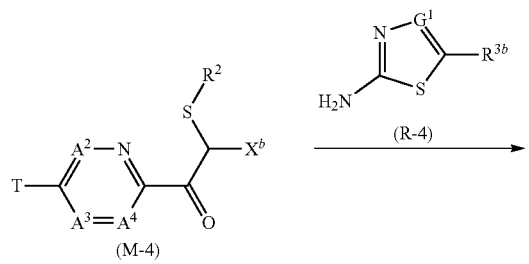

In the formulae, symbols have the same meanings as defined above.

The reaction can be carried out according to the method for producing Compound (M-2), from Compound (M-1) in the production method 4.

Production Method 8

A compound represented by Formula (II-3-a) (hereinafter referred to as Compound (II-3-a)) can be produced according to the following scheme.

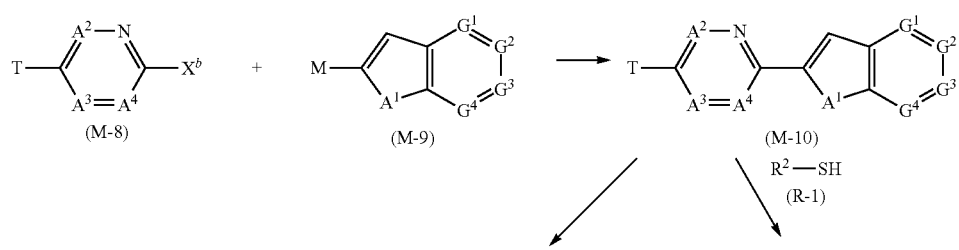

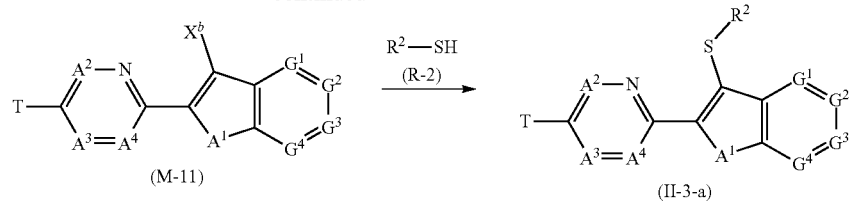

In the formulae, M represents a 9-borabicyclo[3.3.1]nonan-9-yl group, a borono group, a 4,4,5,5-tetramethyl-1,3,2-dioxaborolan-2-yl group, a tributylstannyl group, ZnCl, MgCl, or MgBr, and the other symbols have the same meanings as defined above.

First, a production method for a compound represented by Formula (M-10) (hereinafter referred to as Compound (M-10)) will be described:

Compound (M-10) can be produced by reacting a compound represented by Formula (M-8) (hereinafter referred to as Compound (M-8)) with a compound represented by Formula (M-9) (hereinafter referred to as Compound (M-9)) in the presence of a metal catalyst.

The reaction is usually carried out in a solvent. As the solvent used in the reaction, for example, ethers, aromatic hydrocarbons, aprotic polar solvents, water, and mixtures thereof can be mentioned. As the metal catalyst used in the reaction, a palladium catalyst such as tetrakis(triphenyphosphine) palladium (0), 1,1'-bis(diphenylphosphino) ferrocene palladium (II) dichloride, tris(dibenzylideneacetone) dipalladium (0), and palladium (II) acetate, a nickel catalyst such as bis(cyclooctadiene) nickel (0) and nickel (II) chloride, a copper catalyst such as copper (1) iodide and copper (1) chloride, and the like can be mentioned.

For the reaction, a ligand, a base, or an inorganic halide may be added as necessary.

As the ligand used in the reaction, triphenylphosphine, xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 22'-bipyridine, 2-aminoethanol, 8-hydroxyquinoline 10-phenanthroline, and the like can be mentioned.

As the base used in the reaction, for example, alkali metal hydrides, alkali metal carbonates, and organic bases can be mentioned.

As the inorganic halide used in the reaction, alkali metal fluorides such as potassium fluoride and sodium fluoride, and alkali metal chlorides such as lithium chloride and sodium chloride can be mentioned.

For the reaction, Compound (M-9) is used in an amount of usually 1 to 10 mol, the metal catalyst is used in an amount of usually 0.01 to 0.5 mol, the ligand is used in an amount of usually 0.01 to 1 mol, the base is used in an amount of usually 0.1 to 5 mol, and the inorganic halide is used in an amount of usually 0.1 to 5 mol, with respect to 1 mol of Compound (M-8).

A reaction temperature is usually in a range of −20° C. to 200° C. A reaction time is usually in a range of 0.1 to 24 hours.

After completion of the reaction, water is added to the reaction mixture, the reaction mixture is extracted with an organic solvent, and an organic layer is dried and concentrated, so that Compound (M-10) can be obtained.

Next, a production method for a compound represented by Formula (M-11) (hereinafter referred to as Compound (M-11)) will be described.

Compound (M-11) can be produced by reacting Compound (M-10) with a halogenating, agent. The reaction can be carried out according to the method for producing Compound (M-3) from Compound (M-2) in the production method 4.

Next, a production method for Compound (II-3-a) will be described.

Compound (II-3-a) can be produced by reacting Compound (M-10) with Compound (R-2) and a halogenating agent. The reaction can be carried out according to the method for producing Compound (II-1-a) from Compound (M-2) in the production method 4.

Compound (II-3-a) can also be produced by reacting Compound (M-11) with Compound (R-2) in the presence of a metal catalyst and a base. The reaction can also be carried out according to the method for producing Compound (II-1-a) from Compound (M-3) in the production method 4.

Compound (M-8) can be a commercially available compound, or can be produced using a known production method or a method described in reference production methods 12 to 21. Compound (M-9) is a commercially-available compound or is known.

Synthesis methods for production intermediate compounds will be described below.

Reference Production Method 1

Compounds (M-1) and (M-4) can be produced according to the following scheme.

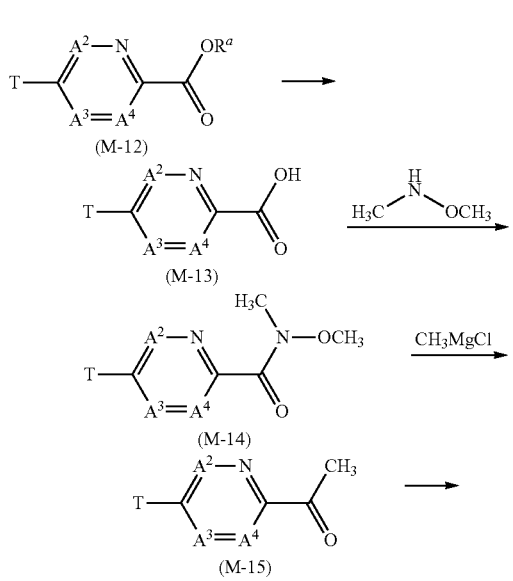

-continued

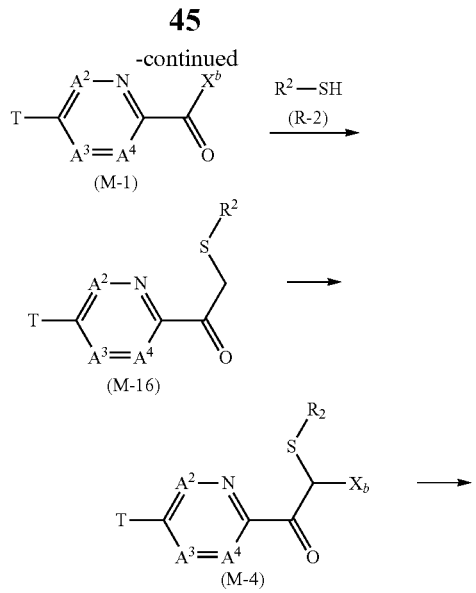

In the formulae, RP represents a methyl group or an ethyl group, and the other symbols have the same meanings as defined above.

A compound represented by Formula (M-14)(hereinafter referred to as Compound-(M-14)) can be produced from a compound represented by Formula (M-12) (hereinafter referred to as Compound (M-12)). A reaction can be carried out, for example, according to the method described in Journal of Medicinal Chemistry, 56, 3980 (2013).

A compound represented by Formula (M-15) (hereinafter referred to as Compound (M-15)) can be produced by reacting Compound (M-14) with methylmagnesium chloride. The reaction can be carried out, for example, according to the method described in PCT International Publication No. WO 2008/116665.

Compound (M-1) can be produced by reacting Compound (M-15) with a halogenating agent. The reaction can be carried out according to the method described in PCT International Publication No WO 2013/191113, A compound represented by Formula (M-16) (hereinafter referred to as Compound (M-16)) can be produced by reacting Compound (M-1) with Compound (R-2) in the presence of a base. The reaction can be carried out according to the method described in Tetrahedron Letters, 64, 7419 (2008).

Compound (M-4) can be produced by reacting Compound (M-16) with a halogenating agent. The reaction can be carried out according to the method described in PCT International Publication No. WO 2013/191113.

Reference Production Method 2

A compound represented by Formula. (M-12a) (hereinafter referred to as Compound (M-12a)) can be produced by reacting a compound represented by Formula (M-18a) (hereinafter, referred to as Compound (M-18a)) with a compound represented by Formula (R-5) (hereinafter referred to as Compound (R-5)) in the presence of a base.

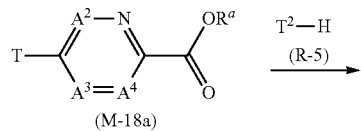

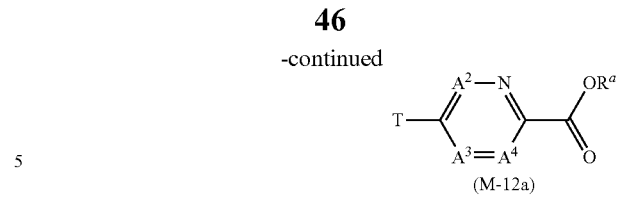

In the formulae, $X^a$ represents a fluorine atom or a chlorine atom, $T^2$ represents $OR^1$, $NR^1R^{29}$, a group represented by Formula T-5, a group represented by Formula T-6, a group represented by Formula T-7, or a group represented by Formula T-8, and the other symbols have the same meanings as defined above.

The reaction is usually carried out in, a solvent. As the solvent, for example ethers, aromatic hydrocarbons, nitriles, aprotic polar solvents, and mixtures thereof can be mentioned.

As the base used in the reaction, for example, alkali metal carbonates or alkali metal hydrides can be mentioned.

For the reaction, Compound (R-5) is used in an amount of usually 1 to 2 mol and the base is used in an amount of usually 1 to 10 mol, with respect to 1 mol of Compound (M-18a).

A reaction temperature is usually in a range of −20° C. to 150° C. A reaction time is usually in a range of 0.5 to 24 hours.

After completion of the reaction, water is added to the reaction mixture, the reaction mixture is extracted with an organic solvent, and an organic layer is dried and concentrated, so that Compound (M-12a) can be obtained.

Compound (R-5) and Compound (M-1.8a) can be commercially available compounds, or can be produced using known methods.

Reference Production Method 3

The compound represented by Formula (M-12b) can be prepared by reacting a compound represented by Formula (M-18b), (hereinafter referred to as Compound (M-18b)) and a compound represented by Formula (R-6) (hereinafter referred to as Compound (R-6)).

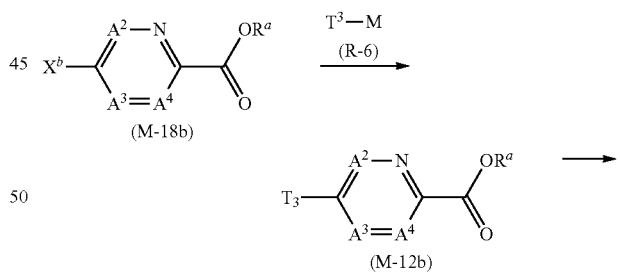

In the formulae, $T^3$ is a group represented by Formula T-1, a group represented by Formula T-2, a group represented by Formula T-3, a group represented by Formula T-4, a group represented by Formula T-9, a group represented by Formula T-10, a group represented by Formula T-11, or a group represented by Formula T-12, and the other symbols have the same meanings as defined above.

The reaction can be carried out according to the method for producing Compound (M-10) as described in the production method 8.

Compound (R-6) and Compound (M-18b) can be commercially available compounds or can be produced using known methods.

Reference Production Method 4

A compound represented by Formula (M-12c) can be produced by reacting a compound represented by Formula (M-18c) (hereinafter referred to as Compound (M-18c)) with a compound represented by Formula (R-7) (hereinafter referred to as Compound (R-7)).

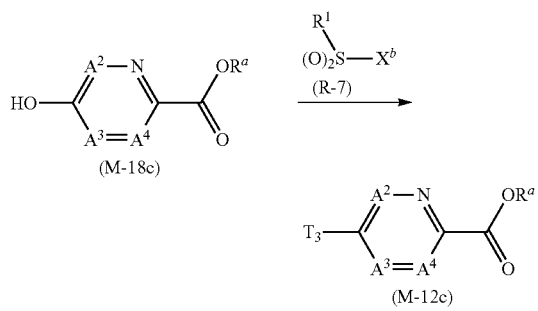

In the formulae, symbols have the same meanings as defined above.

The reaction can be carried out according to the method described in PCT International Publication No. WO 2016/121969:

Compound (R-7) and Compound (M-18c) can be commercially available compounds or can be produced using known methods.

Reference Production Method 5

A compound represented by Formula (M-12d) (hereinafter referred to as Compound (M-12d)) can be produced by reacting Compound (M-18b) with a compound represented by Formula (R-8) (hereinafter referred to as Compound (R-8)) in the presence of copper.

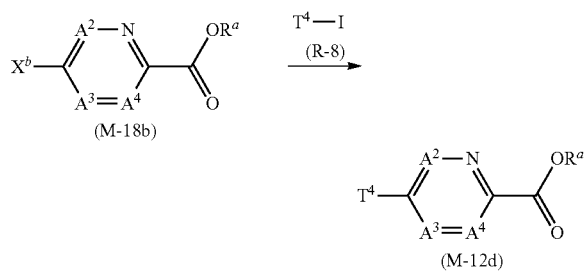

In the formulae, $T^4$ represents a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G. or a C3-C7 cycloalkyl group having one or more substituents selected from Group G, and the other symbols have the same meanings as defined above.

Compound (R-8) can be a commercially available compound or can be produced according to a known method. The reaction is usually carried out in a solvent. As the solvent used in the reaction, for example, aromatic hydrocarbons, aprotic polar solvents, and mixtures thereof can be mentioned.

For the reaction, Compound (R-8) is used in an amount of usually 1 to 10 mol and the copper is used in an amount of usually 1 to 10 mol, with respect to 1 mol of Compound (M-18b).

A reaction temperature is usually in a range of 40° C. to 200° C. A reaction time is usually in a range of 0.1 to 24 hours.

After completion of the reaction, water is added to the reaction mixture, the reaction mixture is extracted with an organic solvent, and an organic layer is dried and concentrated, so that Compound (M-12d) can be obtained.

Reference Production Method 6

A compound represented by Formula (M-12e) (hereafter referred to as Compound (M-12e)) can be produced by reacting a compound represented by Formula (M-18d) (hereinafter referred to as Compound (M-18d)) with a compound represented by Formula (R-9) (hereinafter referred to as Compound (R-9)),

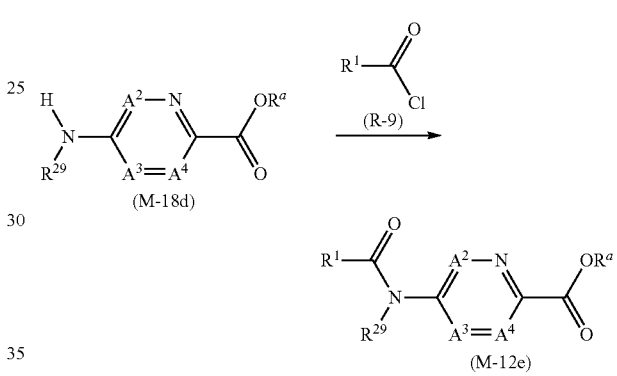

In the formulae, symbols have the same, meanings as defined above.

Compound (M-18d) and Compound (R-9) can be commercially available compounds or can be produced according to known methods.

The reaction is usually carried out in a solvent. As the solvent used in the reaction, for example, ethers, halogenated hydrocarbons, aromatic hydrocarbons, aprotic polar solvents, and mixtures thereof can be mentioned.

For the reaction, abase may be added as necessary. As the base, organic bases can be mentioned. For the reaction, Compound (R-9) is, used in an amount of usually 1 to 10 mol and the base is used in an amount of usually 0.1 to 10 mol, with respect to 1 mol of Compound (M-18d).

A reaction temperature is usually in a range of −20° C. to 120° C. A reaction time is usually in a range of 0.1 to 24 hours.

After completion of the reaction, water is added to the reaction mixture, the reaction mixture is extracted with an organic solvent, and an organic layer is dried and concentrated, so that Compound (M-12e) can be obtained.

Reference Production Method 7

A compound represented by Formula (M-12f) (hereinafter referred to as Compound (M-12f)) can be produced by reacting Compound. (M-18b) with a compound represented by Formula (R-10) (hereinafter referred to as Compound (R-10)) in the presence of a base.

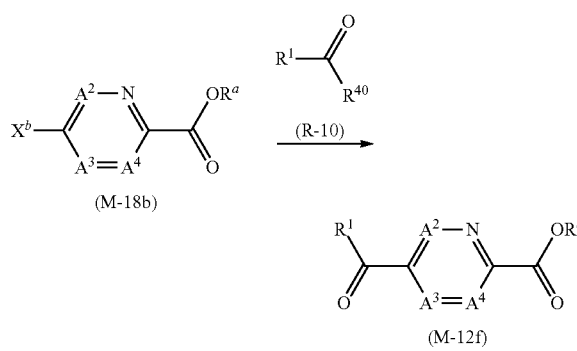

(M-18b)

(R-10)

(M-12f)

In the formulae, $R^{40}$ represents a methoxy group, an ethoxy group, a phenoxy group; or $N(CH_3)OCH_3$, and the other symbols have the same meanings as defined above.

Compound (R-10) can be a commercially available compound or can be produced according to a known method.

The reaction, is usually carried out in a solvent. As the solvent used in the reaction, ethers, and aromatic hydrocarbons can be mentioned.

As the base used in the reaction, butyllithium, lithium diisopropylamide, lithium tetramethylpiperidide, lithium bis (trimethylsilyl) amide, and the like can be mentioned.

For the reaction, Compound (R-10) is used in an amount of usually 1 to 10 mol and the base is usually used in an amount of 1.0 to 2.0 mol, with respect to 1 mol of Compound (M-18b).

A reaction temperature is usually in a range of −100° C. to 60° C. A reaction time is usually in a range of 0.1 to 24 hours.

After completion of the reaction, water is added to the reaction mixture, the reaction mixture is extracted with an organic solvent, and an organic, layer is dried and concentrated, so that Compound (M-12f) can be obtained.

Reference Production Method 8

A compound represented by Formula (M-12 g) (hereinafter referred to as Compound (M-12 g)) can be produced by reacting a compound represented by Formula (M-18e)(hereinafter referred to as Compound (M-18e)) with a compound represented by Formula (R-11) (hereinafter referred to as Compound (R-11)) in the presence of a condensing agent.

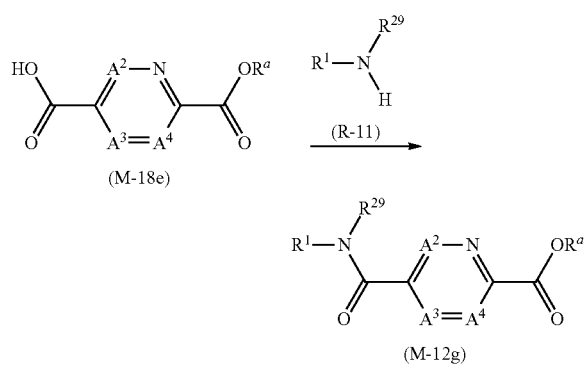

(M-18e)

(R-11)

(M-12g)

In the formulae, symbols have the same meanings as defined above.

Compound (R-11) and Compound (M-18e) can be commercially available compounds or can be produced according to known methods.

The reaction is usually carried out in a solvent. As the solvent used in the reaction, for example, ethers, aliphatic halogenated hydrocarbons, aromatic hydrocarbons, aprotic polar solvents, and mixtures thereof can be mentioned.

As the condensing agent, 1-ethyl-3-(3-dimethylaminopropyl) carbodiimide hydrochloride and the like can be mentioned.

For the reaction, a base may be added as necessary. As the base, organic bases can be mentioned.

For the reaction. Compound (R-11) is used in an amount of usually 1 to 10 mol, the condensing agent is used in an amount of usually 1 to 5, mol, and the base is used in an amount of usually 0.1 to 10 mol, with respect to 1 mol of Compound (M-18e).

A reaction temperature is usually in a range of −20° C. to 120° C. A reaction time is usually in a range of 0.1 to 24 hours.

After completion of the reaction, water is added to the reaction mixture, the reaction mixture is extracted with an organic solvent, and an organic layer is, dried and concentrated, so that Compound (M-12 g) can be obtained.

Reference Production Method 9

A compound represented by Formula (M-12h) (hereinafter referred to as Compound (M-12h)) can be produced by reacting a compound represented by Formula (M-18f) (hereinafter referred to as Compound (M-18f) with a compound represented by Formula (R-12) (hereinafter referred to as Compound (R-12)).

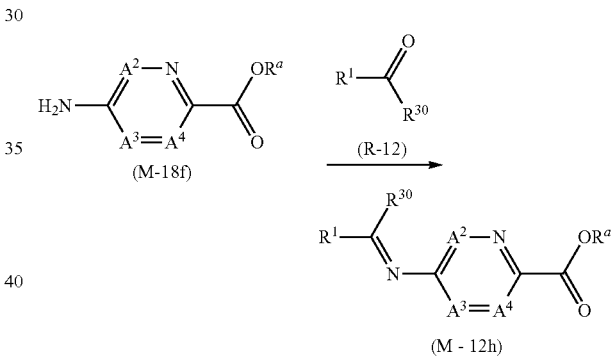

(M-18f)

(R-12)

(M - 12h)

In the formulae, symbols have the same meanings as defined above,

Compound (R-12) and Compound (M-18f) can be commercially available compounds or can be produced according to known methods.

The reaction is usually carried out in a solvent. As the solvent used, in the reaction, for example, ethers, aliphatic halogenated hydrocarbons, aromatic hydrocarbons, aprotic polar solvents, and mixtures thereof can be mentioned.

For the reaction, an acid may be added as necessary. As the acid, p-toluenesulfonic acid and camphorsulfonic acid can be mentioned.

For the reaction, Compound (R-12) is used in an amount of usually 1 to 10 mol and the acid is used in an amount of usually 0.1 to 10 mol, with respect to 1 mol of Compound (M-18f).

A reaction temperature is usually in a range of −20° C. to 180° C. A reaction time is usually in a range of 0.1 to 24 hours.

After completion of the reaction, water is added to the reaction mixture, the reaction mixture is extracted with an organic solvent, and an organic layer is dried and concentrated, so that Compound (M-12h) can be obtained.

Reference Production Method 10

A compound represented by Formula (M-12i) (hereinafter referred to as Compound (M-12i)) can be produced by reacting a compound represented by Formula (M-18 g) (hereinafter referred to as Compound (M-18 g)) with a compound represented by Formula (R-13) (hereinafter referred to as Compound (R-13) in the presence of a base.

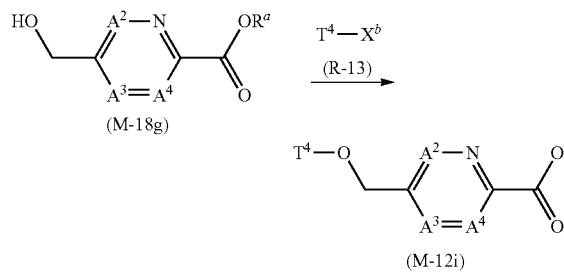

In the formulae, symbols have the same meanings as defined above.

Compound (R-13) and Compound (M-18 g) can be commercially available compounds or can be produced according to known methods.

The reaction is usually carried out in a solvent. As the solvent used in the reaction, ethers, aromatic hydrocarbons, aprotic polar solvents, and mixtures thereof tan be mentioned.

As the base used in the reaction, organic bases, alkali metal hydrides, and alkali metal carbonates can be mentioned, For the reaction, Compound (R-13) is used in an amount of usually 1 to 10 mol and the base is used in an amount of usually 0.1 to 5 mol, with respect to 1 mol of Compound (M-18 g):

A reaction temperature is usually in a range of −20° C. to 120° C. A reaction time is usually in a range of 0.1 to 24 hours.

After completion of the reaction, water is added to the reaction mixture, the reaction mixture is extracted with an organic solvent, and an organic layer is dried and concentrated, so that Compound (M-12i) can be obtained.

Reference Production Method 11

A compound represented by Formula (M-12j) (hereinafter referred to as Compound (M-12j)), a compound represented by Formula (M-12j-1) (hereinafter referred to as Compound (M-12j-1)), and a compound represented by Formula (M-12j-2) (hereinafter referred to as Compound (M-12j-2)) can be produced according to the following methods.

In the formulae, symbols have the same meanings as defined above.

First, a production method for a compound represented by formula (M-20) (hereinafter referred to as Compound (M-20)) will be described.

Compound (M-20) can be produced by reacting Compound (M-18b) with thiobenzoic acid in the presence of a copper catalyst and a base.

The reaction is usually carried out in a solvent. As the solvent used in the reaction, for example, ethers, aromatic hydrocarbons, aprotic polar solvents, water, and mixtures thereof can be mentioned.

As the copper catalyst used in the reaction, copper chloride, copper bromide, copper iodide, and the like can be mentioned.

As the base used in the reaction, alkali metal hydrides, alkali metal carbonates, and organic bases can be mentioned.

For the reaction, a ligand may be added as necessary.

As the ligand used in the reaction, 2,2'-bipyridine, 2-aminoethanol, 8-hydroxyquinoline, 1,10-phenanthroline, and the like can be mentioned.

For the reaction, the thiobenzoic acid is used in an amount of usually 1 to 1.0 mol, the copper catalyst is used in an amount of usually 0.01 to 0.5 mol, the ligand is used in an amount of usually 0.01 to 1 mol, and the base is used in an amount of usually 0.1 to 5 mol, with respect to 1 mol of Compound (M-18b).

A reaction temperature is usually in a range of −20° C. to 200° C. A reaction time is usually in a range of 0.1 to 24 hours.

After completion of the reaction, water is added to the reaction mixture, the reaction mixture is extracted with an organic solvent, and an organic layer is dried and concentrated, so that Compound (M-20) can be obtained.

Subsequently, a production method for a compound represented by Formula (M-21) (hereinafter referred to as Compound (M-21)) will be described.

Compound (M-21) can be produced for example, according to the method described in PCT International Publication No. WO 2011/068171 or the method described in Journal of Organic Chemistry, 1978, 43(6), pp. 1190 to 192.

Subsequently, a production method for Compound (M-12j) will be described.

Compound (M-12j) can be produced according to the method described in the reference production method 10, using Compound (M-21) in place, of Compound (M-18 g).

Subsequently, a production method for Compound (M-12j-1) will be described.

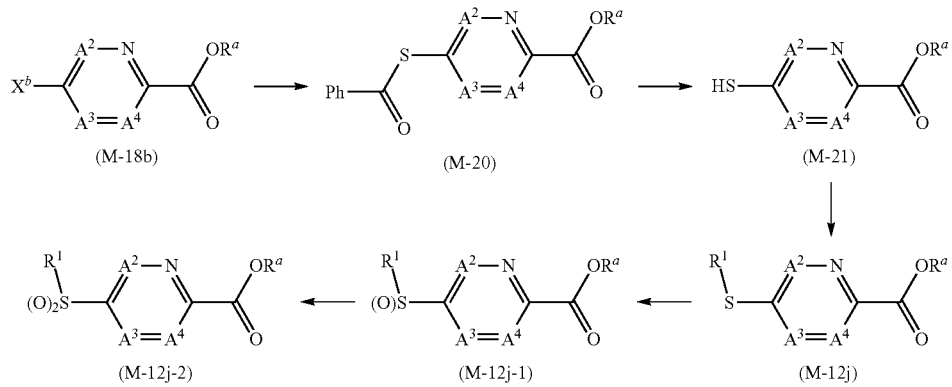

Compound (M-12j-1) can be produced according to the method described in the production method 1, using Compound (M-12j) in place of Compound (II-1-a).

Subsequently, the production method of Compound (M-12j-2) will be described. Compound (M-12'-2) can be produced according to the method described in Production Method 1, using Compound (M-12j-1) in place of Compound (II-1-b).

Reference Production Method 12

A compound represented by Formula (M-8a) (hereinafter referred to as Compound (M-8a)) can be produced by reacting a compound represented by Formula (M-19a) (hereinafter referred to as Compound (M-19a)) with Compound (R-5):

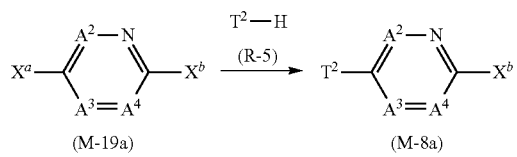

In the formulae, symbols have the same meanings as defined above.

The reaction can be carried out according to the method described in the reference production method 2.

Compound (M-19a) can be a commercially available compound or can be produced using a known method.

Reference Production Method 13

A compound represented by Formula (M-8b) can be produced by reacting a compound represented by Formula (M-19b) (hereinafter referred to as Compound (M-19b) with Compound (R-6).

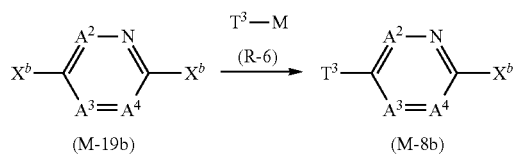

In the formulae, symbols have the same meanings as defined above.

The reaction can be carried out according to the method described in the reference-production method 3.

Compound (M-19b) can be a commercially available compound or can be produced using, a known method.

Reference Production Method 14

A compound represented by Formula (M-8c) (hereinafter referred to as Compound (M-8c)) can be produced by reacting a compound represented by Formula (M-19c) (hereinafter referred to as Compound (M-19c)) with Compound (R-7).

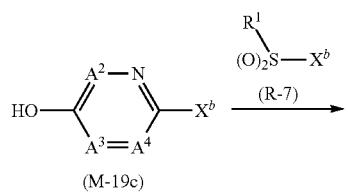

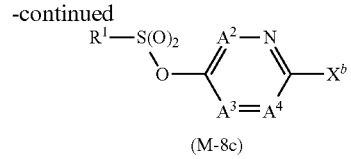

In the formulae, symbols have the same meanings as defined above.

The reaction can be carried out according to the method described in the reference production method 4.

Compound (M-19c) can be a commercially available compound or can be produced using a known method.

Reference Production Method 15

A compound represented by formula (M-8d) (hereinafter referred to as Compound (M-8d)) can be produced by reacting Compound (M-19b) with Compound (R-8).

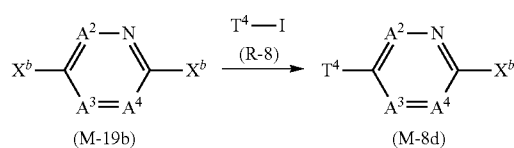

In the formulae, symbols have the same meanings as defined above.

The reaction can be carried out according to the method described in the reference production, method 5.

Reference Production Method 16

A compound represented by Formula (M-8e) (hereinafter referred to as Compound (M-8e)) can be produced by reacting a compound represented by Formula (M-19d) (hereinafter referred to as Compound (M-19 d)) with Compound (R-9).

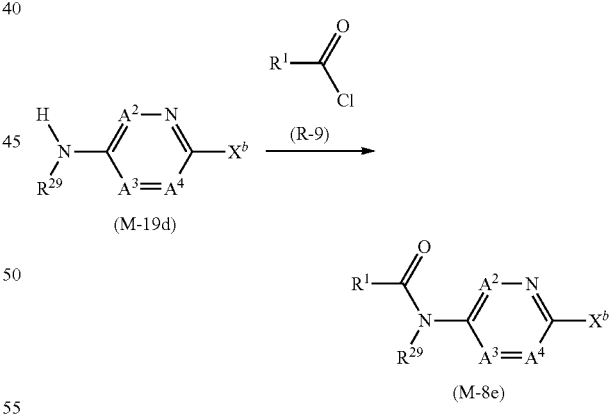

In the formulae, symbols have the same meanings as defined above.

The reaction can be carried out according to the method described in the reference production method 6, Compound (M-19d) can be a commercially available compound or can be produced using a known method.

Reference Production Method 17

A compound represented by Formula (M-8f) (hereinafter referred to as Compound (M-8f)) can be produced by reacting Compound (M-19b) with Compound (R-10).

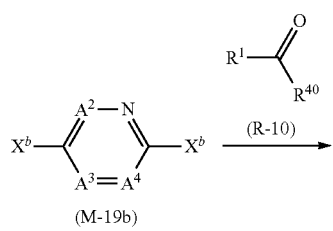

(M-19b)

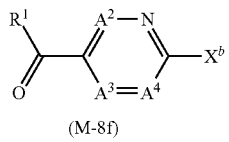

(M-8f)

In the formulae, symbols have the same meanings as defined above.

The reaction can be carried out according to the method described in the reference production method 7.

Reference Production Method 18

A compound represented by Formula (M-8 g) (hereinafter referred to as Compound (M-8 g)) can be produced by reacting a compound represented by Formula (M-19e) (hereinafter referred to as Compound (M-19e)) with Compound (R-11).

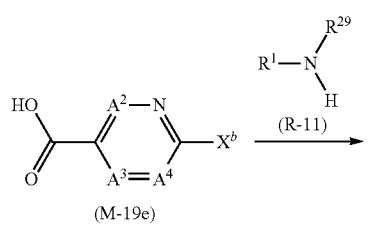

(M-19e)

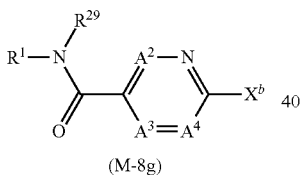

(M-8g)

In the formulae, symbols have the same meanings as defined above.

The reaction can be carried out according to the method described in the reference production method 8.

Compound (M-19e) can be a commercially available compound or can be produced using a known method.

Reference Production Method 19

A compound represented by Formula (M-8h) (hereinafter referred to as Compound (M-8h)) can be produced by reacting a compound represented by Formula (M-19f) (hereinafter referred to as Compound (M-19f)) with Compound (R-12).

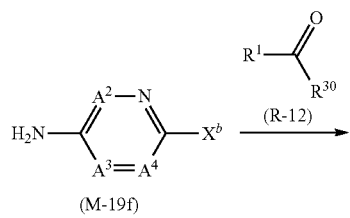

(M-19f)

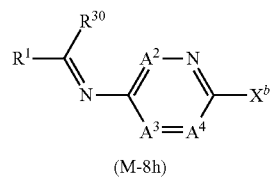

(M-8h)

In the formulae, symbols have the same meanings as defined above.

The reaction can be carried out according to the method described in the reference production, method 9.

Compound (M-19f) can be a commercially available compound or can be produced using a known method.

Reference Production Method 20

A compound represented by Formula (M-8i) (hereinafter referred to as Compound(M-8i)) can be produced by reacting a compound represented by Formula (M-19 g) (hereinafter referred to as Compound (M-19 g)) with Compound (R-13),

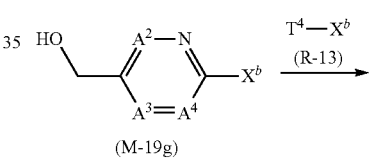

(M-19g)

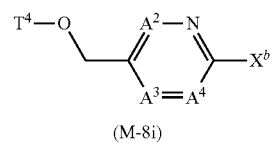

(M-8i)

In the formulae, symbols have the same meanings as defined above.

The reaction can be carried out according to the method described in reference production method 10.

Compound (M-19 g) can be a commercially available compound or can be produced using a known method.

Reference Production Method 21

A compound represented by formula (M-8j) (hereafter referred to as Compound (M-8j)), a compound represented by Formula (M-8j-1). (hereinafter referred to as Compound (M-8j-1), and a compound represented by Formula (M-8j-2) (hereinafter referred to as Compound (M-8j-2) can be produced according to the following methods.

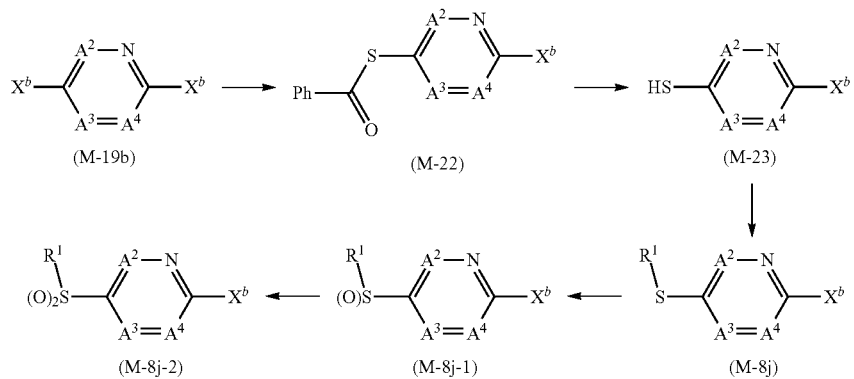

In the formulae, symbols have the same meanings as defined above.

The reactions can be carried out according to the methods described in reference production method 1.1.

Next, specific examples of the compound of the present invention are shown below.

In the present specification, Me represents a methyl group, Et represents an ethyl group, Pr represents a propyl group, i-Pr represents an isopropyl group, c-Pr represents a cyclopropyl group, 1-CN-c-Pr represents a 1-cyanocyclopropyl group, Ph represents a phenyl group, Py2 represents a 2-pyridyl group, Py3 represents a 3-pyridyl group; and Py4 represents a 4-pyridyl group; In a case where c-Pr, Ph, Py2. Py3, and Py4 have a substituent, the substituent is specified before the symbol together with a substitution position. For example, 4-C F-Py2 represents a 4-(trifluoromethyl)-2-pyridyl group and 3,5-$(CF_3)_2$-Ph represents a 3,5-bis(trifluromethyl)phenyl group.

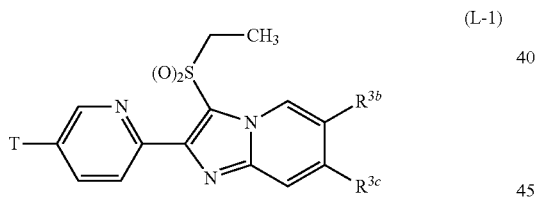

(L-1)

A compound represented by Formula (L-1) (hereinafter referred to as Compound (L-1)) in which $R^{3b}$ and $R^{3c}$ are hydrogen atoms and T is any one of the substituents, described in Tables 1 to 6 (hereinafter referred to as Compound Group SX1).

TABLE 1

$CF_3$
$CHF_2$
$CH_2CF_3$
$CF_2CF_3$
$CH_2CF_2CF_3$
$CF_2CF_2CF_3$
$CF_2CF_2CF_2CF_3$
$CF_2CF_2CF_2CF_2CF_3$
$OCF_3$
$OCF_2CHF_2$
$OCH_2CF_3$
$OCH_2CHF_2$
$OCF_2CF_3$
$OCH(CH_3)CF_3$
$OCH_2CF_2CHF_2$

TABLE 1-continued $OCH_2CF_2CF_3$
$OCF_2CF_2CF_3$
$OCH_2CF_2CHFCF_3$
$OCH_2CF_2CF_2CF_3$
$OCF_2CF_2CF_2CF_3$
$OCH_2CF_2CF_2CF_2CF_3$

TABLE 2

$SCF_3$
$SCH_2CF_3$
$SCF_2CF_3$
$SCH_2CF_2CF_3$
$SCF_2CF_2CF_3$
$SCH_2CF_2CF_2CF_3$
$SCF_2CF_2CF_2CF_3$
$S(O)CF_3$
$S(O)CH_2CF_3$
$S(O)CF_2CF_3$
$S(O)CH_2CF_2CF_3$
$S(O)CF_2CF_2CF_3$
$S(O)CH_2CF_2CF_2CF_3$
$S(O)CF_2CF_2CF_2CF_3$
$S(O)_2CF_3$
$S(O)_2CH_2CF_3$
$S(O)_2CF_2CF_3$
$S(O)_2CH_2CF_2CF_3$
$S(O)_2CF_2CF_2CF_3$
$S(O)_2CH_2CF_2CF_2CF_3$
$S(O)_2CF_2CF_2CF_2CF_3$

TABLE 3

$NHCH_2CF_3$
$NHCH_2CF_2CF_3$
$NHCH_2CF_2CF_2CF_3$
$NMeCH_2CF_3$
$NMeCH_2CF_2CF_3$
$NMeCH_2CF_2CF_2CF_3$
$NEtCH_2CF_3$
$NEtCH_2CF_2CF_3$
$NEtCH_2CF_2CF_2CF_3$
$OS(O)_2CF_3$
$OS(O)_2CF_2CF_3$
$OS(O)_2CF_2CF_2CF_3$
$CH_2OCF_3$
$CH_2OCH_2CF_3$
$CH_2OCF_2CF_3$
$C(O)CF_3$
$C(O)CF_2CF_3$

TABLE 3-continued

C(O)CF$_2$CF$_2$CF$_3$
C(O)NMeCH$_2$CF$_3$
NMeC(O)CF$_3$
N=CEtCH$_2$CF$_3$

TABLE 4

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph

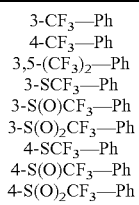

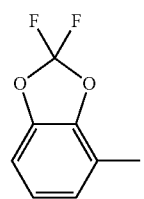

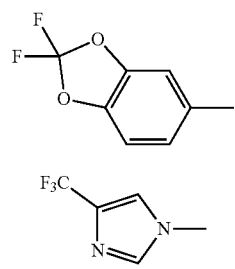

TABLE 5

4—CF$_3$—Py2
5—CF$_3$—Py2
4—SCF$_3$—Py2
4—S(O)CF$_3$—Py2
4—S(O)$_2$CF$_3$—Py2
5—SCF$_3$—Py2
5—S(O)CF$_3$—Py2
5—S(O)$_2$CF$_3$—Py2
5—NMeCH$_2$CF$_3$—Py2

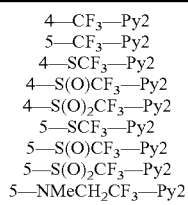

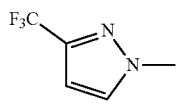

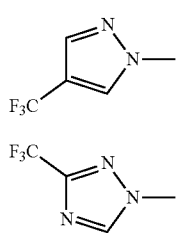

TABLE 6

5—CF$_3$—Py3
6—CF$_3$—Py3

TABLE 6-continued

5—SCF$_3$—Py3
5—S(O)CF$_3$—Py3
5—S(O)$_2$CF$_3$—Py3
6—SCF$_3$—Py3
6—S(O)CF$_3$—Py3
6—S(O)$_2$CF$_3$—Py3
6—NMeCH$_2$CF$_3$—Py3

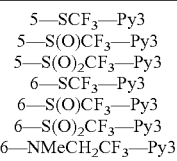

Compound (L-1) in which $R^{3b}$ is a chlorine atom, $R^{3c}$ is a hydrogen atom, and T is any one of the substituents described in Tables 1 to 6 (hereinafter referred to as Compound Group SX2).

Compound (L-1) in which $R^{3b}$ is a trifluoromethyl group, $R^{3a}$ is a hydrogen atom and T is any one of the substituents described in Tables, 1 to 6 (hereinafter referred to as Compound Group SX3).

Compound (L-1) in which $R^{3b}$ is a hydrogen atom, $R^{3c}$ is a chlorine atom, and T is any one of the substituents described in Tables 1 to 6 (hereinafter referred to as Compound Group SX4).

Compound (L-1) in which $R^{3b}$ is a hydrogen atom, $R^{3c}$ is a trifluoromethyl group and T is any one of the substituents described in Tables 1 to 6 (hereinafter referred to as Compound Group SX5).

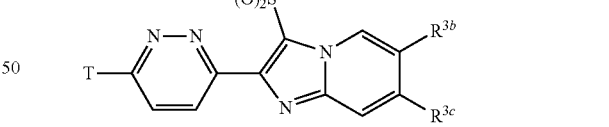

(L-2)

A compound represented by Formula (L-2) (hereinafter referred to as Compound (L-2)) in which $R^{3b}$ and $R^{3c}$ are hydrogen atoms and T is any one of the substituents described in Tables 1 to 6 (hereinafter referred to as Compound Group SX6).

Compound (L-2) in which $R^{3b}$ is a chlorine atom, $R^{3c}$ is a hydrogen atom, and T is any one of the substituents described in Tables 1 to 6 (hereinafter referred to as Compound Group SX7).

Compound (L-2) in which $R^{3b}$ is a trifluoromethyl group, $R^{3c}$ is a hydrogen atom, and T is any one of the substituents described in Tables 1 to 6 (hereinafter referred to as Compound Group SX8).

Compound (L-2) in which $R^{3b}$ is a hydrogen atom, $R^{3c}$ is a chlorine atom, and T is any one of the substituents described in Tables 1 to 6 (hereinafter referred to as Compound Group SX9).

Compound (L-2) in which $R^{3b}$, is a hydrogen atom, $R^{3c}$ is a trifluoromethyl group, and T is any one of the substituents described in Tables 1 to 6 (hereinafter referred to as Compound Group. SX10).

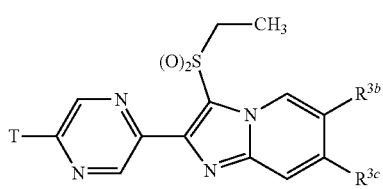

(L-3)

A compound represented by Formula (L-3) (hereinafter referred to as Compound (L-3)) in which $R^{3b}$ and $R^{3c}$ are hydrogen atoms and T is any one of the substituents described in Tables 1 to 6 (hereinafter referred to as Compound Group SX11).

Compound (L-3) in which $R^{3b}$ is a chlorine atom, $R^{3c}$ is a hydrogen atom, and T is any one of the substituents described in Tables 1 to 6 (hereinafter referred to as Compound Group SX12).

Compound (L-3) in which $R^{3b}$ is a trifluoromethyl group, $R^{3c}$ is a hydrogen atom, and T is any one of the substituents described in Tables 1 to 6 (hereinafter referred to as Compound Group SX13).

Compound (L-3) in which $R^{3b}$ is a hydrogen atom, $R^3$ is a chlorine atom, aid T is any one of the substituents described in Tables 1 to 6 (hereinafter referred to as Compound Group SX14).

Compound (L-3) in which $R^{3b}$ is a hydrogen atom, $R^{3c}$ is a trifluoromethyl group, and T is any one of the substituents described in Tables 1 to 6 (hereinafter referred to as Compound Group SX15).

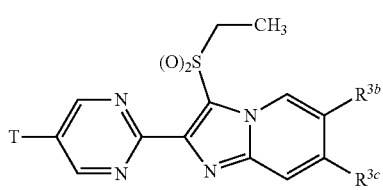

(L-4)

A compound represented by Formula (L-4) (hereinafter referred to as Compound (L-4)) in which $R^{3b}$ and $R^{3c}$ are hydrogen atoms and T is any one of the substituents described in Tables 1 to 6 (hereinafter referred to as Compound Group SX16).

Compound (L-4) in which $R^{3b}$ is a chlorine atom, $R^{3c}$ is a hydrogen atom, and T is any one of the substituents described in Tables 1 to 6 (hereinafter referred to as Compound Group SX17).

Compound (L-4) in which $R^{3b}$ is a trifluoromethyl group $R^{3c}$ is a hydrogen atom, and T is any one of the substituents described in Tables 1 to 6 (hereinafter referred to as Compound Group SX18).

Compound (L-4) in which $R^{3b}$ is a hydrogen atom, $R^{3c}$ is a chlorine atom, and T is any one of the substituents described in Tables 1 to 6 (hereinafter referred to as Compound Group SX19).

Compound (L-4) in which $R^{3b}$ is a hydrogen atom, $R^{3c}$ is a trifluoromethyl group, and T is any one of the substituents described in Tables 1 to 6 (hereinafter referred to as Compound Group SX20),

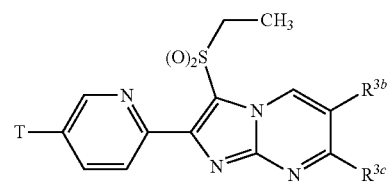

(L-5)

A compound represented by Formula (L-5) (hereinafter referred to as Compound (L-5)) in WHICH $R^{3b}$ and $R^{3C}$ are hydrogen atoms and T is any one of the substituents described in Tables 1 to 6 (hereinafter referred to as Compound Group SX21).

Compound (L-5) in which $R^{3b}$ is 8a chlorine atom, $R^{3C}$ is a hydrogen atom, and T is any one of the substituents described in Tables 1 to 6 (hereinafter referred to as Compound Group SX22).

Compound (L-5) in which $R^{3b}$ is a trifluoromethyl group, $R^{3c}$ is a hydrogen atom, and T is any one of the substituents described in Tables 1 to 6 (hereinafter referred to as Compound Group SX23).

Compound (L-5) in which $R^{3b}$ is a hydrogen atom, $R^{3c}$ is a chlorine atom, and T is any one of the substituents described in Tables 1 to 6 (hereinafter referred to as Compound Group SX24).

Compound (L-5) in which $R^{3b}$ is a hydrogen atom, $R^{3c}$ is a trifluoromethyl group, and T is any one of the substituents described in Tables 1 to 6 (hereinafter referred to as Compound Group SX25).

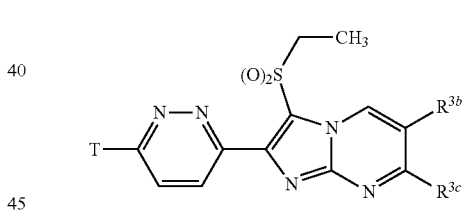

(L-6)

A compound represented by Formula (L-6) (hereinafter referred to as Compound (L-6)) in which $R^{3b}$ and $R^{3c}$ are hydrogen atoms and T is any one of the substituents described in Tables 1 to 6'(hereinafter referred to as Compound Group SX26).

Compound (L-6) in which $R^{3b}$ is a chlorine atom, $R^{3c}$ is a hydrogen atom, and T is any one of the substituents described in Tables 1 to 6 (hereinafter referred to as Compound Group SX27).

Compound (L-6) in which $R^{3b}$ is a trifluoromethyl group, $R^{3c}$ is a hydrogen atom, and T is any one of the substituents described in Tables 1 to 6 (hereinafter referred to as Compound Group SX28).

Compound (L-6) in which $R^{3b}$ is a hydrogen atom $R^{3c}$ is a chlorine atom, and T is any one of the substituents described in Tables 1 to 6 (hereinafter referred to as Compound Group SX29).

Compound (L-6) in which $R^{3b}$ is a hydrogen atom, $R^{3c}$ is a trifluoromethyl group, and T is any one of the substituents described in Tables L to 6 (hereinafter referred to as Compound Group SX30).

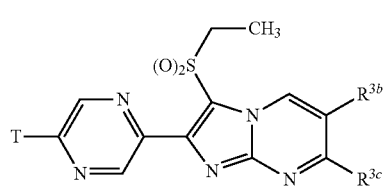
(L-7)

A compound represented by Formula (L-7) (hereinafter referred to as Compound (L-7)) in which $R^{3b}$ and $R^{3c}$ are hydrogen atoms, and T is any one of the substituents described in Tables 1 to 6 (hereinafter referred to as Compound Group SX3).

Compound (L-7) in which $R^{3b}$ is a chlorine atom, $R^{3c}$ is a hydrogen atom, and T is any one of the substituents described in Tables 1 to 6 (hereinafter referred to as Compound Group SX32).

Compound (L-7) in which $R^{3b}$ is a trifluormethyl group, $R^{3c}$ is a hydrogen atom; and T is any one of the substituents described in Tables 1 to 6 (hereinafter referred to as Compound Group SX33), Compound (L-7) in which $R^{3b}$ is a hydrogen atom, $R^{3c}$ is a chlorine atom, and T is any one of the substituents described in Tables 1 to 6 (hereinafter referred to as Compound Group SX34).

Compound (L-7) in which $R^{3b}$ is a hydrogen atom, $R^{3c}$ is a trifluoromethyl group, and T is any one of the substituents described in Tables 1 to 6 (hereinafter referred to as Compound Group SX35).

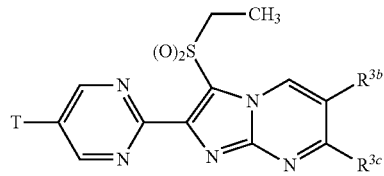
(L-8)

A compound represented by Formula (L-8) (hereinafter referred to as Compound (L-8)) in which $R^{3b}$ and $R^{3c}$ are hydrogen atoms and T is any one of the substituents described in Tables 1 to 6 (hereinafter referred to as Compound Group SX36).

Compound (L-8) in which $R^{3b}$ is a chlorine atom, $R^{3c}$ is a hydrogen atom, and T is any one of the substituents described in Tables 1 to 6 (hereinafter referred to as Compound Group SX37).

Compound (L-8) in which $R^{3b}$ is a trifluoromethyl group, $R^{3C}$ is a hydrogen atom, and T is any one of the substituents described in Tables 1 to 6 (hereinafter referred to as Compound Group SX38).

Compound (L-8) in which $R^{3b}$ is a hydrogen atom, $R^{3c}$ is a chlorine atom, and T is any one of the substituents described in Tables 1 to 6 (hereinafter referred to as Compound Group SX39).

Compound (L-8) in which $R^{3b}$ is a hydrogen atom, $R^{3c}$ is a trifluoromethyl group, and T is any one of the substituents described in Tables 1 to 6 (hereinafter referred to as Compound Group SX40).

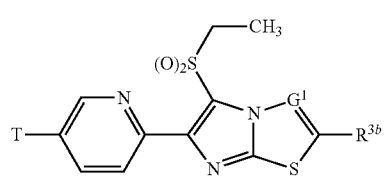
(L-9)

A compound represented by Formula (L-9) (hereinafter referred to as Compound (L-9)) in which $G^1$ is CH, $R^{3b}$ is a hydrogen atom, and T is any one of the substituents described in Tables 1 to 6 (hereinafter referred to as Compound Group SX41).

Compound (L-9) in which $G^1$ is CH, $R^{3b}$ is a trifluoromethyl group, and T is any one of the substituents described in Tables 1 to 6 (hereinafter referred to as Compound Group SX42).

Compound (L-9) in which $G^1$ is a nitrogen atom, $R^{3b}$ is a hydrogen atom, and T is any one of the substituents described in Tables 1 to 6 (hereinafter referred to as Compound Group SX43).

Compound (L-9) in which $G^1$ is a nitrogen atom, $R^{3b}$ is a trifuoromethyl group, and T is any one of the substituents described in Tables 1 to 6 (hereinafter referred to as Compound Group SX44).

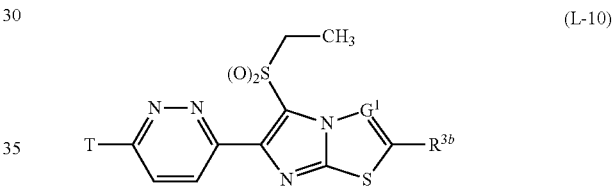
(L-10)

A compound represented by Formula (L-10) (hereinafter referred to as Compound (L-10)) in which $G^1$ is CH, $R^{3b}$ is a hydrogen atom and T is any one of the substituents described in Tables 1 to 6 (hereinafter referred to as Compound Group SX45).

Compound (L-10) in which $G^1$ is CH, $R^{3b}$ is a trifluoromethyl group, and T is, any one of the substituents described in Tables 1 to 6 (hereinafter referred to as Compound Group. SX46).

Compound (L-10) in which $G^1$ is a nitrogen atom, $R^{3b}$ is a hydrogen atom and T is any one of the substituents described in Tables 1 to 6 (hereinafter referred to as Compound Group SX47).

Compound (L-10) in which $G^1$ is a nitrogen atom, $R^{3b}$ is a trifluoromethyl group, and T is any one of the substituents described in Tables 1 to 6 (hereinafter referred to as Compound Group SX48).

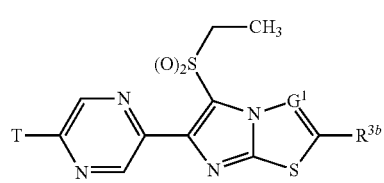
(L-11)

A compound represented by Formula (L-11) (hereinafter referred to as Compound (L-11)) in which $G^1$ is CH, $R^{3b}$ is a hydrogen atom, and T is any one of the substituents described in Tables 1 to 6 (hereinafter referred to as Compound Group SX49).

Compound (L-11) in which $G^1$ is CH, $R^{3b}$ is a trifluoromethyl group, and T is any one of the substituents described in Tables 1 to 6 (hereinafter referred to as Compound Group SX50).

Compound (L-11) in which $G^1$ is a nitrogen atom, $R^{3b}$ is a hydrogen atom, and T is any one of the substituents described in Tables 1 to 6 (hereinafter referred to as Compound Group SX51).

Compound (L-11) in which $G^1$ is a nitrogen atom, $R^{3b}$ is a trifluoromethyl group, and T is any one of the substituents described in Tables 1 to 6 (hereinafter referred to as Compound Group SX52).

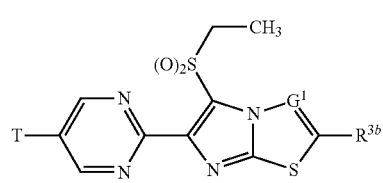

A compound represented by Formula (L-12) (hereinafter referred to as Compound (L-12)) in which G is CH, $R^{3b}$ is a hydrogen atoms and T is any one of the substituents described in Tables 1 to 6 (hereinafter referred to as Compound Group SX53).

Compound (L-12) in which $G^1$ is CH, $R^{3b}$ is a trifluoromethyl group, and T is any one of the substituents described in Tables 1 to 6 (hereinafter referred to as Compound Group SX54).

Compound (L-12) in which $G^1$ is a nitrogen atom, $R^{3b}$ is a hydrogen atom, and T is any one of the substituents described in Tables 1 to 6 (hereinafter referred to as Compound Group SX55).

Compound (L-12) in which $G^1$ is a nitrogen atom, $R^{3b}$ is a trifluoromethyl group, and T is any one of the substituents described in Tables 1 to 6 (hereinafter referred to as Compound Group SX56).

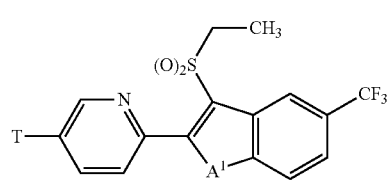

A compound represented by Formula (L-13) (hereinafter referred to as Compound (L-13)) in which $A^1$ is N—CH$_3$ and T is any one of the substituents described in Tables 1 to 6 (hereinafter referred to as Compound Group SX57).

Compound (L-13) in which $A^1$ is a sulfur atom and T is any one of the substituents described in Tables 1 to 6 (hereinafter referred to as Compound Group SX58).

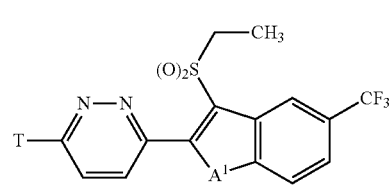

A compound represented by Formula (L-14) (hereinafter referred to as Compound (L-14)) in which $A^1$ is N—CH$_3$ and T is any one of the substituents described in Tables 1 to 6 (hereinafter referred to as Compound Group SX59).

Compound (L-14) in which $A^1$ is a sulfur atom and T is any one of the substituents described in Tables 1 to 6 (hereinafter referred to as Compound Group SX60).

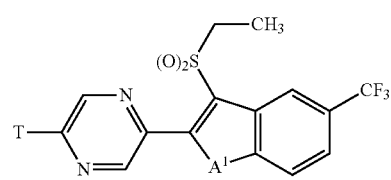

A compound represented by Formula (L-15) (hereinafter referred to as Compound (L-15)) in which $A^1$ is N—CH$_3$ and T is any one of the substituents described in Tables 1 to 6 (hereinafter referred to as Compound Group SX61).

Compound (L-15), in which $A^1$ is a sulfur atom and T is any one of the substituents described in Tables 1 to 6 (hereinafter referred to as Compound Group SX62).

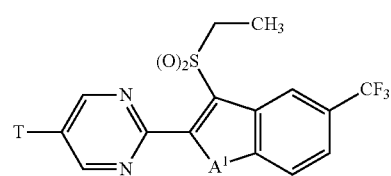

A compound represented by Formula (L-16) (hereinafter referred to as Compound (L-16)) in which $A^1$, is N—CH$_3$ and T is any one of the substituents described in Tables 1 to 6 (hereinafter referred to as Compound Group SX63), Compound (L-16) in which $A^1$ is a sulfur atom and T is any one of the substituents described in Tables 1 to 6 (hereinafter referred to as Compound Group SX64).

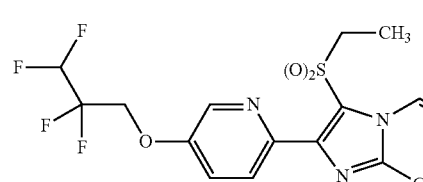

A compound represented by Formula (L-17) (hereinafter referred to as Compound (L-17)) in which $G^4$ is CH, $R^{3b}$ is a hydrogen atom, and $R^{3c}$ is any one of the substituents described in Tables 7 to 15 (hereinafter referred to as Compound Group SX65).

TABLE 7

F
Cl
Br
Me
Et
Pr
i-Pr
c-Pr
1-CN-c-Pr
OMe
OEt
OPr
Oi-Pr
CF$_3$
NH$_2$
NHCH$_2$CF$_3$
CN
C(O)OEt
NHC(O)c-Pr
NMeC(O)c-Pr
CH=N—OH
CH=N—OMe
CH=N—OEt
CH=N—OCH$_2$CF$_3$
CMe=N—OH
CMe=N—OMe
CMe=N—OEt
CMe=N—OCH$_2$CF$_3$
C(NH$_2$)=N—OCH$_2$CF$_3$

TABLE 8

Ph
3-F—Ph
4-F—Ph
3-Cl—Ph
4-Cl—ph
3-CF$_3$—Ph
4-CF$_3$—Ph
3-NMe$_2$—Ph
4-NMe$_2$—Ph
3-CN—Ph
4-CN—Ph
4-C(O)NMe$_2$—Ph
4-NHC(O)Me—Ph
3,4-F$_2$—Ph
3,5-F$_2$—Ph
2,4-F$_2$—Ph
3,4,5-F$_3$—Ph
3,4-Cl$_2$—Ph
3,5-Cl$_2$—Ph
3,5-Cl$_2$-4-F—Ph
OPh
O-2-F—Ph
OPy2
OPy3

TABLE 9

Py2
4-F—Py2
5-F—Py2
4-Cl—Py2
5-Cl—Py2
4-CF$_3$—Py2
5-CF$_3$—Py2
3-Me—Py2
4-Me—Py2
5-Me—Py2
6-Me—Py2
5-CN—Py2
5-OCH$_2$CF$_2$CF$_3$—Py2
3,5-F$_2$-Py2
Py3
6-CF$_3$—Py3

TABLE 9-continued

5-CF$_3$—Py3
6-F—Py3
6-Cl—Py3
Py4

TABLE 10

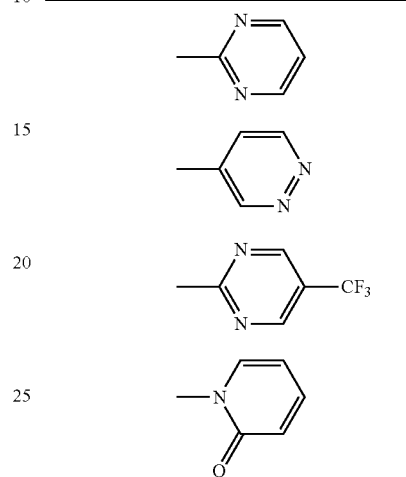

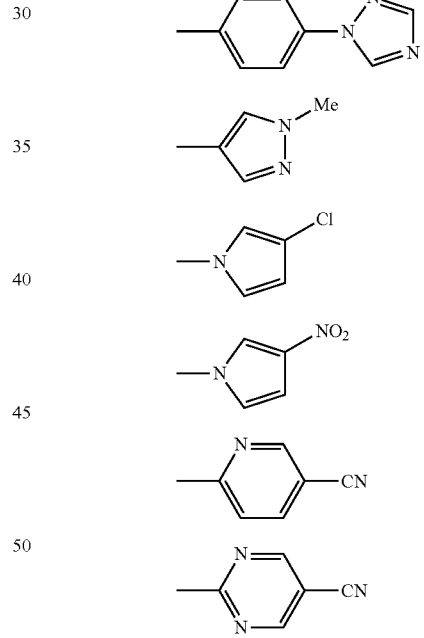

TABLE 11

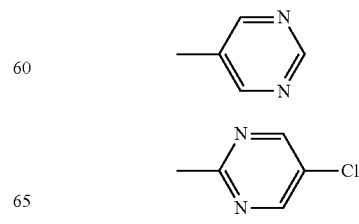

TABLE 11-continued
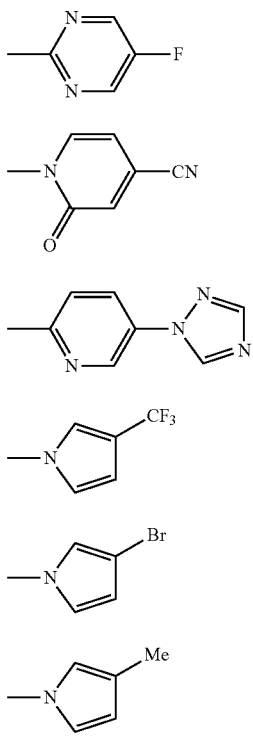
TABLE 12
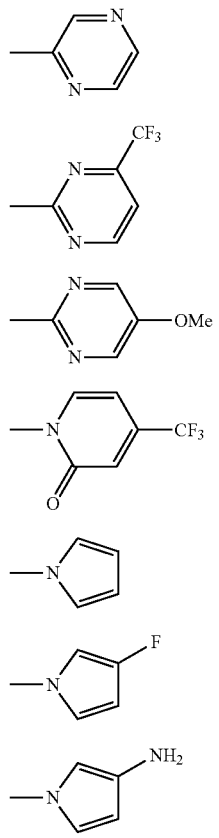
TABLE 12-continued
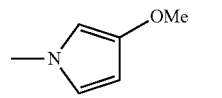
TABLE 13
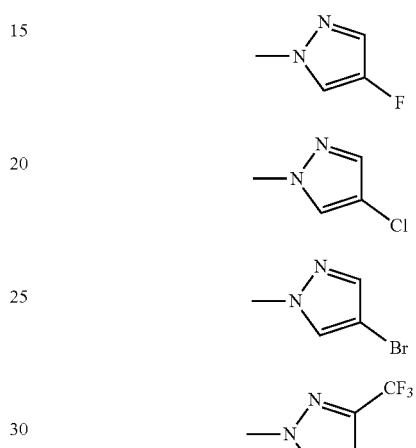
TABLE 14
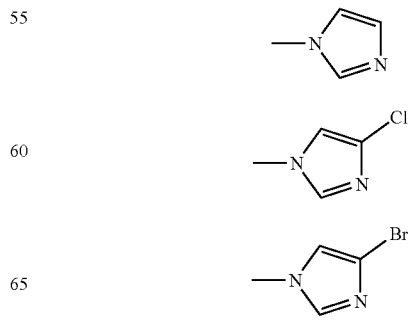

TABLE 14-continued

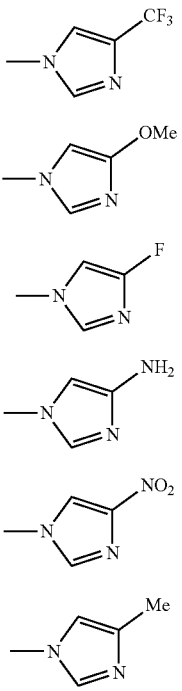

TABLE 15

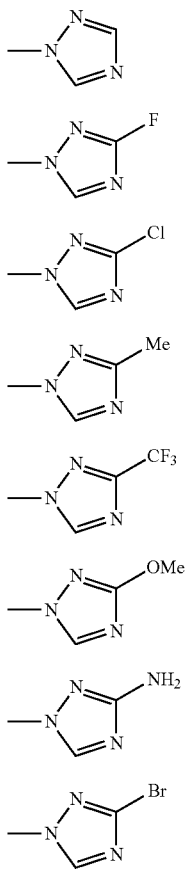

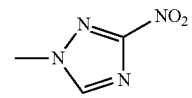

Compound (L-17) in which $G^4$ is CH, $R^{3c}$ is a hydrogen atom, and $R^{3b}$ is ally one of the substituents described in Tables 7 to 15 (hereinafter referred to as Compound Group SX66), Compound (L-17) in which $G^4$ is a nitrogen atom, $R^b$ is a hydrogen atom; and $R^{3c}$ is any one of the substituents described in Tables 7 to 15 (hereinafter referred to as Compound Group SX67).

Compound (L-17) in which $G^4$ is a nitrogen atom, $R^{3c}$ is a hydrogen atom, and $R^{3b}$ is any one of the substituents described in Tables 7 to 15 (hereinafter referred to as Compound Group SX68).

(L-18)

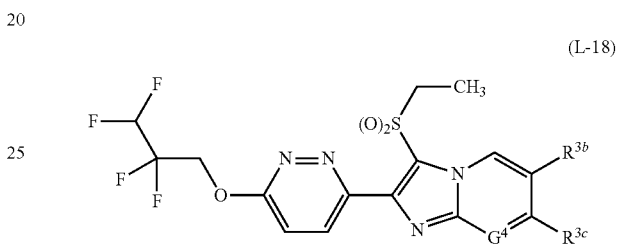

A compound represented by Formula (L-18) (hereinafter referred to as Compound (L-48)) in which $G^4$ is CH, $R^{3b}$ is a hydrogen atom and $R^{3c}$ is any one of the substituents described in Tables 7 to 15 (hereinafter referred to as Compound Group SX69).

Compound (L-18) in which $G^4$ is CH, $R^{3c}$ is a hydrogen atom, and $R^{3b}$ is any one of the substituents described in Tables 7 to 15 (hereinafter referred to as Compound Group SX70).

Compound (L-18) in which $G^4$ is a nitrogen atom, $R^{3b}$ is a hydrogen atom, and $R^{3c}$ is any one of the substituents described in Tables 7 to 15 (hereinafter referred to as Compound Group SX71).

Compound (L-18) in which $G^4$ is a nitrogen atom, $R^{3c}$ is a hydrogen atom, and $R^{3b}$ is any one of the substituents described in Tables 7 to 15 (hereinafter referred to as Compound Group SX72).

(L-19)

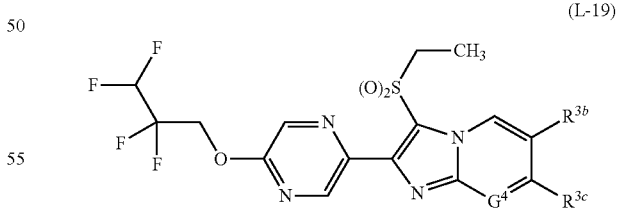

A compound represented by Formula (L-19) (hereinafter referred to as Compound (L-19)) in which $G^4$ is CH, $R^A$ is a hydrogen atom, and $R^{3e}$ is any one of the substituents described in Tables 7 to 15 (hereinafter referred to as Compound Group SX73).

Compound (L-19) in which $G^4$ is CH, $R^{3c}$ is a hydrogen atom, and $R^{3b}$ is any one of the substituents described in Tables 7 to 15 (hereinafter referred to as Compound Group SX74).

Compound (L-19) in which G⁴ is a nitrogen atom, R³ᵇ is a hydrogen atom, and R³ᶜ is any one of the substituents described in Tables 7 to 15 (hereinafter referred to as Compound Group SX75):

Compound (L-19) in which G⁴ is a nitrogen atom, R³ᶜ is a hydrogen atom, and R³ᵇ is any one of the substituents described in Tables 7 to 15 (hereinafter referred to as Compound Group SX76).

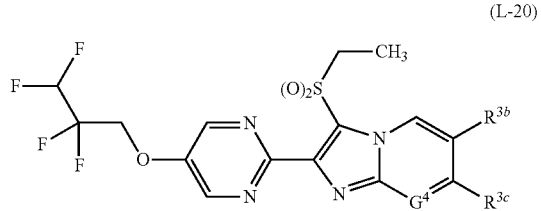
(L-20)

A compound represented by Formula (L-20) (hereinafter referred to as Compound (L-20)) in which G⁴ is CH, R³ᵇ is a hydrogen atom, and R³ᶜ is any one of the substituents described in Tables 7 to 15 (hereinafter referred to as Compound Group SX77).

Compound (L-20), in which G⁴ is CH R³ᶜ is a hydrogen atom, and R³ᵇ is any one of the substituents described in Tables 7 to 15 (hereinafter referred to as Compound Group SX78).

Compound (L-20) in which G⁴ is a nitrogen atom, R³ᵇ is a hydrogen atom, and R³ᶜ is any one of the substituents described in Tables 7 to 15 (hereinafter referred to as Compound Group SX79).

Compound (L-20) in which G⁴ is a nitrogen atom, R³ᶜ is a hydrogen atom, and R³ᵇ is any one of the substituents described in Tables 7 to 15 (hereinafter referred to as Compound Group SX80).

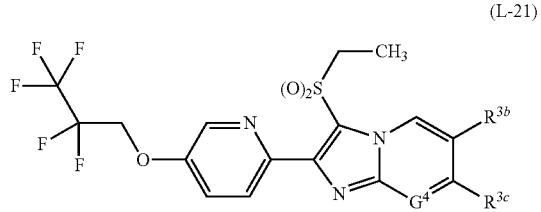
(L-21)

A compound represented by Formula (L-21) (hereinafter referred to as Compound (L-21)) in which G⁴ is CH, R³ᵇ is a hydrogen atom, and R³ᵉ is any one of the substituents described in Tables 7 to 15 (hereinafter referred to as Compound Group SX81).

Compound (L-21) in which, G⁴ is CH, R is a hydrogen atom, and R³ᵇ is any one of the substituents described in Tables 7 to 15 (hereinafter referred to as Compound Group SX82).

Compound (L-21) in which G, is a nitrogen atom, R³ᵇ is a hydrogen atom, and R³ᶜ a is any one of the substituents described in Tables 7 to 15 (hereinafter referred to as Compound Group SX83).

Compound (L-21) in which G⁴ is a nitrogen atom, R³ᶜ is a hydrogen atom, and R³ᵇ is any one of the substituents described in Tables 7 to 15 (hereinafter referred to as Compound Group SX84).

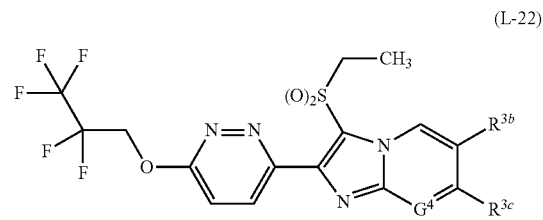
(L-22)

A compound represented by Formula (L-22) (hereinafter referred to as Compound (L-22)) in which G⁴ is CH, R³ᵇ is a hydrogen atom, and R³ᶜ is any one of the substituents described in Tables 7 to 15 (hereinafter referred to as Compound Group SX85):

Compound (L-22) in which G⁴ is CH, R³ᶜ is a hydrogen atom, and R³ᵇ is any one of the substituents described in Tables 7 to 15 (hereinafter referred to as Compound Group SX86).

Compound (L-22) in which G is a nitrogen atom, R³ᵇ is a hydrogen atom, and R³ᶜ is any one of the substituents described in Tables 7 to 15 (hereinafter referred to as Compound Group SX87), Compound (L-22) in which, G⁴ is a nitrogen atom, R³ᶜ is a hydrogen atom, and R³ᵇ is anyone of the substituents described in Tables 7 to 15 (hereinafter referred to as Compound Group SX88).

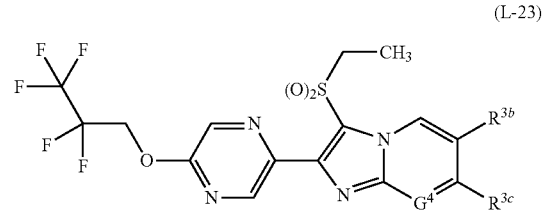
(L-23)

A compound-represented by Formula (L-23) (hereinafter referred to as Compound (L-23)) in which G⁴ is CH, R³ᵇ is a hydrogen atom, and R³ᶜ is any one of the substituents described in Tables 7 to 15 (hereinafter referred to as Compound Group SX89).

Compound (L-23) in which G⁴ is CH, R³ᶜ is a hydrogen atom, and R³ᵇ is any one of the substituents described in Tables 7 to 15 (hereinafter referred to as Compound Group SX90), Compound (L-23) in which G⁴ is a nitrogen atom, R³ᵇ is a hydrogen atom, and R³ᶜ is any one of the substituents described in Tables 7 to 15 (hereinafter referred to as Compound Group SX91).

Compound (L-23) in which, G⁴ is a nitrogen atom R³ᶜ is a hydrogen atom, and R³ᵇ is any one of the substituents described in Tables 7 to 15 (hereinafter referred to as Compound Group SX92).

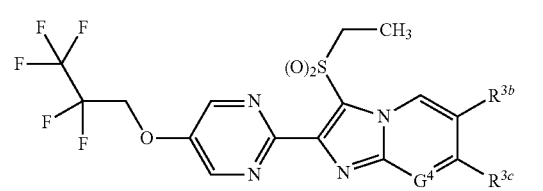
(L-24)

A compound represented by Formula (L-24)(hereinafter referred to as Compound (L-24)) in which G is CH, $R^{3b}$ is a hydrogen atom, and $R^{3c}$ is any one of the substituents described in Tables 7 to 15 (hereinafter referred to as Compound Group SX93).

Compound (L-24) in which $G^4$ is CH, $R^{3c}$ is a hydrogen atom, and $R^{3b}$ is any one of the substituents described in Tables 7 to 1.5 (hereinafter referred to as Compound Group SX94).

Compound (L-24) in which $G^4$ is a nitrogen atom, $R^{3b}$ is a hydrogen atom, and $R^{3c}$ is any one of the substituents described in Tables 7 to 15 (hereinafter referred to as Compound Group SX95), Compound (L-24) in which $G^4$ is a nitrogen atom, $R^{3c}$ is a hydrogen atom, and $R^{3b}$ is any one of the substituents described in Tables 7 to 15 (hereinafter referred to as Compound Group SX96).

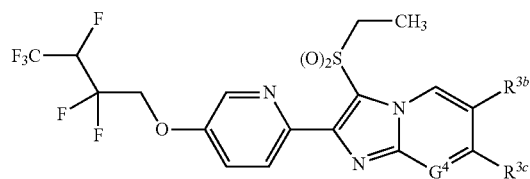

(L-25)

A compound represented by Formula (L-25) (hereinafter referred to as Compound (L-25)) in which $G^4$ is CH, $R^{3b}$ is a hydrogen atom; and $R^{3c}$ is any one of the substituents described in Tables 7 to 15 (hereinafter referred to as Compound Group SX97).

Compound (L-25) in which $G^4$ is CH, $R^{3c}$ is a hydrogen atom, and $R^{3b}$ is any one of the substituents described in Tables 7 to 15 (hereinafter referred to as Compound Group SX98).

Compound (L-25) in which $G^4$ is a nitrogen atom, $R^{3b}$ is a hydrogen atom, and $R^{3c}$ is any one of the substituents described in Tables 7 to 15 (hereinafter referred to as Compound Group SX99).

Compound (L-25) in which $G^4$ is a nitrogen atom, $R^{3c}$ is a hydrogen atom, and $R^{3b}$ is anyone of the substituents described in Tables 7 to 15 (hereinafter referred to as Compound Group SX100),

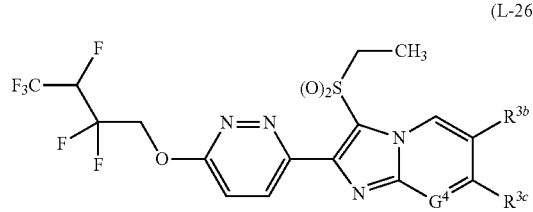

(L-26)

A compound represented by Formula (L-26) (hereinafter, referred to as Compound (L-26)) in which $G^4$ is CH, $R^{3b}$ is a hydrogen atom, and $R^{3c}$ is any one of the substituents described in Tables 7 to 15 (hereinafter referred to as Compound Group SX101).

Compound (L-26) in which $G^4$ is CH, $R^{3c}$ is a hydrogen atom, and $R^{3b}$ is any one of the substituents described in Tables 7 to 15 hereinafter referred to as Compound Group SX102).

Compound (L-26) in which $G^4$ is a nitrogen atom, $R^{3b}$ is a hydrogen atom, and $R^{3c}$ is any one of the substituents described in Tables 7 to 15 (hereinafter referred to as Compound Group SX103).

Compound (L-26) in which $G^4$ is a nitrogen atom, $R^{3c}$ is a hydrogen atom, and $R^{3b}$ is any one of the substituents described in Tables 7 to 15 (hereinafter referred to as Compound Group SX104).

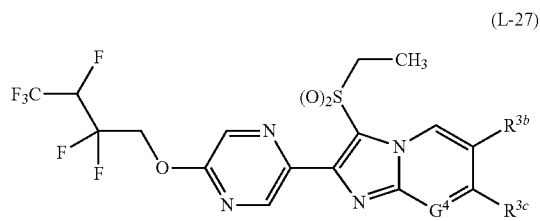

(L-27)

A compound represented by Formula (L-27) (hereinafter referred to as Compound (L-27)) in which $G^4$ is CH, $R^{3b}$ is a hydrogen atom, and $R^{3c}$ is any one of the substituents described in Tables 7 to 15 (hereinafter referred to as Compound Group SX105).

Compound (L-27) in which $G^4$ is CH, $R^{3c}$ is a hydrogen atom, and $R^{3b}$ is any one of the substituents described in Tables 7 to 15 (hereinafter referred to as Compound Group SX106).

Compound (L-27) in which $G^4$ is a nitrogen atom, $R^{3b}$ is a hydrogen atom and $R^{3c}$ is any one of the substituents described in Tables 7 to 15 (hereinafter referred to as Compound Group SX107).

Compound (L-27) in which $G^4$ is a nitrogen atom $R^{3c}$ is a hydrogen atom, and $R^{3b}$ is any one of the substituents described in Tables 7 to 15 (hereinafter referred to as Compound Group SX108),

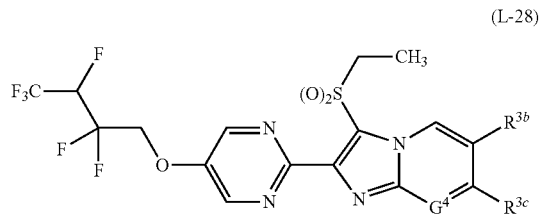

(L-28)

A compound represented by Formula (L-28) (hereinafter referred to as Compound (L-28)) in which $G^4$ is CH, $R^{3b}$ is a hydrogen atom, and $R^{3c}$ is any one of the substituents described in Tables 7 to 15 (hereinafter referred to as Compound Group SX109).

Compound (L-28) in which, $G^4$ is CH, $R^{3c}$ is a hydrogen atom, and $R^{3b}$ is anyone of the substituents described in Tables 7 to 1:5 (hereinafter referred to as Compound Group SX110).

Compound (L-28) in which $G^4$ is a nitrogen atom, $R^{3b}$ is a hydrogen atom, and $R^{3c}$ is any one of the substituents described in Tables 7 to 15 (hereinafter referred to as Compound Group SX111).

Compound (L-28) in which $G^4$ is a nitrogen atom, $R^{3c}$ is a hydrogen atom, and $R^{3b}$ is any one of the substituents described in Tables 7 to 15 (hereinafter referred to as Compound Group SX112).

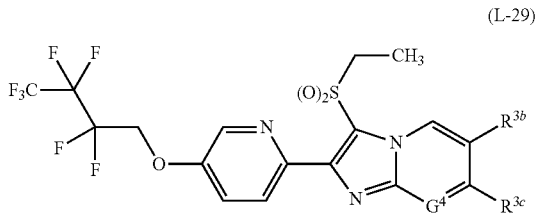
(L-29)

A compound represented by Formula (L-29) (hereinafter referred to as Compound (L-29)) in which $G^4$ is CH, $R^{3b}$ is a hydrogen atom, and $R^{3c}$ is any one of the substituents described in Tables 7 to 15 (hereinafter referred to as Compound Group SX113).

Compound (L-29) in which $G^4$ is CH, $R^{3c}$ is a hydrogen atom, and $R^{3b}$ is any one of the substituents described in Tables, 7 to 15 (hereinafter referred to as Compound Group SX114).

Compound (L-29) in which, $G^4$ is a nitrogen atom, $R^{3b}$ is a hydrogen atom, and $R^{3c}$ is any one of the substituents described in Tables 7 to 15 (hereinafter referred to as Compound Group SX115).

Compound (L-29) in which $G^4$ is a nitrogen atom, $R^{3c}$ is a hydrogen atom, and $R^{3b}$ is any one of the substituents described in Tables 7 to 15 (hereinafter referred to as Compound Group SX116),

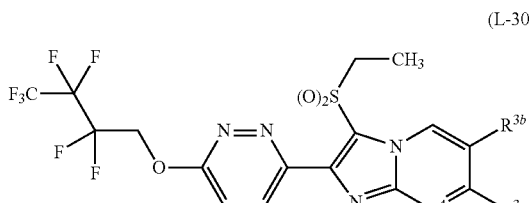
(L-30)

A compound represented by Formula (L-30) (hereinafter referred to as Compound (L-30)) in which $G^4$ is CH, $R^{3c}$ is a hydrogen atom, and $R^{3b}$ is any one of the substituents described in Tables 7 to 15 (hereinafter referred to as Compound Group SX117), Compound (L-30) in which $G^4$ is CH, $R^{3c}$ is a hydrogenator and $R^{3b}$ is any one of the substituents described in Tables 7 to 15 (hereinafter referred to as Compound Group SX118), Compound (L-30) in which $G^4$ is a nitrogen atom, $R^{3b}$ is a hydrogen atom, and $R^{3c}$ is any one of the substituents described in Tables 7 to 15 (hereinafter referred to as Compound Group SX19).

Compound (L-30) in which $G^4$ is a nitrogen atom, $R^{3c}$ is a hydrogen atom, and $R^{3b}$ is any one of the substituents described in Tables 7 to 15 (hereinafter referred to as Compound Group SX120),

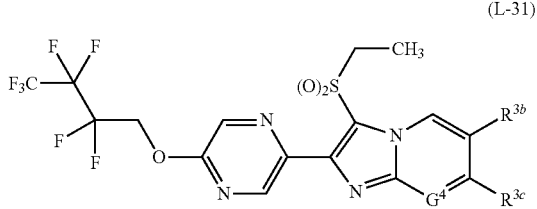
(L-31)

A compound represented by Formula (L-31) (hereinafter referred to as Compound (L-31)) in which G is CH, $R^{3b}$ is a hydrogen atom, and $R^{3c}$ is anyone of the substituents described in Tables 7 to 15 (hereinafter referred to as Compound Group SX121).

Compound (L-31) in which $G^4$ is CH, $R^{3c}$ is a hydrogen atom, and $R^{3b}$ is any one of the substituents described in Tables 7 to 15 (hereinafter referred to as Compound Group SX122).

Compound (L-31) in which $G^4$ is a nitrogen atom, $R^{3b}$ is a hydrogen atom, and $R^{3c}$ is any one of the substituents described in Tables 7 to 15 (hereinafter referred to as Compound Group SX123):

Compound (L-31) in which $G^4$ is a nitrogen atom, $R^{3c}$ is a hydrogen atom, and $R^{3b}$ is any one of the substituents described in Tables 7 to 15 (hereinafter referred to as Compound Group SX124).

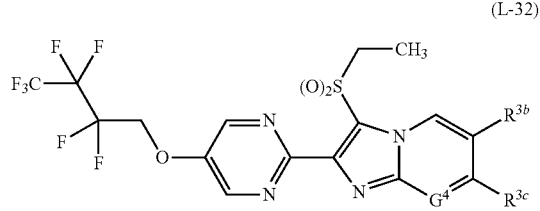
(L-32)

A compound represented by Formula (L-32) (hereinafter referred to as Compound (L-32)) in which $G^4$ is CH, $R^{3b}$ is a hydrogen atom, and $R^{3c}$ is any one of the substituents described in Tables 7 to 15 (hereinafter referred to as Compound Group SX125):

Compound (L-32) in which $G^4$ is CH, $R^{3c}$ is a hydrogen atom, and $R^{3b}$ is any one of the substituents described in Tables 7 to 15 (hereinafter referred to as Compound Group SX126).

Compound (L-32) in which $G^4$ is a nitrogen atom, $R^{3b}$ is a hydrogen atom and $R^{3c}$ is any one of the substituents described in Tables 7 to 15 (hereinafter referred to as Compound Group SX127):

Compound (L-32) in which $G^4$ is a nitrogen atom $R^{3c}$ is a hydrogen atom and $R^{3b}$ is any one of the substituents described in Tables 7 to 15 (hereinafter referred to as Compound Group SX128).

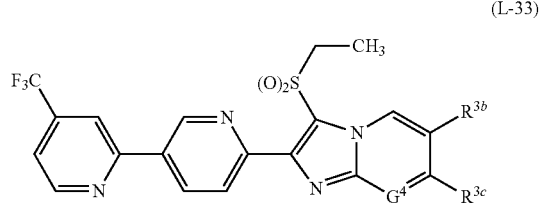
(L-33)

A compound represented by Formula, (L-33) (hereinafter referred to as Compound (L-33)) in which $G^4$ is CH, $R^{3b}$ is a hydrogen atom, and $R^{3c}$ is any one of the substituents described in Tables 7 to 15 (hereinafter referred to as Compound Group SX129).

Compound (L-33) in which $G^4$ is CH, $R^{3c}$ is a hydrogen atom, and $R^{3b}$ is any one of the substituents described in Tables 7 to 15 (hereinafter referred to as Compound Group SX130).

Compound (L-33) in which $G^4$ is a nitrogen atom, $R^{3b}$ is a hydrogen atom, and $R^{3c}$ is any one of the substituents described in Tables 1 to 15. (hereinafter, referred to as Compound Group SX131).

Compound (L-33) in which $G^4$ is a nitrogen atom, $R^{3c}$ is a hydrogen atom, and $R^{3b}$ is any one of the substituents described in Tables 7 to 15 (hereinafter referred to as Compound Group SX132).

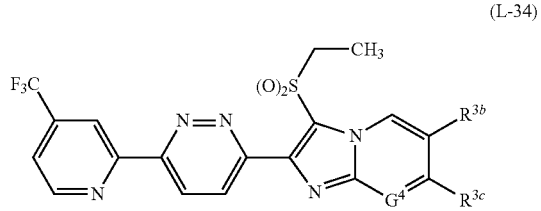
(L-34)

A compound represented by Formula (L-34) (hereinafter referred to as Compound (L-34)) in which $G^4$ is CH, $R^{3b}$ is a hydrogen atom, and $R^{3c}$ is any one of the substituents described in Tables 7 to 15 (hereinafter, referred to as Compound Group SX133).

Compound (L-34) in which $G^4$ is CH, $R^{3c}$ is a hydrogen atom, and $R^{3b}$ is any one of the substituents described in Tables 7 to 15 (hereinafter referred to as Compound Group SX134).

Compound (L-34), in which $G^4$ is a nitrogen atom, $R^{3b}$ is a hydrogen atom; and $R^{3c}$ is any one of the substituents described in Tables 7 to 15 (hereinafter referred to as Compound Group SX35).

Compound (L-34) in which G is a nitrogen atom, $R^{3c}$ is a hydrogen atom, and $R^{3b}$ is anyone of the substituents described in Tables 7 to 15 (hereinafter referred to as Compound Group SX136).

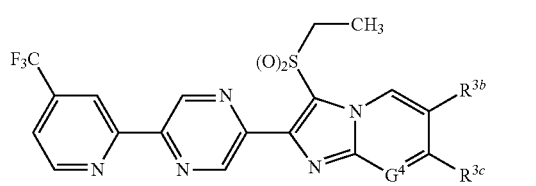
(L-35)

A compound represented by Formula (L-35) (hereinafter referred to as Compound (L-35)) in which $G^4$ is CH, $R^{3b}$ is a hydrogen atom, and $R^{3c}$ is any one of the substituents described in Tables 7 to 15 (hereinafter referred to as Compound Group SX137).

Compound (L-35) in which $G^4$ is CH, $R^{3c}$ is a hydrogen atom, and $R^{3b}$ is any one of the substituents described in Tables 7 to 15 (hereinafter referred to as Compound Group SX138).

Compound (L-35) in which $G^4$ is a nitrogen atom, $R^{3b}$ is a hydrogen atom, and $R^{3c}$ is any one of the substituents described in Tables 7 to 15 (hereinafter referred to as Compound Group SX139).

Compound (L-35) in which $G^4$ is a nitrogen atom, $R^{3c}$ is a hydrogen atom, and $R^{3b}$ is any one of the substituents- described in Tables 7 tot 15 (hereinafter referred to as Compound Group SX140).

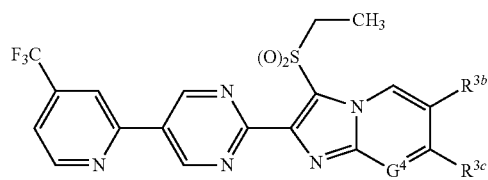
(L-36)

A compound represented by Formula (L-36) (hereinafter referred to as Compound (L-36)) in which $G^4$ is CH, $R^{3b}$ is a hydrogen atom, and $R^{3c}$ is any one of the substituents described in Tables 7 to 15 (hereinafter referred to as Compound Group SX141).

Compound (L-36) in which $G^4$ is CH $R^{3c}$ is a hydrogen atom, and $R^{3b}$ is any one of the substituents described in Tables 7 to 15 (hereinafter referred to as Compound Group SX142).

Compound (L-36) in which $G^4$ is a nitrogen atom $R^{3b}$ is a hydrogen atom, and $R^{3c}$ is any one of the substituents described in Tables 7 to 15 (hereinafter referred to as Compound Group SX143).

Compound (L-36) in which $G^4$ is a nitrogen atom, $R^{3b}$ is a hydrogen atom, and $R^{3b}$ is any one of the substituents described in Tables 7 to 15 (hereinafter referred to as Compound Group SX144).

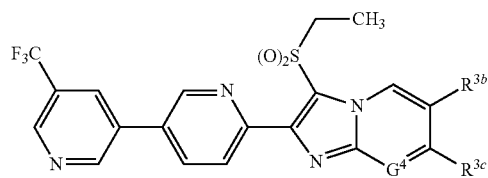
(L-37)

A compound represented by Formula (L-37) (hereinafter referred to as Compound (L-37)) in which $G^4$ is CH, $R^{3b}$ is a hydrogen atom and $R^{3c}$ is any one of the substituents described in Tables 7 to 15 (hereinafter referred to as Compound Group SX145).

Compound (L-37) in which $G^4$ is CH, $R^{3c}$ is a hydrogen atom, and $R^{3b}$ is any one of the substituents described in Tables 7 to 15 (hereinafter referred to as Compound Group SX146).

Compound (L-37) in which $G^4$ is a nitrogen atom $R^{3b}$ is a hydrogen atom, and $R^{3c}$ is any one of the substituents described in Tables 7 to 15 (hereinafter referred to as Compound Group SX147).

Compound (L-37) in which $G^4$ is a nitrogen atom, $R^{3b}$ is a hydrogen atom, and $R^{3c}$ is anyone of the substituents described in Tables 7 to 0.15 (hereinafter referred to as Compound Group SX148).

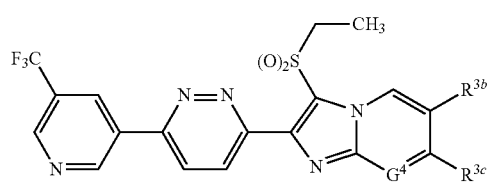
(L-38)

A compound represented by Formula (L-38) (hereinafter referred to as Compound (L-38)) in which $G^4$ is CH, $R^{3b}$ is a hydrogen atom, and $R^{3c}$ is any one of the substituents described in Tables 7 to 15 (hereinafter referred to as Compound Group SX149).

Compound (L-38) in, which $G^4$ is CH, $R^{3c}$ is a hydrogen atom, and $R^{3b}$ is any one of the substituents described in Tables 0.7 to 15 (hereinafter referred to as Compound Group SX150).

Compound (L-38) in which $G^4$ is a nitrogen atom, $R^{3b}$ is a hydrogen atom, and $R^{3c}$ is any one of the substituents described in Tables 7 to 15 (hereinafter referred to as Compound Group SX151).

Compound (L-38) in which $G^4$ is a nitrogen atom, $R^{3c}$ is a hydrogen atom, and $R^{3b}$ is any one of the substituents described in Tables 7 to 15 (hereinafter referred to as Compound Group SX152).

(L-39)

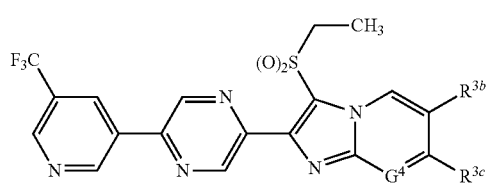

A compound represented by Formula (L-39) (hereinafter referred to as Compound (L-39)) in which $G^4$ is CH, $R^{3b}$ is a hydrogen atom and $R^{3c}$ is any one of the substituents described in Tables 7 to 15 (hereinafter referred to as Compound Group SX153).

Compound (L-39) in which $G^4$ is CH, $R^{3c}$ is a hydrogen atom, and $R^{3b}$ is any one of the substituents described in Tables 7 to 15 (hereinafter referred to as Compound Group SX154).

Compound (L-39) in which $G^4$ is a nitrogen atom, $R^{3b}$ is a hydrogen atom, and $R^{3c}$ is anyone of the substituents described in Tables 7 to 15-(hereinafter referred to as Compound Group SX155).

Compound (L-39) in which $G^4$ is a nitrogen atom, $R^{3c}$ is a hydrogen atom, and $R^{3b}$ is any one of the substituents described in Tables 7 to 15 (hereinafter referred to as Compound Group SX156).

(L-40)

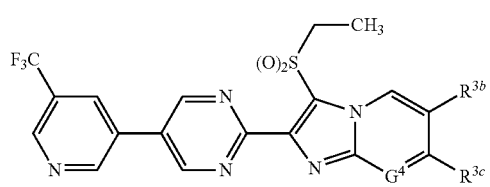

A compound represented by Formula (L-40) (hereinafter referred to as Compound (L-40)) in which $G^4$ is CH, $R^{3b}$ is a hydrogen atom, and $R^{3c}$ is any one of the substituents described in Tables 7 to 15 (hereinafter referred to as Compound Group SX157).

Compound (L-40) in which $G^4$ is CH, $R^{3c}$ is a hydrogen atom, and $R^{3b}$ is any one of the substituents described in Tables 7 to 15 (hereinafter referred to as Compound Group SX158).

Compound (L-40) in which $G^4$ is a nitrogen atom, $R^{3b}$ is a hydrogen atom, and $R^{3c}$ is any one of the substituents described in Tables 7 to 15 (hereinafter referred to as Compound Group SX159).

Compound (L-40) in which $G^4$ is a nitrogen atom, $R^{3c}$ is a hydrogen atom, and $R^{3b}$ is any one of the substituents described in Tables 7 to 15 (hereinafter referred to as Compound Group SX160).

(L-41)

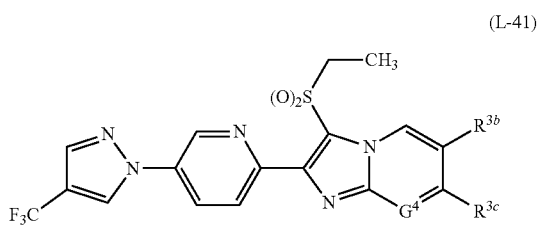

A compound represented by Formula (L-41) (hereafter referred to as Compound (L-41)) in which $G^4$ is CH, $R^{3b}$ is a hydrogen atom and $R^{3c}$ is any one of the substituents described in Tables 7 to 15 (hereafter referred to as Compound Group SX161).

Compound (L-41) in which $G^4$ is CH, $R^{3c}$ is a hydrogen atom, and $R^{3b}$ is any one of the substituents described in Tables 7 to 15 (hereinafter referred to as Compound Group SX162).

Compound (L-41) in which $G^4$ is a nitrogen atom, $R^{3b}$ is a hydrogen atom, and $R^{3c}$ is any one of the substitutents described in Tables 7 to 15 (hereinafter referred to as Compound Group SX163), Compound (L-41) in which $G^4$ is a nitrogen atom, $R^{3c}$ is a hydrogen atom, and $R^{3b}$ is any one of the substituents described in Tables 7 to 15 (hereinafter referred to as Compound Group SX164).

(L-42)

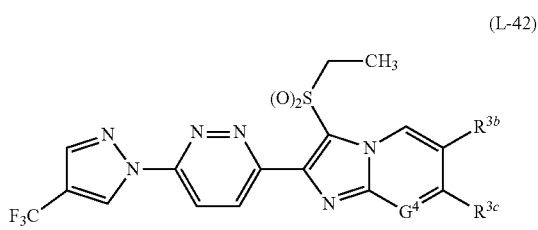

A compound represented by Formula (L-42) (hereinafter referred to as Compound (L-42)) in which $G^4$ is C, 1, $R^{3b}$ is a hydrogen atom, and $R^{3c}$ is any one of the substituents described in Tables 7 to 15 (hereinafter referred to as Compound Group SX165), Compound (L-42) in which $G^4$ is CH, $R^{3c}$ is a hydrogen atom and $R^{3b}$ is any one of the substituents described in Tables 7 to 15 (hereinafter referred to as Compound Group SX166).

Compound (L-42) in which $G^4$ is a nitrogen atom, $R^{3b}$ is a hydrogen atom, and $R^{3c}$ is any one of the substituents described in Tables 7 to 15 (hereinafter referred to as Compound Group SX167).

Compound (L-42) in which $G^4$ is a nitrogen atom, $R^{3c}$ is a hydrogen atom, and $R^{3b}$ is any one of the substituents described in Tables 7 to 15 (hereinafter referred to as Compound Group, SX168).

(L-43)

A compound represented by Formula (L-43) (hereinafter referred to as Compound (L-43)) in which $G^4$ is CH, $R^{3b}$ is a hydrogen atom, and $R^{3c}$ is any one of the substituents described in Tables 7 to 15 (hereinafter referred to as Compound Group SX169).

Compound. (L-43) in which $G^4$ s CH, $R^{3c}$ is a hydrogen atom, and $R^{3b}$ is any one of the substituents described in Tables 7 to 15 (hereinafter referred to as Compound Group SX170).

Compound (L-43) in which $G^4$ is a nitrogen atom, $R^{3b}$ is a hydrogen atom, and $R^{3c}$ is any one of the substituents described in Tables 1 to 15 (hereinafter referred to as Compound Group SX171).

Compound (L-43) in which $G^4$ is a nitrogen atom, $R^{3c}$ is a hydrogen atom and $R^{33}$ is anyone of the substituents described in Tables 7 to 15 (hereinafter referred to as Compound Group SX172).

(L-44)

A compound represented by Formula (L-44) (hereinafter referred to as Compound (L-44)) in which $G^4$ is CH, $R^{3b}$ is a hydrogen atom, and $R^{3c}$ is any one of the substituents described in Tables 7 to 15 (hereinafter referred to as Compound Group SX173).

Compound (L-44) in which $G^4$ is CH, $R^{3c}$ is a hydrogen atom, and $R^{3b}$ is any one of the substituents described in Tables 7 to 15 (hereinafter referred to as Compound Group SX74).

Compound (L-44) in which $G^4$ is a nitrogen atom, $R^{3b}$ is a hydrogen atom, and $R^{3c}$ is any one of the substituents described in Tables 7 to 15 (hereinafter referred to as Compound Group SX175).

Compound (L-44) in which $G^4$ is a nitrogen atom, $R^{3c}$ is a hydrogen atom, and $R^{3b}$ is any one of the substituents described in Tables 7 to 5 (hereinafter referred to as Compound Group SX176), The compound of the present invention may be used in admixture or in combination with one or more ingredients (hereinafter referred to as "the present ingredients") selected from the group consisting of Group (a), Group (b), Group (c), and Group (d).

In the present specification, the admixture or combination means that the compound of the present invention and the present ingredient are used at the same time, separately, or at a time, interval.

In a case where the compound, of the present invention and the present ingredient are used at the same time, the compound of the present invention and the present ingredient may each be contained in separate, formulations, or may be contained in one formulation.

An aspect of the present invention relates to a composition that contains one or more ingredients (that is, the present ingredients) selected from the group consisting of Group (a), Group (b), Group (c), and Group (d), and the compound of the present invention, Group (a) is a group of insecticidal active ingredients, acaricidal active ingredients, and nematicidal active ingredients which consists of Subgroups a-1 to a-10.

Subgroup a-1: Carbamate-based acetylcholinesterase (ACHE) inhibitors

Subgroup a-2: Organophosphorus-based acetylcholinesterase (AChE) inhibitors

Subgroup a-3: GABAergic chloride ion channel blockers

Subgroup a-4: GABAergic chloride ion channel allosteric modulators

Subgroup, a-5: Sodium channel modulators

Subgroup a-6: Nicotinic acetylcholine receptor (nAChR) competitive modulators

Subgroup a-7: Ryanodine receptor modulators

Subgroup a-8: Microbial materials.

Subgroup a-9: Nematicidal active ingredients

Subgroup a-10: Other insecticidal active ingredients and acaricidal active ingredients Group (b) is a group of fungicidal active ingredients which consists of Subgroups b-1 to b-18.

Subgroup b-1: PA fungicides (phenylamide)

Subgroup b-2: MBC fungicides (methylbenzimidazole carbamate)

Subgroup b-3: Thiazole carboxamide

Subgroup b-4: succinate dehydrogenase inhibitors (SDHIs)

Subgroup b-5: Qol fungicides (Qo inhibitors)

Subgroup b-6: Qil fungicides (Qi inhibitors)

Subgroup b-7: Thiophenecarboxamide

Subgroup b-8: AP fungicides (anilinopyrimidine)

Subgroup b-9: PP fungicides (phenylpyrrole)

Subgroup b-10: AH fungicides (aromatic hydrocarbon)

Subgroup b-11: DM1-fungicides (demethylation inhibitors)

Subgroup b-12: CCA fungicides (carboxylic acid amide)

Subgroup b-13: Piperidinylthiazole isoxazoline

Subgroup b-14: Tetrazolyl oxime

Subgroup b-15: Dithiocarbamate

Subgroup b-16: Phthalimide

Subgroup b-17: Microbial fungicides

Subgroup b-18: Other fungicides

Group (c) is a group of plant growth-regulating ingredients which consists of Subgroup c-1, Subgroup c-2, and Subgroup c-3.

Subgroup c-1: Plant growth-regulating ingredients

Subgroup c-2: Mycorrhizal fungi

Subgroup c-3: Rhizobia

Group (d) is a group of phyototoxicity-decreasing agents.

In the composition that contains the present ingredient and the compound of the present invention, an effect of the composition is expressed depending on a content or a content ratio of the present ingredient or the compound of the present invention in the composition. Therefore, a use of the composition can be determined depending on the effect expressed by the composition. The composition may have one or two or more uses.

An aspect of the composition is agrochemical composition,

Another aspect of the composition is a harmful-arthropod-controlling composition.

Yet another aspect of the composition is an insecticidal, acaricidal- or nematicidal composition.

Still yet another aspect of the composition is a fungicidal composition.

Still yet another aspect of the composition is a plant growth-regulating composition.

Still yet another aspect of the composition is a phytotoxicity-decreasing composition.

Examples of combinations of the present ingredient and the compound of the present invention are described below. For example, alanycarb+SX means a combination of alanycarb and SX. The abbreviation SX means "any one compound of the present invention selected from Compound Groups SX 1 to SX 176". In addition, all of the present ingredients as described below are known ingredients which can be obtained from commercially available formulations or can be produced using known methods. In a case were the present ingredient is a microorganism, the microorganism can also be obtained from a microorganism depositary institution. Numbers in parentheses indicate CAS registration numbers.

Combinations of the present ingredient of Subgroup a-1 and the compound of the present invention:

Alanycarb+SX, aldicarb+SX, bendiocarb+SX, benfuracarb+SX, butocarboxim+SX, butoxycarboxim+SX, carbaryl (NAC)+SX, carbofuran+SX, carbosulfan+SX, ethiofencarb+SX, fenobucarb (BPMC)+SX, formetanate+SX, furathiocarb+SX, isoprocarb (MIPC)+SX, rnethiocarb+SX, methomyl+SX, metolcarb+SX, oxamyl+SX, pirimicarb+SX, propoxur (PHC)+SX, thiodicarb+SX, thiofanox+SX, triazamate+SX, trimethacarb+SX, 3,5-dimethylphenyl N-methylcarbamate (XMC)+SX, and, xylylcarb+SX.

Combinations of the present ingredient of Subgroup a-2 and the compound of the present invention:

Acephate+SX, azarmethiphos+SX, azinphios-ethiyl+SX, azinphos-methyl+SX, cadusafos+SX, chlorethoxyfos+SX, chlorfenvinphos+SX, chlormephos+SX, chloroyrifos+SX, chiorpyrifos-methyl+SX, coumaphos+SX, cyanophos (CYAP)+SX, demeton-S-miethyl+SX, diazinon+SX, dichlorvos (DDVP)+SX, dicrotoplios+SX, dimiethoate+SX, dimethylvinphos+SX, disuilfotoil+SX, O-ethyl O-(4-nitrophenyl)phenylphosphonothioate (EPN)+SX, ethion+SX, ethoprophos+SX, famuphur+SX, fenamiphos+SX, fenitrothion (MEP)+SX, fenthion, (MPP)+SX, fosthiazate+SX, heptenophos+SX, imicyafos+SX, isbfenphos+SX, isopropyl-O-(methoxyaminothiiophosphoryl) salicylate+SX, isoxathion+SX, malathion+SX, mecarbam+SX, methamidophos+SX, methidathion (DMTP)+SX, mevinphos+SX, monocrotophos+SX, naled (BRP)+SX, omethoate+SX, oxydemeton-methyl+SX, parathion+SX, parathion-methyl+SX, phenthoate (PAP)+SX, phorate+SX, phosalone+SX, phosmet (PMP)+SX, phospharnidon+SX, phoxim+SX, pirimiphos-methyl+SX, profenofos+SX, propetamphos+SX, prothiofos+SX, pyraclofos+SX, pyridaphentliion+SX, quinalphos+SX, sulfotep+SX, tebupirimtfos+SX, temephos+SX, terbufos+SX, tetrachlorvinphos+SX, thiometon+SX, triazophos+SX, trichlorfon (DEP)+SX, and vamidothion+SX.

Combinations of the present ingredient of Subgroup a-3 and the compound of the present invention:

Ethiprole+SX, fipronil+SX, flufiprole+SX, chlordane+SX, endosulfan+SX, alpha-endosulfan+SX, and pyriprole+SX.

Combinations of the present ingredient of Subgroup, a-4 and the compound of the present invention:

Afoxolaner+SX, fluralaner+SX, broflanilide+SX, fluxametamide+SX, sarolaner, and lotilaner.

Combinations of the present ingredient of Subgroup a-5 and the compound of the present invention:

Acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermetlrin+SX, cyphenothrin+SX, deltamethrin+SX, empenthrin+SX, esfenvalerate+SX, etofenproxt=SX, fenpropathrin+SX, fenvalerate+SX, flucythrinate+SX, fluniethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, pralldthrin+SX, pyretlirins+SX, resmethrin+SX, silaiiubfen+SX, tefluthrin+SX kappa-tefluthrin+SX, tetramethrin+SX, tetramethylfiuthrin+SX, tralomethrin+SX, transfluthrin+SX, benfiutlirin+SX, flufenoprox+SX, sigma-cypermethrin+SX, turametlirin+SX, metofluthfin+SX, profluthrin+SX, dimefluthrin+SX, epsilon-metofluthrin+SX, epsilon-momiTuorothrin+SX, and methoxychlor+SX, Combinations of the present ingredient Subgroup a-6 and the compound of the present, invention:

Acetamiprid+SX, clothianidin+SX, dinotefuran+SX, imidacloprid & SX, nitenpyram+SX, thiacloprid+SX, thiamethoxam+SX, sulfoxaflor (S)+SX, flupyradiftirone+SX, triflumezopyrim 4 SX tiichldromezotiaz, cycloxapride+SX, and (E)-N-{1-[(6-chloropyridin-3-yl)methyl]pyridin-2(1H)-ylidene}-2,2,2-trifluoroacetamide (1689566-03-7)+SX.

Combinations of the present ingredient of Subgroup a-7 and the compound of the present invention:

Chlorantraniliprole+SX, cyantraniliprole+SX, cycloniliprolc+SX, lluhendianiide+SX, tetramliprole+SX, eyhalodiamide+SX, and a compound (1104384-14-6) represented by the following formula+SX.

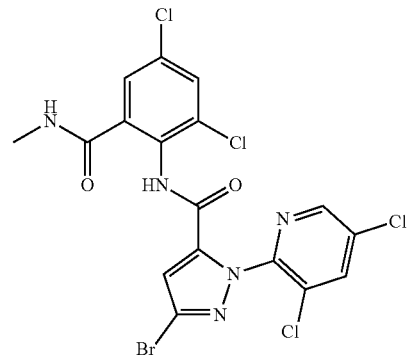 [SMILES: CNC(=O)c1cc(Cl)cc(Cl)c1NC(=O)c1cc(Br)nn1-c1ncc(Cl)cc1Cl]

Combinations of the present ingredient of Subgroup a-8 and the compound of the present invention:

*Beauveria hassiana* ANT-03+SX, *Beauveria brongniartii*+SX, *Paecilomyces fumosoroseus* Apopka 97+SX, *Paecilomyces lilacinus* 251+SX, *Paecilomyces tenuipes* T1+SX, *Verticillium lecani* NCIM 1312+SX, *Arthrobotrys dactyloides*+SX *Bacillus* sp. AQ175+SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H5a5b+SX, *Bacillus thuringi-* ensis AQ52+SX, *Bacillus thuringiensis* BD #32+SX, *Bacillus thuringiensis* CR-371+SX, *Bacillus thuringiensis* subsp. *Aizawai* ABTS-1857+SX, *Bacillus thuringiensis* subsp. *Aizawai* AM65-52+SX, *Bacillus thuringiensis* subsp. *Aizawai* QC-91+SX, *Bacillus thuringiensis* subsp. *Aizawai* Serotype H-7+SX, *Bacillus thuringiensis* subsp. *Kurstaki* ABTS351+SX, *Bacillus thuringiensis* subsp. *Kurstaki* BMP 123+SX, *Bacillus thuringiensis* subsp. *Kurstaki* EG234+SX, *Bacillus thuringiensis*, subsp, *Kurstaki* EG 7841+SX, *Bacillus thuringiensis* subsp. *Kurstaki* EVB113-19+SX, *Bacillus thuringiensis* subsp. *Kurstaki* F810+SX, *Bacillus thuringiensis* subsp. *Kurstaki* HD-1+SX, *Bacillus thuringiensis* subsp. *Kurstaki* PB54+SX, *Bacillus thuringiensis* subsp. *Kurstaki* SA-11+SX, *Bacillus thuringiensis* subsp. *Kurstalci* SA-12+SX, *Bacillus thuringiensis* subsp. *Tenebriosis* NB176+SX, *Bacillus thuringiensis* subsp. *Thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *lsraelensis* BMP 144+SX, *Bacillus thuringiensis* var. *israelensis* serotype H-14+SX, *Bacillus thuringiensis japonensis buibui*+SX, *Bacillus thuringiensis* var. *san diego* M-7+SX, *Bacillus thuringiensis* var. 7216+SX, *Bacillus thuringiensis* var. *aegypti*+SX, *Bacillus thuringiensis* var. T36, *Bacillus firmus* GB-126+SX, *Bacillus firmus* 1-1582+SX, *Bacillus megaterium*+SX, *Burkhpideria rinojensis* A396+SX, *Chromobacterium subtsugae* PRAA4-IT+SX, *Dactyllcla ellipsospora*+SX, *Dcctylaria thaumasia*+SX, *Hirsutella rhossiliensis*+SX, *Hirsutella minnesotensis*+SX, *Hirsutella thompsonii*+SX, *Lagenidium gigdnteum*+SX, *Lecanicillium lecanii* KVO 1+SX, *Metarhizium anisppliae*+SX, *Metarhizium anisppliae* var. *acridum*+SX, *Metarhizium flavoviride*+SX, *Monacrosporium phytomopagum*+SX, *Paenibacillus popilliae*+SX, *Pasteuria nishizawae* Pn1+SX, *Pasteuria penetrans*+SX, *Pasteuria usgae*+SX, *Pesteuria thoynei*+SX, *Serratia entomophila*+SX, *Verticillium chlamydosporium*+SX, and *Verticillium lecani* NCIM 1312+SX.

Combinations of the present ingredient of Subgroup a-9 and the compound of the present invention:

Abamectin+SX, fluazaiudplizine+SX, fluensulfpne+SX, fliiopyram, and tipxazafen+SX.

Combinations of the present ingredient Subgroup a-10 and the compound of the present invention:

Spinetoram+SX, spinosad+SX, emamectinibenzoate+SX, lepimectin+SX, milbemectin+SX, hydroprene+SX, kinoprene+SX, methoprene+SX, ivermectin+SX, milbcmycin Oxim+SX, moxidectin+SX, doramectin+SX, selamcctin+SX, acvnonapyr+SX, spiropidion+SX, fenoxyearb+SX, pyriproxyfen+SX, methyl Bromide+SX, chldropicrin+SX, sulturyt fluoride+SX, sodium aluminum fluoride or chidlite+SX, borax+SX, boric acid+SX, disodium dctaborate+SX, sodium borate+SX, sodium metaborate+SX, tartar emetic+SX, dazomet+SX, metairi+SX, pymetrozihe+SX, pyrifluquinazdne+SX, clofentezine+SX, hexythiazox+SX, diflovidazin+SX, etoxazoie+SX, diafenthiuron+SX, azocyclotin+SX, cyhexatin+SX, fenbutatin oxide+SX, prppargite+SX, tetradifon+SX, chlorfenapyr+SX, 2-methy-4,6-dinitrophenol (DNOC)+SX, sulfluramid+SX, bensultap+SX, cartap+SX, cartap hydrochloride+SX, thiocyclam+SX, thiosultap-disodium+SX, thiosultap-mottosodium+SX, bistrifluron+SX, chlorfluazurpn+SX, diflubenztiron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, bupro-fezin+SX, cyromazine+SX, chmmafendzitie+SX, halqfe-nozide+SX, methoxyfenozide+SX, tebufenozide+SX, amitraz+SX hydramethylnon+SX acequinocyl+SX, fluacrypyritti+SX, bifenazate+SX, fenazaquin YSX, fenpyroximate+SX, pyridaben 4 SX, pyrimidifen+SX, tebufenpyrad+SX, tolfenpyrad 4 SX, rqtendne+SX, indoxacarb+SX, metaflumizone+SX, spirodiclofen+SX, spiromesiten+SX, spirotetramat+SX, aluminum phosphide+SX, calcium phosphide+SX, phosphine+SX, zinc phosphide+SX, calcium cyanide+SX, potassium cyanide+SX, sodium cyanide+SX, cyenopyrafen+SX, eyflumetofen 4 SX, pyflubumide+SX, tlonicamid+SX, azadirachtin+SX, benzdximate 4 SX, brpmopropylatc+SX, chinomethionate+SX, dicofol+SX, pyridalyl+SX, lime sulfur 4 SX, suitor+SX, machine oil+SX, nicotine 4 SX, nicotine-sulfate+SX, afidopyropen+SX, flometoquin+SX, metoxadiazone 4 SX, pyriminostrobin+SX, N-[3-chloro-1-(pyridin-3-yl)-1H-pyrazol-4-yl]-N-ethyl-3-(3,3,3-trifluoropropylsulfanyl)propanamide (1477919-27-9) 4 SX, N-[3-chloro-1-(pyridin-3-yl)-1H-pyrazol-4-yl]-N-ethyl-3-(3,3,3-trifluoropropanesulfinyl) propanamide (1477919-37-7) 4 SX, 5-(1,3-dioxan-2-yl)-4-[4-(trifluoromethyl)benzyloxy]pyrimidine (1449021-97-9)+SX, acrep+SX, butopyronoxyl+SX, camphor+SX, d-camphor+SX, carbOxide+SX, dibutyl phthalate+SX, diethyltoluamide+SX, dimethyl carbate+SX, dimethyl pihthalate+SX, dibutyl succinate+SX, dibutyl adipate+SX, ethohexadiol+SX, hexamide 4 SX, jcaridin+SX, methoquirobutyf+SX, metiiyhiepdeeanamjde+SX, 2-(octylthiojetiianol (2-(octylthio)ethaitol)+SX, butoxypolypropylene glybol-4 SX, oxamate+SX, quwenzhi+SX, quyingding+SX, zcngxiaon+SX, rebemide+SX, BT crop protein Cry1Ab, BTcrop protein Cry1Ac, BT crop protein Cry1Fa, BT crop protein Cry1A, 105, BT crop protein, pry2Ab, BT crop protein Vip3A, BT Crop protein Cry3A, BT crop protein Cry3Ab. BT crop protein Cry3Bb, BT crop protein Cry34Abl/Cry35Abl.

Combinations of the present ingredient of Subgroup b-I and the compound of the present invention:

Benalaxyl+SX, benalaxyl+SX, furalaxyl+SX, metalaxyl+SX, metalaxyl M+SX, oxadixyl+SX, and ofurace+SX.

Combinations of the present ingredient of subgroup b-2 and the compound of the present invention:

Benomyl+SX, carbendazim+SX, fuberidazple+SX, thiabendazole+SX, thiophanate+SX, and thiophanaternietliyi+SX.

A combination of the present ingredient of Subgroup-3 and the compound of the present invention:

Ethaboxam+SX.

Combinations of the present ingredient of Subgroup b-4 and the compound of the present invention:

Benodanil+SX, flutolanil+SX, mepronil+SX, iSofetatriid+SX, fenfuram+SX, carboxin+SX, oxycarbbxin+SX, thifluzamide+SX, benzovindi flupyr+SX, bixafen+SX, fluxapyroxad+SX, furametpyr+SX, isopyrazam+SX, penflufen+SX, penthiopyrad+SX, scdaxane+SX, pydiflumetofen+SX, boscalid+SX, pyrazillumid+SX, 3-difluoforitethyl-N-methoxy-1-methyl-N-[(1R)-1-methyl-2-(2,4,6-trichlorophenyl)ethyl]pyrazole-4-carboxamide (1639015-48-7)+SX, 3-difluoromethyl-N-methoxy-1-methyl-N-[(1S)-1-methyl-2-(2,4,6-trichlorophenyl)ethyl]pyrazole-4-carboxamide (1639015-49-8)+SX, N-cyclopropyl-3-(difluoromethyl)-5-fluoro-N-(5-chloro-2-isopropylbenzyl)-1-methyl-1H-pyrazole-4-carboxamide (1255734-284)+SX, 3-difluoromethyl-1-methyl-N-1,1,3-trimethylindan-4-yl) pyrazole-4-carboxamide (141573-94-6)+SX, 3-difluoroniethyl-1-methyl-N-[(3R)-1,1,3-trimethylindan-4-yl]pyrazole-4-carboxamide (1352994-67-2)+SX, 3-difluorormethyl-N-(7-fluoro-1,1,3-trimiethylindan-4-yl)-4-methylpyrazole-4- carboxamide (1383809-87-7)+SX, and 3-difluoromethyl-N-[(3R)-7-fluoro-1,1,3-trimethylindan-4-yl]-1-methylpyrazole-4-carboxamide (1513466-73-3)+SX.

Combinations of the present ingredient of Subgroup b-5 and the compound of the present invention:

Azoxystrobin+SX, coumoxystrobin+SX, enoxastrobin+SX, flufenoxystrobin+SX, picpxystrpbin+SX, pyraoxystrobjn+SX, maiidestrobiri+SX, pyraclostrobin+SX, pyrametostrdbin+SX, triclopyricarb+SX, kresoxim-methyl+SX, trifloxystrobin+SX, dimoxystrobin+SX, tenaminstrobin+SX, metominostrobin+SX, orysastrobin+SX, famoxadone+SX, fiupxastrpbin+SX, fenamidone+SX, and pyribencarb+SX.

Combinations of the present ingredient of Subgroup b-6 and the compound of the present invention:

Cyazofamid+SX, amisulbrom+SX, binapacryi+SX, meptyldinocap+SX, dinocap+SX, and fluazinam+SX, A combination of the present ingredient of Subgroup b-7 and the compound of the present invention:

Silthiofam+SX,

Combinations of the present ingredient of Subgroup b-8 and the compound of the present invention:

Cyprodinil+SX, mepanipyrini+SX, and pyrimethanil+SX.

Combinations of the present ingredient of Subgroup b-9 and the compound of the present invention:

Fenpiclonil+SX, and fludioxdnil+SX,

Combinations of the present ingredient of Subgroup b-10 and the compound of the present invention:

Biphenyl+SX, chloroneb+SX, dicloran+SX, quintozene+SX, tecnazene+SX, and tolelofos-methyl+SX.

Combinations of the present ingredient of Subgroup b-11 and the compound of the present invention:

Azaconazole+SX, bitertanol+SX, bromuconazple+SX, cyproconazole+SX, difenocpnazole+SX, diniconazole+SX, diniconazoie-M+SX, epoxiconazole+SX, etaconazole+SX, fenbuconazole, fluquincpnazole+SX, tlusilazole+SX, flutriafol+SX, bexacpnazoie+SX, imibenconazole+SX, ipconazole+SX, ipfentriflucpnazple+SX, mefentrifluconazole+SX, meiconazole+SX, myclobutanil+SX, penconazote+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrispxazole+SX, fenarimol+SX nuarimpl+SX, imazalil+SX, oxpoconazole+SX oxppcpnazole iumarate+SX, pefUrazoate+SX, proehloraz+SX, and triflumizole+SX.

Combinations of the present ingredient of the Subgroup b-12 and the compound of the present invention:

Dimethpmorph+SX, flumorph+SX, pyrimorph+SX, benthiavalicarb+SX, benthivalicarb-isopropyl+SX, iprovalicarb+SX, valifenalate+SX, and mandipropamid+SX.

A combination of the present ingredient of Subgroup b-13 and the compound of the present invention:

Oxathiapiprolin+SX.

A combination of the present ingredient of Subgroup b-14 and the compound of the present invention:

Picarbutrazox+SX,

Combinations of the present ingredient of Subgroup b-15 and the compound of the present invention:

Ferbam+SX, mancozeb+SX, rrianeb+SX, metiram+SX, prdpineb+SX, thiram+SX, zineb+SX, and ztram+SX.

Combinations of the present ingredient of Subgroup b-16 and the compound of the present invention:

Captan+SX, captafol+SX, and folpet+SX.

Combinations of the present ingredient of Subgroup b-17 and the compound of the present invention:

*Agrobacterium radiobactor* K84+SX, *Agrobacterium radiobactor* K1026+SX, *Bacillus amyloliquefaciens* B3+SX, *Bacillus amyloliquefaciens* QST713+SX, *Bacillus amyloliquefaciens* FZB24+SX, *Bacillus amyloliquefaciens* MBI600+SX, *Bacillus amyloliquefaciens* D747+SX, *Bacillus amyloliquefaciens* AT332+SX, *Bacillus amyloliquefaciens* DB101+SX, *Bacillus amyloliquefaciens* DB102+SX, *Bacillus amyloliquefaciens* FZB42+SX, *Bacillus amyloliquefaciens* GB03+SX, *Bacillus amyloliquefaciens* IN937a+SX, *Bacillus amyloliquefaciens* isolate 6246+SX, *Bacillus licheniformis* HB-2+SX, *Bacillus licheniformis* SB3086+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF 2856+SX, *Bacillus subtilis* AQ153+SX, *Bacillus subtilis* QST713+SX, *Bacillus subtilis* HA10404+SX, *Bacillus subtilis* Y1336+SX, *Bacillus subtilis* AQ743+SX, *Bacillus subtilis* D747+SX, *Bacillus subtilis* DB101+SX, *Bacillus Subtilis* GB03+SX, *Bacillus subtilis* IAB/BS03+SX, *Bacillus subtilis* MBI600+SX, *Bacillus subtilis* QST30002/AQ30002+SX, *Bacillus subtilis* QST30004/AQ30004+SX, *Bacillus subtilis* QST714+SX, *Bacillus subtilis* var. *Amyloliquefaciens* FZB24+SX, *Burkholderia cepacia*+SX, *Burkholderia cepacia* type Wisconsin J82+SX, *Burkholderia cepacia* type Wisconsin M54+SX, *Candida oleophila* O+SX, *Candida saiitoana*+SX, *Chaetomium cupreum*+SX, Clonostachys *rosea*+SX, *Conipthyrium minitans* CGMCG8325+SX, *Coniothyrium minitans* CON/M/9B8+SX, *cryptococcus albidus*+SX, *Fusarium oxysporum* Fo47+SX, *Glyocladium catenulatum* 0.11446+SX, *Paenibacillus polymyxa* AC-1+SX, *Paenibacillus polymyxa* BS-0105+SX, *Pantoea agglomerans* E325+SX, *phlebiopsis gigantea* VKA I992+SX, *Pythium oligandrum* DV74+SX, *Streptomyces griseoyiridis* K61+SX, *Streptomyces lydicus* WYCD108US+SX, *Streptomyces lydicus* WYECI08+SX, *Variovorax paradoxus* CGF4526+SX, *Erwinia cardtobora* CGE234M403+SX, *Pseudomonas fluorescens* G7090+SX, *Pseudomonas aureofacicns* TX-1+SX, *Pseudomonas chlororaphis* 63-28+SX, *Pseudomonas chloraphis* MA342+SX, *Pseudomonas fluorescens* 1629RS+SX, *Pseudomonas fluorescens* A506+SX, *Pseudomonas fluorescens* CL145A+SX, *Pseudomonas fluorescens* PF-A22 UL+SX, *Pseudomonas syringae* 742RS+SX, *Pseudomonas syringae* MA-4+SX, *Pseudpzyma flocculosa* PF-A22UL+SX, *Pseudomonas rhodcsiae* HA1-0804+SX, *Talaromyces flavus* SAY-Y-94-01+SX, *Trichoderma atroviride* SKT-1+SX, *Trichoderma asperellum* ICC012+SX, *Trichoderma asperellum* T34+SX, *Trichoderma atroviride* CNCM 1-1237+SX, *Trichoderma atroviride* SCI+SX, *Trichoderma liarzianum* 21+SX, *Trichoderma harzianum* DB L04+SX, *Trichodemia liarzianum* DSM 14944+SX, *Trichoderma hamanum* ESALQ-1303+SX, *Trichodemia liarzianum* ESALQ-1306+SX, *Trichoderma harzianum* IIHR-Th-2+SX, *Trichoderma harzianum* kd+SX, *Trichoderma harzianum* MOI+SX, *Trichoderma liarzianum* SF+SX, *Trichoderma harzianum* T39+SX, *Trichoderma polysporum* EVII 206039+SX, *Trichoderma stromaticum*+SX, *Trichoderma viride* GL-21+SX, and Harpin protein+SX.

Combinations of the present ingredient of Subgroup b-18 and the compound of the present invention:

Bupirimate+SX, dimethirimol+SX, ethirimol+SX, hymexazole+SX, oethilinone+SX, oxolinie acid+SX, diethpfencarb+SX, zqxamjde+SX, peneycuron+SX, fluopicblide+SX, phenamacril+SX diflumctorim+SX, ttiltenpyrad+SX, fentin acetate+SX fentin chloride+SX, fentin hydroxide+SX ametoctradin+SX blasticidin-S+SX, kasugamycin 4-XX, streptomycin+SX oxytetracycline+. SX, quinoxyfen+SX, proquinazid+SX, chlozolinate+SX, dimethachlone+SX, iprodione+SX, procymidone+SX, vihcldzolin+SX edifenphos+SX, iprdbenfqs+SX, pyrazdphds+SX, isoprothioiane 4-SX, etridiazole+SX, iodocarb+SX, propamocarb+SX, prothiocarb+SX, aldimorph+SX, dpdemqrph+SX, fenpropidin+SX, fenpropimorph+SX, piperalin+SX, spiroxamine+SX, tridemorph+SX, fenhexamid+SX, fenpyrazamine+SX, pyrjbuticarb+SX, naftifine+SX, terbinafine+SX, polyoxins+SX, phthalide+SX, pyroquiion+SX, tricyciazole+SX, carprqpaipid+SX, diclocymet+SX, tenoxanil+SX, tolprocarb+SX, acibenzolar-S-methyl+SX, prqbenazole+SX, tiadinil+SX, isotianil+SX, laminarin+SX, cymoxanjl+SX, fosetyl+SX, teclofthalam+SX, triazoxide+SX, flusulfamide+SX, diclomezine+SX, methasulfocarb+SX, cyflufamide+SX, metrafenone+SX, pyriqferione+SX, dodine+SX, flutianil+SX, ferimzdne+SX, tebufloquin+SX, validamycin+SX, basic copper chloride+SX, cupric hydroxide+SX, basic copper sulfate+SX, dodecylbenzeiiesulphtinic acid bisetliylenediamine copper [II] Salt (DBEDC)+SX, organic copper+SX, sulfur & SX, chlorothalbnil+SX, dichlofluanid+SX, tolyl fluanid+SX, guazatine+SX, iminoctadine+SX, anilazine+SX, dithianon+SX chinomethionat+SX, lluorpimide+SX, dipymetitrone+SX, quinofumelin+SX, dichlobentiazox+SX, 3-chloro-5-phenyl-6-inethyl-4-(2,6-diiliioroplienyl)pyridazine (1358061-55-8)+SX, fenpicoxamid+SX, N'-[4-({3-[(4-chlorophenyl)methyl]-1,2,4-thiadiazoi-5-yl}oxy)-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate (1360819-11-9)+SX, 4-(2-bromo-4-fluorophenyl)-N-(2-chloro-6-fluoraphenyl)-1,3-dimethyl-1H-pyrazole-5-amine (1362477-26-6)+SX, 2,2-dimethyl-9-flouro-5-(quinolin-3-yl)-2,3-dihydrobenz[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyriniidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylaprylate (39491-78-6)+SX, N-[(2-chlorothiazol-5-yl)methyl]-N-ethiyl-6-methoxy-3-nitropyridin-2-amine (1446247-98-8)+SX, 1 [2-({[1-(4-chlorophenyl)-1H-pyrazol-3-yl]oxy}methyl)3-methylphenyl]-4-methyl-5-oxo-4,5-dihydro-1H-tetrazole (1472649-01-6)+SX, aminopyrifen+SX, and Colletochlorin B+SX, Combinations of the present ingredient of Subgroup c-1 and the compound of the present invention:

Ethephon+SX, chldrmequat+SX, chidmiecuat-chloride+SX, mepiqiiat+SX, mepiquat-chloride+SX, Gibbered in A3+SX, abscisic acid+SX, Rinetin+SX, benzyladenine+SX, forchlorfenuron+SX, and thidiazuron+SX, Combinations of the present ingredient of Subgroup c-2 and the compound of the present invention:

*Glomus* spp.+SX, *Glomus intraradices*+SX, *Glomus mosseae*+SX, *Glomus aggregatum*+SX, and *Glomus etunicatum*+SX.

Combinations of the present ingredient of the Subgroup c-3 and the compound of the present invention:

*Bradyrhizobium elKani*+SX, *Bradyrhizobium japonicuM*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, and *Rhizobium* spp.+SX.

Combinations of the present ingredient of Group (d) and the compound of the present invention:

Benoxacor+SX, cloquintocet-mexyl+SX, cyometrinil+SX, dichlormid+SX, fenchlorazole-ethyl+SX$_4$ fenclorim+SX, flurazole+SX, furilazole+SX, mefenpyr-diethyl+SX+2-(dichloromethyl)-2-methyl-1,3-dipxolane (MG191)+SX, oxabetrinil+SX, allidochlor+SX, ispxadifen-ethyl+SX, cyprosulfamide+SX, fluxofenim+SX, 1,8-naphthalic anhydride+SX, and 4-(dichloroacetyl)-1-oxa-4-azaspiro[4.5]decane (AD-67)+SX, In addition, the compound of the present invention can be used in admixture or in combination with one or more ingredients (hereinafter referred to as present ingredients) selected from the group consisting, of Group (e), Group (f), Group (g), and Group (h).

An aspect of the present invention relates to a composition that contains one or more ingredients (that is, the present ingredients) selected from the group consisting of group (c). Group (f), Group (g), and Group (h).

Examples of combinations of the present ingredient and the compound of the present invention are described below.

Combinations of the present ingredient of Group (e) and the 'compound' of the present invention:

1-Dodecyl-1H-imidazole+SX, N-(2-ethylhexyl)-8,9,10-trinorbom-5-ene-2,3-dicarboximide+SX, bucarpolate+SX, N,N-dibutyl-4-chlorobenzenesulfonamide+SX, dietholate+SX, diethylmaieate+SX, piperonyl butOxide+SX, piperonyl cyclonene+SX, piprotal+SX, propyl isome+SX, saffoxan+SX, sesamex+SX, sesamdlin+SX, sulfoxide+SX, Verbutin+SX, 1,1-bis(4-chlorophenyl)ethanol (DMC)+SX, 1,1-bis(4-chlorophenyl)-2,2,2-trifluoroethanol (PDMC)+SX, 1,2-epoxy-1,2,3,4-tetrahydrbnaphthalene (ETN)+SX, 1,1,1-trichloro-2,3-expoxypropane (ETP)+SX, phenylsaligenin cyclic phosphate (PSCP)+SX, S,S,S-tributyl phosphorotrithioate (TBPt)+SX, and triphenyl phosphate (TPP)+SX.

Combinations of the present ingredient of Group (f) and the compound of the present, invention:

Anthraquinone+SX, chloralose+SX, acrep+SX, butopyronoxyl+SX, camphor+SX, d-camphor+SX, carboxide+SX, dibutyl phthalate+SX, deet+SX, dimethyl carbate+SX, dimethyl phthalate+SX, dibutyl succinate+SX, dibutyl adipate+SX, ethohexadiol+SX hexamide+SX, icaridin+SX, methoquin-butyl+SX, methylneodecanamide+SX, 2-(octylthio)ethanol+SX, butoxypolypropylene glycol+SX, oxamate+SX, quwenzhi+SX, quyingding+SX, zengxiaon-t SX, rebemide+SX, copper naphthenale+SX, and zinc naphthertate+SX, Combinations of the present ingredient of Group (g) and the compound of the present invention:

Bis(tributyltin) oxide+SX, allicin+SX, bromoacetamide+SX, cloethocarb+SX, copper sulfate+SX, fentin+SX, ferric phosphate (III)+SX, metaldehyde+SX, niclosamide & SX, pentachlorophenpl+SX, sodium pentachlorophenoxide+SX tazimcarb+SX, tralopyril+SX, and trifenmorph+SX.

Combinations of the present ingredient of Group (IV) and the compound of the present invention:

(E>2-hexenal+SX, (E)-2-octadecenal+SX, (E)-4-tridecen-1-yl acetate+SX, (E)-5-decen-1-yl acetate+SX, (E)-S-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimetliylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-t-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11 octadecenal+SX, (Z)-13-octadecenal+SX, (Z)-hexadec-13-en-11-yn-1-yl acetate+SX, (ZH3-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadieri-1-yl acetate+SX, (E,Z)-2,13-ocladccadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dpdecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl, acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2 (3H)-furanone+SX, (2R,5R)-ethyl-1,6-dioxaspiro[4,4] nonane+SX, (2R,5S)-ethyl-1,6-dioxaspiro[4,4]nonane+SX, (4R,8R)-4,8-dimetliyldecanal+SX, (4R,8S)-4,8-dimiethyldecanal+SX, 2,4-dimethyl-5-ethyl-6,8-dipxabicyclo[3,2,1] octane+SX, (-)-4-methyl-3-heptanol+SX, 1,7-dioxaspiro[5, 5]undecane+SX, 3-carene+SX, 3-methylcyclohex-Z-en-1-One+SX, 14-methyloctadec-1-ene+SX, 4-methylnonan-5-ol+SX, 4-methylnonan-5-one+SX, +(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodeeanoate+SX, tetradecan-1-ol+SX, tetradec-11-en-1-ol+SX, tetradec-11-en-t-yl acetate+SX, tridec-4-en-1-yl acetate+SX, (3S,6R)-3-methyl-6-isoprdpenyl-9-decen-1-yl acetate+SX, (3S,6S)-3-methyl-6-isdpropenyl-9-decen-1-yl acetate+SX, alpha-multistriatin+SX alpha-pincne+SX, endo-brevicomin+SX, exo-brevicdmin+SX, camphene+SX, codleiure+SX codlemone+SX, cuelure+SX, disparlure+SX, dorninicalure+SX, eugenol+SX famcsol+SX ferrolure+SX, frontalin+SX, gossyplure+SX, grandlure+SX, grandlure I+SX, grandlure II+SX, grandlure III+SX, grandlurc IV+SX, hexalure+SX, ipsedienol+SX, ipsenol+SX, japonilure+SX, lineatin+SX, litlue+SX, Iddplure+SX, medlure+SX, megatomoic acid+SX, methyl eugenol-+SX, muscalure+SX, nerolidol+SX, orfralure+SX, cryctalure+SX, ostramone+SX, rhyncolure+SX, siglure+SX, sordidin+SX, sulcatpl+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, and S-verbenone+SX.

As harmful arthropods against which the compound of the present invention has an efficacy, for example, harmful insects and harmful acarids can be mentioned. As such harmful arthropods, specifically, for example, the following can be mentioned, Hemiptera: Delphacidae such as *Laodelphax striatellus, Nilaparvata lugens, Sogatella furcifera, Peregrinus maidis, Javesella pellucida, Perkinsiella saccharicida*, and *Tagospdes orizicoius*; Cicadellidae such as *Nephotettix cincticeps, Nephotettix virescens, Nephotettix nigropictus, Recitia dorsalis, Empoasca qnukii, Empoasca fabae, Dalbulus maidis*, and *Cofana spectra*; Cercopidae such as *Miahanarva posticata* and *Mahanarva fimbriolata*, Aphididae such as *Aphis fabae, Aphis glycines, Aphis gossypii, Aphis pomi, Aphis spiraecola, Myzus persicae, Biachycaudus helichrysi, Brevicqryne brassicae*, Rosy apple aphid (*Pysaphisplantaginea*), *Lipaphis erysimi, Macrosiphum euphorbiae; Aulacorthum solani, Nasonovia ribisnigri, Rliopalosiphum padi, Rhopalosiphum maidis, Toxoptera Citricida, Hyalopterus pruni, Melanaphis sacchari, Tetraneura nigriabdominalisv Ceratovacuna lanigera*, and *Eriosoma lanigerum*; Phylloxeridae such as *Daktulpsphaira vitifoliae*, Pecan *phylloxera* (*Phylloxera devastatrix*), Pecan leaf *phylloxera* (*Phylloxera notabilis*), and Southern pecan leaf *phylloxera* (*Phylloxera russellae*); Adelgidae such as *Adelges tsugae, Adelges piceae*, and *Aphrastasia pectinatae*; Pentatomidae such as *Scotiriophara lurida*, Malayan rice black bug (*Seotinophara coarctata*), *Nezara antennata. Eysarcoris aeneus, Eysarcoris lewisi, Eysarcoris ventralis, Eysarcoris annamita, Halyomorpha halys, Nezara viridula*, Brown stink bug (*Euschistus heros*), Red banded Stink bug (*Piezodorus guildinii*), *Oebalus pugnax*, and *Diehelops melacanthus; Cydhidae* such as Burrower brown bug (*Scaptocoris castanea*); Alydidae such as *Riptortus Pedestris, Leptocorisa chinensis*, and *Leopocorisa acuta*; Coreidae such as *Cletus punctiger* and *Leptoglossus australis*; Lygaeidae such as Caverelius saccharivorus, Togo *hemipterus*, and *Blissus leucqpterus*; Miridae, such as *Trigonptylus caelestialium, Stenotus rubrovittatus, Stenodema calcarata*, and *Lygus liheolafis*; Aleyrpdidae such as *Trialeurodes vaporariorum, Bemisia tabaci. Dialeurodcs citri, Aleurocanthus spiniferus, Aleurocanthus camelliae*, and *Pealiuse euryae*; Diaspididae such as *Abgrallaspis cyaiiophylii, Aonjdieila aurantii. Diaspidiotus perniciosus, Pseudaulacaspis pentagona, Unaspis yanonensis*, and *Unaspis citri*; Coccidae such as *Cerdplastes rubens*; Margarodidae such as *iceryapurchasi* and *Iccrya seychellarum; Pseudococci dae* such as *Phenacoccus solani, Phenacoccus solenopsis, Planococcus kraUnhiae, Pseudococcus comstocki, Planococcus citri, Pseudococcus calceolariae, Pseudococcus longispinus*, and *Brevennia rehi*; Psyllidae such as *Diaphorina citri, Trioza erytreae, Cacopsylla pyrisuga, Cacopsylla chinensis, Bactericera cockerelli*, and Pear psylla (*Cacopsylla pyricola*); Tingidae such as *Corytliucha ciliata, Corythucha mannorata, Stephanitis naslii*, and *Stephanitis pyridides*; Cimieidae such as *Cimcx ieetlilatius*, Cicadidae such as Giant Cicada (*Quesadagi gas*), and *Triatoma* spp. such as *Triatoma infestans*.

Lepidoptera: Crambidae such as *Chilo supprcssalis*, Darkheaded stem borer (*Chib polychrysus*), White stem borer (*Scirpophaga innotata*), *Scirpophaga incertuias, Rupela albina, Cnaphalocrocis medinalis, Marasmia patnalis, Marasmiaexigua, Motarcha derogata, Ostrinia fumacalis*, European corn borer (*Gstrinia nubilahs*), *Tlellula undalis, Herpetogramma luctuosale, Pediasia teterreilus, Nymphula depunctalis*, and Sugarcane borer (*Diatraea saccharalis*); Pyralidae such as *Elasmopalpus ligndselius, Plodia intcrpunctella*, and *Euzophera batangensis*; Noctuidae such as *Spodoptcra litura, Spodoptera exigua, Mythimna separata, Mamestra brassicae, Sesamia inferens, Spodoptera mauritia, Naranga aenescens, Spodoptera frugiperda, Spodoptera exempta, Agrotis ipsilon, Autographa nigrisigna, Plusia festucae*, Soybean looper (*Chrysodeixis inckidens*), *Trichdplusia* spp., *Heliothis* spp. such as *Heliothis virescens, Helicoverpa* spp. such as *Helicoverpa armigera* and *Helicoverpa zea*, Velvetbean caterpillar (*Anticarsia gemmatalis*). Cotton leafworm (*Alabama argillacea*), and Hop vine borer (*Hydraecia immanis*); Pieridae such as *Pieris rapae*; Tortricidae such as *Graphplita molesta, Gtapholita dimorpha, Leguminivora glycinivorella, Matsumuraeses azukivora, Adoxpphyes orana fasciata, Adpxpphyes*

*honmai, Homona magnanima, Archips fuscocupreanus, Cydia pomotlella, tetranlpera sdhistaceana.* Bean Shoot Borer (*Epinotia aporema*), and Citrus fruit borer (*Ecdytolppha aurantiana*); Graciliariidae such as: *Caioptilia theiypra* and *Phyllonorycter ringoniella*; Carposiriidae such as *Carposina sasakii*; Lyonetiidae such as Coffee Leaf miner (*Leucoptera coffeela*), *Lyonetia clerkella*, and *Lyonetia prunifoliella*; Lymantriidae, for example, *Lymantria* spp. such as *Lymantria dispar*, and *Euproctis* spp. such as *Euproetis pseudoconspersa*: Plutellidac such as *Plutella xylostella*; Gelechiidae such as *Anarsia lineatella, Helcystogramma triannulella, Pectinophora gossypiella, Phtlrorimaea operculclla* and *Tula absoluta*; Arctiidac such as *Hyphantria cunea*; Castniidae such as Giant Sugarcane borer (*Telchin licus*); Cossidae such as *Cosus insularis*; Geometridae such as *Ascotis selenaria*; Limacodidae such as *Parasa lepida*; Stathmopodidae such as *Stathmopoda masinissa*; Sphingidae such as *Acherontia lachesis*; Sesiidae such as *Nokotia feralis, Synanthedon hector*, and *Synanthedon tenuis*; Hesperiidae such as *Pamara guttata*, and Tineadae such as *Tinea translucens* and *Tineola bisselliella*.

Thysanoptera: Tliripidae such as *Frankliniella occidentalism Thrips palmi, Scirtothrips dorsalis, Thrips tabaci, Frankliniella intonsa, Stcnchaetothrips biformis*, and *Echinothrips americanus*; and Phlaeothripidae such as *Haplothrips aculeatus.*

Diptera: Anthpmyiidae such as *Delia plalura, Delia antiqua*, and *Pegomya cuniculafia*; Ulidiidae such as *Tetanops myopaefomiis*; Agromyzidae such as *Agiromyza oryzae, Liriomyza sativae, Uriomyza trifolii*, and *Chromatomyia horticola*; Chloropidae such as *Chlorops oryzae*; Tephritidae such as *Bactrocera cucurbitae, Bactrocera dorsalis, Bactrocera latifrons, Bactrocera oleae, Bactrocera tryoni, Ceratltis capitata, Rhagolctis pomonella*, and *Rhacochlaena japonica*; Ephydridae such as *Hydrellia griseola, Hydrellia philippina*, and *Hydrellia sasakii*; Drosophilidae such as *Drosophila suzukii*; Phoridae such as *Megaselia spiracularis*; Psychodidae such as *Clogmia albipunctata*; Sciaridae such as *Bradysia difformis*; Cecidomyiidae such as *Mayetiola destructor* and *Orseolia orzae*; Diopsidae such as *Diopsis macrdphthalma*; Tipulidae such as *Tipula aino*, Common cranefly (*Tipula oleracea*), and European cranefly (*Tipula paludosa*); Culicidae such as *Culex pipiens pallens, Aedes aegypti, Aedes albdpicutus, Anopheles hyracanus sinesis, Culex quinquetasciatos, Culex pipiens molestus Eorskal*, and *Culex quinquefasciatus*; Siniuiidae such as *Prosimulium yezoerisis* and *Simulium ornatum*; Tabanidae such as *Tabanus trigonus*; Muscidae such as *Muscadomestica, Muscina stabulans, Stomoxys calcitrans*, and *Hacmatobia irritans*; Calliphoridae; Sarcophagidae; Chironomidae such as *Chironomus plumosus, Chironomus* yoshimatsui, and *Glyptotendipes tdkunagai*, and Fannidae.

Coleoptera: Chrysomelidae such as *Diabrotica virgifera virgifera, Diabrotica undecimpunctata howardi, Diabrotica barberi, Diabrotica virgifera zeae, Diabrotica balteata.* Cucurbit Beetle (*Diabrotica speciosa*), *Cerotoma trifurcata, Qulema melanopus. Aulacophora femoralis, Phyllotreta striolata*, Cabbage flea beetle (*Phyllotreta cruciferae*). Western Black flea beetle (*Phyllotreta pusilla*), Cabbage stem flea beetle (*Psylliodes chrysocephala*), *Leptinotarsa decemlineata, Oulema oryzae, Colaspis brunnea, Chaetocnema pulicaria, Chaetpcnema confinis, Epitrix cucumeris, Dicladispa armigera*, Grape Colaspis (*Colaspis brunnea*), southern corn leaf beetle (*Myochrous denticollis*), *Laccoptera quadrimaculata*, and *Epitrix hittipennis*; Carabidae such as Seedcom beetle (*Stenolophus lecontei*) and Slender seedcom beetle (*Clivina impressifrons*); Scarabaeidae such as *Anomala cuprea, Anomala rufocuprea, Anomala albopilosa, Popillia japonica. Heptophylla picea*, European Chafer (*Rhizotrogus majalis*), *Tomarus gibbosus. Holotrichia* spp, *Phyllpphaga* spp. such as *Phyllophaga crinita*, and *Diloboderus* spp. such as *Dilobodems abderus*; Curctilionidae such as *Araecerus coffeae, Cylas formicarius. Euscepes postfasciatus, Hypera postica, Sitophilus zeamais, Echinocnemus squameus, Lissorhoptrus otyzophilus, Rhabdoscelus lineatocpllis, Anthonbmus grandis, Sphenpphonis venatus*, Southern Corn Billbug (*Sphenophorus callosus*). Soybean stalk weevil (*Stemechus subsignatus*). Sugarcane Weevil (*Sphenophorus levis*), *Scepticus gniseus, Scepticus unifonriis, Zabrbtes subfasciatus, Tomicus piniperda*, Coffee Berry Borer (*Hypothenemtis hampei*), *Aracanthus* spp. such as *Aracanthus inburei*, and Cotton root borer (*Eutinobothms brasiliensis*); Tenebrionidae such as *Tribolium castanetim* and *Tribolium confiisum*; Coccinellidae such as *Epilachna vigintibctopunctata*; Bostrychidae such as *Lyctus brunneus*; Ptinidae; Cerambycidae such as *Anoplophbra malasiaca* and *Migdolus fryanus*; Elateridae such as *Melanotus okinawensis, Agriotes fuscicollis, Melanotus legatus, Anchastus* spp., *Conoderus* spp., *Ctenicera* spp., *Limonius* spp., and *Aeolus* spp.; Staphylinidae such as *Paederus fuscipes*; Dennestidae such as *Anthrenus verbasci* and *Dermestes maculates*, and Anobidae such as *Lasibderma serricome* and *Stegobium paniceum.*

Orthoptera: Acrididae such as *Locusta migratoria, Dociostaurus maroecanus, Chortoicetes terminifera, Nlomadacris septemfasciata*, Brown Locust (*Locustana pardalina*), Tree Locust (*Anacridium melanorhodon*), Italian Locust (*Calliptamus italicus*). Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*). Clearwinged grasshopper (*Camnula pellucida*), *Schistocerca gregaria.* Yellow-winged locust (*Gastrimargus musicus*). Spur-throated locust (*Austracris guttulosa*), *Oxya yezoensis, Oxya japonica*, and *Patanga succincta*; Gryllbtalpidae such as *Gryilotalpa orientalis*; Gryllidae such as *Acheta domestica* and *Teleogryllus emma*; and Tettigoniidae such as Mormon cricket (*Anabrus simplex*).

Hymehoptera: Tenthredinidae such as *Athalia rosae* and *Athalia japonica*; Formicidae, for example, *Solenopsis* spp. such as *Solenopsis invicta* and *Solenopsis geminata, Atta* spp. such as Brown leaf-cutting ant (*Atta capiguara*), *Acromyrmex* spp., *Paraponera clavata, Ochetellus glaber, Monomorium pharaonis, Lihepithema humile, Formica firsca japonica, Prjstomyrmex punctutus, Pheidole noda, Pheidole megacephala, Camponotus* spp, such as *Camponotus japonicus* and *Camponotus obscuripes, Pogonomyrmex* such as *Pogonomyrmex* occidental is, Wasmania such as *Wasmania auropunctata*, and *Anoplplepis gracilipes*; Vespidae such as *Vespa mandarinia japonica, Vespa simillima, Vespa analis Fabriciusi, Vespa velutina*, and *Polistes jokahamae*; Siricidae such as *Urocerus gigas*, and Bethylidae.

Blattodea: Blattellidae such as *Blattella germanica*; Blattidae such as *Periplaneta fuliginosa, Periplaneta americana, Periplaneta brunnea*, and *Blatta orientalis*; and Termitidae such as *Reticulitermes speratus. Coptotermes formosanus, Incisitermes minor, Ctyptotermes domesticus, Qdontotermes formosanus, Neotermes koshunensis, Glyptotermes satsuinehsis, Glyptotermcs nakajimai, Glyptotermes fuscus, Hodotermopsis sjostedti, Coptotermes guangzhpuensis, Reticulitennes aniamianus. Reticuliiermes miyatakei, Reticulitermes karimdhehsis; Nasutiterines takasagdensis, Pericapriterrnes nitobei, Sinocapritcrmes mushae*, and *Comitermes cumulans.*

Siphonaptera: *Ctenocephalidae felis, Ctenocephalides canis, Pulex irritans, Xeiropsylla cheopis, Tunga penetrans, Echidridphaga gallinacea, Ndsopsyllus fasciatus*, and tire like.

Phthiraptera: *Haenratdpinus suis, Haematopinus eurystemus, Dalmalinia ovis, Linognathus seypsus, Pediculus humanis, Pediculuc hunranus corporis, Pediculus humanus hunranus*, and *Phthiras pubis*.

Malloplragda: Biting lice which are parasitic on chickens such as *Dalmalinia bovis* and *Lipeurus Caponis, Dalmalinia ovis-Trichodectes canis*, and *Felicola subrostrata*.

Acari: letranychidae such as *Tetranyehus urticae, Tetranychus kanzawai, Tetranychus evansi, Panonyehtis citri, Panonyclrus ulmi* and *Oligonychos* spp.; Eriophyidae such as *Aculops pclekassi. Phylldcoptrutacitri, Aculops lycopersici, Calacarus carinatus, Acaplrylla theavagrans, Eriophycs chibaensis, Aculus schlechtendali Aceria diospyri, Aceria tosichella*, and *Shevtclienkella* sp.; Tarsonenridae such as *Pdlyphagotarsdnenriis latus*; Tenuipalpidae such as *Brevipalpus phoenicis*; Tuckereilidae; Ixodidae such as *Haenraphysalis longicomis, Haenraphysalis flava, Dermacentor taiwanensis, Dernracentor variabilis, Dernracentor andersoni, Ixodes dvatus, Ixodes persulcatus, Ixodes ricinus, Ixodes scapularis, Amblyomma americanum, Ambryomma maculatum, Boophilus microplus, Boophilus annulatus*, and *Rlripicephakis sanguineus*; Acaridae such as *Tyrophagus putrescehtiae* and *Tyrophagus similis*; Pyraglyphidae such as *Dermatophagoidcs farinae* and *Dennatophagoides pteronyssinus*; Cheyletidae such as *Cheyletus eruditus, Cheyletus malaccensis, Cheyletus moorei*, and *Cheyletiella yasguri*; Sarcoptidae such as *Otodectes cynotis* and *Sarcoptes scabiei*; Demodicidae such as *Demodex canis*; Listrophoridae; Haplochthoniidae; Macronyssidae such as *Omithonyssus bacoti* and *Ornithpnysstis sylviarum*; Deirmanyssidae such as *Dermanyssus galiinae*; and Troinbiculidae such as *Leptotrombidium akamushi*.

The harmful-arthropod-controlling composition of the present invention contains the compound of the present invention and an inactive carrier. The harmful-arthropod-controlling composition of tire present invention is usually made into a formulation such as an emulsifiable concentrate, an oil solution, a powder, a granule, a wettable powder, a flowable formulation, a microcapsule, an aerosol, a smoking agent, a poison bait, a resin formulation, a shampoo formulation, a pasty formulation, a foam, a carbon dioxide formulation, and a tablet, by mixing the compound of the present invention with an inactive carrier such as a solid carrier, a liquid carrier, and a gaseous carrier, and, as necessary, adding a surfactant and other adjuvants for formulations. These formulations may be processed into a mosquito repellent coil, ah electric mosquito repellent mat, a liquid mosquito formulation, a smoking agent, a fumigant, a sheet formulation, a spot-on formulation, or a formulation for oral treatment, and used. In addition, the harmful-arthropod-controlling composition of the present invention may be used in admixture with other insecticides, acaricides, nematicides, fungicides, plant growth-regulating agents, herbicides, or synergists.

The harmful-arthropod-controlling composition of the present invention contains the compound of the present invention in an amount of usually 0.01% to 95% by weight with respect to a total weight of the harmful-arthropod-controlling composition.

As the solid carrier used attire time of formulation, for example, fine powders and granular substances such as clays (kaolin day, diatomaceous earth, bentonite, Fubasami clay, acid clay, and the like), synthetic hydrous silicon oxide, talc, ceramics, other inorganic minerals (sericite, quartz, sulfur, activated carbon, calcium carbonate, and the like), and chemical fertilizers (ammonium sulfate, ammonium phosphate, ammonium nitrate, urea, ammonium chloride, and the like), or die like, and synthetic resins (polyester resins such as polypropylene, polyacrylonitrile, polymethyl methacrylate, and polyethylene terephthalate, nylon resins such as nylon-6, nylon-11, and nylon-66, polyamide resin, polyvinyl chloride, polyvinylidene chloride, vinyl chloride-propylene copolymer, and the like) can be mentioned.

As the liquid carrier, for example, water, alcohols (methanol, ethanol, isopropyl alcohol, butanol, hexanol, benzyl alcohol, ethylene glycol, propylene glycol, phenoxyethanol, and the like), ketones (acetone, methyl ethyl ketone, cyclohexanone, and the like), aromatic hydrocarbons (toluene, xylene, ethylbenzene, dodecylbenzene, phenylxylylethane, methylnaphthalene, and the like), aliphatic hydrocarbons (hexane, cyclohexane, kerosene, light oil, and the like), esters (ethyl acetate, butyl acetate, isopropyl myristate, ethyl oleate, diisopropyl adipate, diisobutyl adipate, propylene glycol monomethyl ether acetate, and the like), nitriles (acetonitrile, isobutylnitrile, and the like), ethers (diisopropyl ether, 1,4-dioxane, DME, diethylene glycol dimethyl ether, diethylene glycol monomethyl ether, propylene glycol monomethyl ether, dipropylene glycol monomethyl ether, 3-methoxy-3-methyl-1-butanol, and the like), amides (DMF, dimethylacetamide, and the like), sulfoxides (DMSO and the like), propylene carbonate, and vegetable oils (soybean oil, cottonseed oil, and the like) can be mentioned.

As the gaseous carrier, for example, fluorocarbon, butane gas, liquefied petroleum gas (LPG), dimethyl ether, and carbon dioxide gas can be mentioned:

As the surfactant, for example, nonionic surfactants such as polyoxyethylene alkyl ether, polyoxyethylene alkylaryl ether, and polyethylene glycol fatty acid ester, and anionic surfactants such as alkylsulfonate, alkylbenzenesulfonate, and alkylsulfate can be mentioned.

As the other adjuvants for formulations, a fixing agent, a dispersing agent, a coloring agent, a stabilizer, and the like can be mentioned, and, specifically, for example, casein, gelatin, saccharides (starch, gum arabic, cellulose derivatives, alginic acid, and the like), lignin derivatives, bentonite, synthetic water-soluble polymers (polyvinyl alcohol, polyvinyl pyrrolidone, polyacrylic acids, and the like), acidic phosphate isopropyl, 2,6-di-tert-butyl-4-methylphenol, and BHA (a mixture of 2-tert-butyl-4-methoxyphenol and 3-tert-butyl-4-methoxyphenol) can be mentioned.

As a base material of the resin formulation, for example, vinyl chloride-based polymers, polyurethane, and the like can be mentioned. A plasticizer such as phthalic acid esters (dimethyl phthalate, dioctyl phthalate, and the like), adipic acid esters, and stearic acid may be added as necessary to these base materials. The resin formulation can be obtained by kneading the compound of the present invention in the base material using an ordinary kneading machine and then performing molding by injection molding, extrusion molding, press molding, or the like, and, as necessary, can be further processed into a resin formulation having a shape such as a plate, a film, a tape, a net, and a string through steps such as molding and cutting. These resin formulations are processed, for example, as animal collars, animal ear tags, sheet formulations, attractant strings, or gardening supports.

A base material of the poison bait for example, a cereal powder, vegetable oil, sugar, crystalline cellulose, and the like can be mentioned, and, as necessary, an antioxidant such as dibutylhydroxytoluene and nordihydroguaiaretic acid, a preservative such as dehydroacetic acid, an agent which prevents children and pets from eating by mistake such as *capsicum* powder, a vermin-attracting perfume such as a cheese perfume, an onion perfume, and peanut oil can be added thereto.

A method for controlling a harmful arthropod of the present invention is carried out by applying an effective amount of the compound of the present invention directly to the harmful arthropod and/or to a habitat (plants, soil, indoor spaces, animal bodies, or the like) of a harmful organism. In addition, treatments can be performed on seeds. The method for controlling a harmful arthropod of the present invention is usually used in the form of the harmful-arthropod-controlling composition of the present invention.

In a case where the harmful-arthropod-controlling composition of the present invention is-used for controlling a harmful organism in the field of agriculture, an application amount thereof is usually 1 to 10,000 g in an amount of the compound of the present invention per 10,000 m². In a case where seeds are treated, the compound of the present invention is usually applied in an amount range of 0.001 to 100 g per 1 kg of the seeds. In a case of being made into a formulation such as ah emulsifiable concentrate, a wettable powder, and a flowable formulation, the harmful-arthropod-controlling composition of the present invention is usually applied by dilution with water so that an active ingredient concentration is 0.01 to 10,000 ppm. In a case of being made into a formulation such as a granule and a powder, the harmful-arthropod-controlling composition of die present invention is usually applied as it is.

These formulations or water dilutions thereof may be sprayed directly on harmful arthropods or plants such as crops to be protected from the harmful arthropods, or soil of cultivated land may be treated with these formulations or water dilutions thereof in order to control harmful organisms which inhabit the soil.

In addition, a resin formulation which is processed into a sheet or a string can also be applied by a method such as winding crops with the resin formulation, stretching the resin formulation in the vicinity of crops, or spreading the resin formulation on soil around crop roots.

In a case where the harmful-arthropod-controlling composition of the present invention is used for controlling harmful organisms which inhabit a house, in a case of being applied on a surface, ah application amount thereof is usually 0.01 to 1,000 mg, per 1 m² of a treated area, in an amount of the compound of the present invention, and in a case of being applied to a space, the application amount is usually 0.01 to, 500 mg, per 1 m³ of a treated space, in an amount of the compound of the present invention. In a case of being made into a formulation such as an emulsifiable concentrate, a wettable powder, and a flowable formulation, the harmful-arthropod-controlling composition of the present invention is usually applied by dilution with water so that an active ingredient concentration is 0.1 to 10,000 ppm. In a case of being made into a formulation such as an oil solution, an aerosol, a fumigant, and a poison bait the harmful-arthropod-controlling composition of the present invention is usually applied as it is.

In a case of being used for controlling external parasites on livestock such as cattle, horses, pigs, sheep, goats, and chickens, and small animals such as dogs, cats, rats, and mice, the harmful-arthropod-controlling composition of the present invention can be applied to the animals by known veterinary methods. As specific methods, in a case where systemic control is intended, the composition is administered, for example, by way of a tablet, being mixed in feed, a suppository, and injection (intramuscular, subcutaneous, intravenous, intraperitoneal injections, or the like). In a case where non-systemic control is intended, the composition is used, for example, by way of spraying an oil solution or aqueous solution, performing a pour-on or spot-on treatment, washing an animal with a shampoo formulation, or putting a resin formulation, which is made into a collar or ear tag, on an animal. In a case of being administered to an animal body, an amount of the compound of tire present invention is usually in a range of 0.1 to 1.000 mg per 1 kg of a body weight of an animal, In addition, the compound of the present invention can be used as an agent for controlling harmful arthropods in agricultural land such as fields, paddy fields, lawns, and orchards. The compound of the present invention can control harmful arthropods of agricultural land or the like on which plants and the like as mentioned below are cultivated.

Farm crops: Corn, rice, wheat, barley, rye, oat, sorghum, cotton, soybean, peanut, buckwheat, sugarbeet, rapeseed, sunflower, sugarcane, tobacco, and the like:

vegetables: solanaceae vegetables (eggplant, tomato, green pepper, hot pepper, potato, and the like), cucurbitaceae vegetables (cucumber, pumpkin, zucchini, watermelon, melon, and the like), cruciferae vegetables (Japanese radish, turnip, horseradish, kohlrabi, Chinese cabbage, cabbage, brown mustard, broccoli, cauliflower, and tire like), compositae vegetables-(burdock, garland *chrysanthemum*, artichoke, lettuce, and the like), liliaceae vegetables (Welsh onion, onion, garlic, asparagus, and the like), umbelliferae vegetables (carrot, parsley, celery, parsnip, and the like), chenopodiaceae vegetables (spinach, Swiss chard, and the like), labiatae vegetables (Japanese mint, mint, basil, and the like), strawberry, sweat potato, yam, aroid, and the like;

flower plants; foliage plants;

fruit trees: pomaceous fruits (apple, common pear, Japanese pear, Chinese quince, quince, and the like), stone fleshy fruits (peach, plum, nectarine, Japanese plum, cherry, apricot, prune, and the like), citrus plants (Satsuma mandarin, orange, lemon, lime, grapefruits, and the like), nuts (chestnut, walnut, hazel nut, almond, pistachio, cashew nut, macadamia nut, and tire like), berry fruits (blueberry, cranberry, blackberry, raspberry, and the like), grape, persimmon, olive, loquat, banana, coffee, date, coconut, and the like;

trees other than fruit trees: tea, mulberry, flowering trees, street trees (ash tree, birch, dogwood, *eucalyptus*, ginkgo, lilac, maple tree, oak, poplar, *cercis*, Chinese sweet gum, plane tree, zelkova, Japanese arborvitae, fir tree, Japanese hemlock, needle juniper, pine, spruce, yew), and the like.

The plants also include genetically modified crops.

EXAMPLES

Hereinafter, the present invention will be described in more detail by way of production examples, formulation examples, test examples, and the like. However, the present invention is not limited to only these examples.

First, production examples of the present compound are shown.

LC-MS Analysis Conditions

Measurement Condition A

LCMS: Column—Zorbax Extend C18 (50×4.6 mm, 5 u, 80 A), (mobile phase: from 90% [10 mM NH$_4$OAc in water] and 10% [CH$_3$CN] to 70% [10 mM NH$_4$OAc in water] and 30% [CH$_3$CN] in 1.5 min, further to 10% [10 mM NH$_4$OAc in water] and 90% [CH$_3$CN] in 3.0 mm, held this mobile phase composition up to 4.0 min and finally back to initial condition in 5.0 min). Flow=1.2 ml/min Measurement Condition B Column—X-Bridge C18 (50×4.6 mm, 5 u), (mobile phase: from 90% [10 mM NH₄OAc in water] and 10% [CH₃CN] to 70% [10 mM NH₄OAc in water] and 30% [CH₃CN] in 1.5 min, further to 10% [10 mM NH₃OAc in water] and 90% [CH₃CN] in 3.0 min, held this mobile phase composition up to 4.0 min and finally back to initial condition in 5.0 min). Flow=1.2 ml/min Measurement Condition C L-Column2 ODS (35×4.6 mm), (mobile phase: front 90% [0.1% HCOOH in water] and 10% [0.1% HCOOH in CH₃CN] to 100% [0.1% HCOOH in CH₃CN] in 2.0 min, held this mobile phase composition up to 4.0 min and finally back to initial condition in 5.0 min). Flow=1.0 ml/min Measurement Condition D LCMS: Column—YMC-TRIART C18 (33×2.1 min, 3 u), (mobile phase: 98% [0.05% HCOOH in water] and 2% [CH₃CN] held for 0.75 min, then to 90% [0.05% HCOOH in water] and 10% [CH₃CN] in 1.0 min, further to 2% [0.05% HCOOH in water] and 98% [CH₃CN] in 2.0 min, held this mobile phase composition up to 2.25 min and finally back to initial condition in 3.0 min). Flow=1.0 ml/min.

Reference Production Example 1

To a mixture of 20 g of 2-cyano-5-(2,2,3,3-pentafluoropropoxy)pyridine and 200 mL of THF was added dropwise 87 mL of methylmagnesium bromide under ice-cooling, and the mixture was stirred for 30 minutes. To this mixture was added 50 mL of 1 N hydrochloric acid, and the mixture was stirred for 1 hour. The mixture was extracted with MTBE and the obtained organic layer was dried over sodium sulfate and concentrated under reduced pressure. The obtained residue was subjected to silica gel column chromatography to obtain 20 g of Intermediate 2 represented by the following formula.

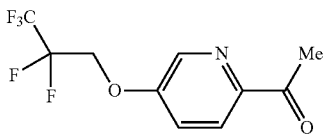 [SMILES: CC(=O)c1ccc(OCC(F)(F)C(F)(F)F)cn1]

Intermediate 2: ¹H-NMR (CDCl₃) δ: 8.39 (1H, d), 8.08 (1H, t), 7.34 (1H, dd), 4.55 (2H, td), 2.70 (3H, s).

Reference Production Example 2

To a mixture of 17.5 g of intermediate 2 and 50 mL of acetic acid was added 3 mL of an acetic acid solution of 25% hydrogen bromide at room temperature, and then 3.6 mL of bromine was added thereto. The mixture was stirred at 100° C. for 1 hour. The mixture was concentrated under reduced pressure. To the obtained residue was added a saturated aqueous sodium bicarbonate solution, and the mixture was extracted with ethyl acetate. The obtained organic layer was dried over sodium sulfate and concentrated under reduced pressure, to obtain 14 g of Intermediate 3 represented by the following formula.

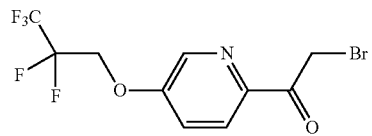 [SMILES: O=C(CBr)c1ccc(OCC(F)(F)C(F)(F)F)cn1]

Intermediate 3: ¹H-NMR (CDCl₃) δ: 8:40 (1H, d), 8.14 (1H, d), 7=37 (1H, dd), 4.80 (2H, s), 4.56 (2H, t).

Reference Production Example 3

To a mixture of 2.2 g of Intermediate 3 and 5 mL of acetonitrile was added 0:9 g of 5-(trifluoromethyl)-2-aminopyridine at room temperature, and the mixture was refluxed for 3 hours. To the mixture was added water, and the mixture was extracted with ethyl acetate. The obtained organic layer was dried over sodium sulfate and concentrated under reduced pressure. The obtained residue was subjected to silica gel column chromatography to obtain 0.43 g of Intermediate 4 represented by the following formula.

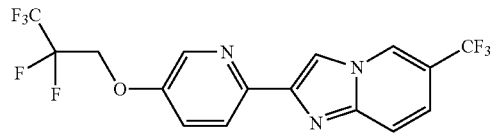 [SMILES: FC(F)(F)c1ccc2nc(-c3ccc(OCC(F)(F)C(F)(F)F)cn3)cn2c1]

Intermediate 4: ¹H-NMR (CDCl₃) δ: 8.52 (1H, t), 8.40 (1H, d), 8.27 (1H, d), 8.18 (1H, d), 7.73 (1H, dd), 2.38 (1H, dd), 7.37-7.33 (1H, dd), 4.53 (2H, td).

Reference Production Example 4

Compounds produced according to the method described in Reference Production Example 3 and physical property values thereof are shown below.

Compounds represented by Formula (A-1) in which a combination of T, G¹, G², G³ and G⁴ is any one of the combinations described in Table 16.

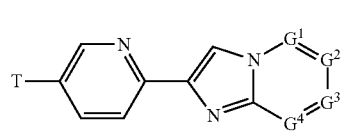

TABLE 16

| Intermediate | T | G¹ | G² | G³ | G⁴ |
|---|---|---|---|---|---|
| 5 | OCH₂CF₂CF₃ | CH | CH | CCF₃ | CH |
| 8 | OCH₂CF₂CF₃ | CH | CH | CH | CH |
| 24 | OCH₂CF₂CF₃ | N | CCF₃ | CH | CH |
| 25 | OCH₂CF₂CF₃ | CH | CCF₃ | CH | N |
| 26 | OCH₂CF₂CF₃ | CH | CH | CCF₃ | N |
| 27 | OCH₂CF₂CF₃ | CH | CH | CBr | CH |
| 62 | OCH₂CF₂CF₃ | CH | CBr | CH | CH |
| 63 | OCH₂CF₂CF₃ | CH | CH | CCl | N |

Intermediate 5: ¹H-NMR (CDCl₃) δ: 8.39 (1H, d), 8:29 (Hi s), 8.26 (1H, d), 8.20 (1H, d), 7.95 (1H, d), 7.39 (1H, dd), 6.99 (1H, dd), 4.53 (2a td).

Intermediate 8: ¹H-NMR (CDCl₃) δ: 8.37 (1H, d), 8.17 (3H, dt), 7.63 (1H, d), 7.36 (1H, td), 7.20 (1H, t), 6.81 (1H, t), 4:52 (2H, t).

Intermediate 24: ¹H-NMR (CDCl₃) δ: 4.52 (2H, t), 7.32-7.39 (2H, m), 8.08-8.19 (2H, m), 8.42 (1H, d), 8.64 (1H, s).

Intermediate 25: ¹H-NMR (CDCl₃) δ: 4.52 (2H, t), 7.37-7.39 (1H, m), 8.26 (1H, s), 8:33 (1H, d), 838 (1H, s), 8.71 (1H, s), 8.99 (1H, s).

Intermediate 26-¹H-NMR (CDCl₃) δ: 4:52 (2111), 7.21 (ill s), 7.39 (1H, d), 8:314.38 (3H, m), 8.63 (1 Hid), Intermediate 27: ¹H-NMR (CDCl₃) δ: 4.50 (2H, t), 6.90 (1H, d), 7.35 (1H, d), 7.79 (1H, s), 8.00 (1H, d), 8.11-8.13 (2H, m), 8.36 (1H, s).

Intermediate 62: ¹H-NMR (CDCl₃) δ: 4.43-4.79 (2H, m), 7.20-7.25 (1H, m), 7.35 (1H, dd), 7.48-7.52 (1H, m), 8.12 (2H, t), 8.29 (1H, s), 836 (1H, d).

Intermediate 63: ¹H-NMR (CDCl₃) δ: 4.51 (2H, f), 6.90 (1H, d), 7.36 (1H, d), 8.11 (1H, s), 8.26-8.28 (1H, m), 8.36-8.40 (2H, m).

Reference Production Example 5

To a mixture of 0.79 g of Intermediate 4 and 7 mL of DMF was added 0.52 g of N-iodosuccinimide under, ice-cooling, and the mixture was stirred at room temperature for 12 hours. To the mixture was added water, and the mixture was extracted with MTBE. The obtained organic layer was dried over sodium sulfate and concentrated under reduced pressure. The obtained residue was subjected to silica gel column chromatography to obtain 0.94 g of intermediate 6 represented by the following formula.

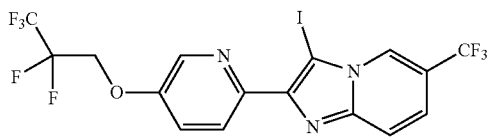

Intermediate 6: ¹H-NMR (CDCl₃) δ: 8.67 (1H, d), 8.52 (1H, d), 8.24 (1H, d), 7.72 (1H, d), 7.43 (1H, t), 7.40 (1H, t), 4.55 (2H, t), Reference Production Example 6

Compounds produced according to foe method described in Reference Production Example 5 and physical property values thereof are shown below.

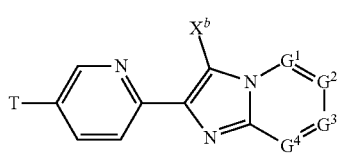

(A-2)

Compounds represented by Formula (A-2) in which a combination of T, X^b, G¹, G², G³, and G⁴ is any one of the combinations described in Table 17.

TABLE 17

| Intermediate | T | X^b | G¹ | G² | G³ | G⁴ |
|---|---|---|---|---|---|---|
| 7 | OCH₂CF₂CF₃ | I | CH | CH | CCF₃ | CH |
| 9 | OCH₂CF₂CF₃ | I | CH | CH | CH | CH |
| 31 | OCH₂CF₂CF₃ | I | N | CCF₃ | CH | CH |
| 32 | OCH₂CF₂CF₃ | I | CH | CCF₃ | CH | N |

TABLE 17-continued

| Intermediate | T | X^b | G¹ | G² | G³ | G⁴ |
|---|---|---|---|---|---|---|
| 33 | OCH₂CF₂CF₃ | I | CH | CH | CCF₃ | N |
| 34 | OCH₂CF₂CF₃ | I | CH | CH | CBr | CH |
| 35 | OCH₂CF₂CF₃ | I | CH | CCH₃ | CH | CH |
| 36 | OCH₂CF₂CF₃ | I | CH | ⟨pyrimidine⟩ | CH | CH |
| 37 | OCH₂CF₂CF₃ | I | CH | CH | Cc-Pr | CH |
| 64 | OCH₂CF₂CF₃ | I | CH | CH | COCH₃ | N |

Intermediate 7: ¹H-NMR (CDCl₃) δ:8.51 (1H, d), 8.43 (1H, d), 8.25 (1H, d), 7.93 (1H, d), 7.41 (1H, dd), 7.12 (1H, dd), 4.56 (2H, t).

Intermediate 9: ¹H-NMR (CDCl₃) δ: 8.50 (1H, d) 8.31 (1H, dd), 8.23 (1H, d), 7.62 (1H, t), 7.39 (1H, dd), 7.29 (1H, ddd), 6.96 (1H, td, J=6.8), 4.54 (2H, dd).

Intermediate 31: ¹H-NMR (GDCl₃) δ: 4.55 (2H, t), 7.39-7.42 (2H, m), 8.08 (1H, d), 8.28 (1H, d), 8.54 (1H, d).

Intermediate 32: ¹H-NMR (CDCl₃) δ: 4.54 (2H, t), 7.40 (1H, d) 8.40 (1H, d), 8.50 (1H, s), 8.71 (1H, s), 8.88 (1H, s).

Intermediate 33: ¹H-NMR (CDCl₃) δ: 5.07 (2H, t), 7.57 (1H, d) 7.73 (1H, d), 8.24 (1H, d), 8.59 (1H, s), 9.14 (1H, d).

Intermediate 34: ¹H-NMR (CDCl₃) δ: 4.53 (2H, t), 7.02 (1H, d), 7.35-7.38 (1H, m), 7.79 (1H, s), 8.15-8.20 (2H, m), 8.48 (1H, s).

Intermediate 35: LCMS (measurement condition B): RT=3:39 min (260 nm), MS found: 548:3 [M+H].

Intermediate 36: LCMS (measurement condition A): RT=3.76 min (260 nm), MS found: 483.8 [M+H].

Intermediate 37: LCMS (measurement condition B): RT=3:93 min (260 nm) MS found: 509.6 [M+H].

Intermediate 64: LCMS (measurement condition A): RT=3:50 min (260 nm), MS found: 500.8 [M+H], Intermediate 18 represented by tire following formula

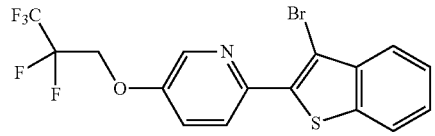

Intermediate 18: ¹H-NMR (CDCl₃) δ: 8.48 (1H, d), 8.44 (1H, d), 7.90-7.83 (2H, m), 7.49-7.38 (3H, m), 4.55 (2H, t).

Intermediate 19 represented by die following formula

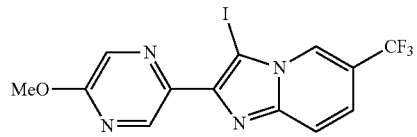 [SMILES: COc1cnc(-c2nc3ccc(C(F)(F)F)cn3c2I)cn1]

Intermediate 19: ¹H-NMR (CDCl₃) δ: 8.99 (1H, d), 8.64 (1H, s), 8.35 (1H, d), 7.73 (1H, d), 7.43 (1H, dd), 4.04 (3H, s), Reference Production Example 7

To a mixture of 11.4 g of Intermediate 3, 15 g of potassium carbonate, and 130 mL of THF was added dropwise 3.2 mL of ethanethiol, and the mixture was stirred for 4.5 hours. To the mixture was added water, and the mixture was extracted with MTBE. The obtained organic layer was dried over sodium sulfate and concentrated under reduced pressure. The Obtained residue was subjected to silica-gel column chromatography to obtain 9.57 g of Intermediate 10 represented by the following formula.

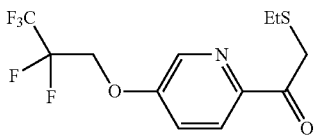

Intermediate 10: (CDCl$_3$) δ: 8.39 (1H, d) 8.13 (1H, d), 7.36 (1H, dd), 4:55 (2H, td), 4.01 (2H, s) 2.60 (2H, q), 1.27 (3H, f).

Reference Production Example 8

Compounds produced according to the method described in Reference Production Example 7 and physical property values thereof are shown below.

Intermediate 11 represented by the following formula

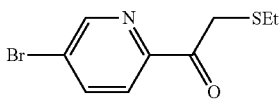

Intermediate 11: $^1$H-NMR (CDCl$_3$) δ:8.73 (1H, t), 7.98 (2H, d), 4.00 (2H, t), 2.58 (2H, q), 1.27 (3H, t).

Reference Production Example 9

To a mixture of 9.57 g of Intermediate 10, 4.5 mL of triethylamine, and 150 mL of chloroform was added dropwise 5.5 mL of trimethylsilyl triflate which had been cooled to −20° C., and the mixture was stirred at room temperature for 30 minutes. The mixture was brought to −20° C., 11.5 g of trimethylphenyl tribromide was added thereto and the mixture was stirred at room temperature for 2 hours. To this mixture was added water, and the mixture was extracted with MTBE. The obtained organic layer was dried over sodium sulfate and concentrated under reduced pressure, to obtain 14 g of intermediate 12 represented by the following formula.

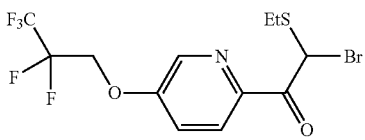

Intermediate 12: $^1$H-NMR (CDCl$_3$) δ: 8.39 (1H, dd), 8.18 (1H, dd), 7.40-7.36 (1H, m), 6.15 (1H, s), 4.56 (2H, td), 2.71 (2H, dtt), 1.27 (3H, t).

Reference Production Example 10

Compounds produced according to the method described in Reference Production Example 9 and physical property values thereof are shown below.

Intermediate 13 represented by the following formula

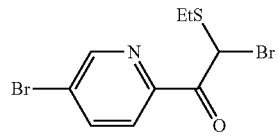

Intermediate 13: $^1$H-NMR (CDCl$_3$) δ: 8.74 (1H, dd), 8.04 (2H, s), 7.19 (1H, s), 2.94-2.77 (2H, m), 1.35 (3H, t).

Reference Production Example 11

Compounds produced according to the method described in Reference Production Example 3 and physical property val ties thereof are shown below.

Intermediate 14 represented by the following formula

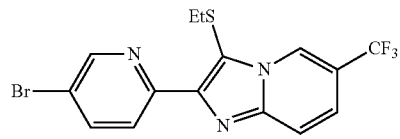

Intermediate 14: $^1$H-NMR (CDCl$_3$) δ: 8.90 (2H, % 8.31 (1H, d), 195 (1H, ddz), 7.78 (1H, d), 7.45 (1H, dd), 2.92 (2H, q), 1.16 (3H, t).

Intermediate 15 represented by the following formula

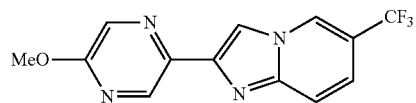

Intermediate 15: $^1$H-NMR (CDCl$_3$) δ: 8.93 (1H, d), 8.52 (1H, s), 8.23 (2H, t), 7:74 (1H, d), 7.35 (1H, dd), 4.04 (3H, s).

Reference Production Example 12

To a mixture of 0.8 g of Intermediate 14 and 8 mL of chloroform was added 1.03 g of 70% mCPBA under ice-cooling, and the mixture was stirred at room temperature for 6 hours. To the mixture were added a saturated sodium hydrogen carbonate aqueous solution and a sodium thiosulfate aqueous solution, and the mixture was extracted with chloroform. The obtained organic layer was dried over sodium sulfate and concentrated under reduced pressure. The obtained residue was subjected to silica gel column chromatography to obtain 0.56 g of Intermediate 16 represented by the following formula.

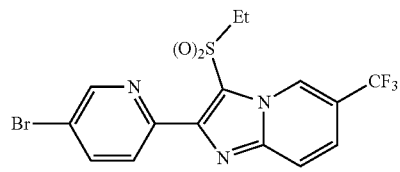

Intermediate 16: ¹H-NMR (CDCl₃) δ: 9.67 (1H, s), 8.78 (1H, t), 8.01 (2H, dd), 7.87 (1H, d), 7.63 (1H, dd), 3.99 (2H, q), 1.42 (3H, t), Reference Production Example 13

A mixture of 0.77 g of 2-bromo-5-(2,2,3,3,3-pentafluoropropoxy)pyridine, 0.2 g of [1,1'-bis(diphenylphosphino)ferrocene]palladium (II) dichloride, 1.6 g of tripotassium phosphate, 0.67 g of benzo[b]thiophen-2-ylboronic acid, 0.5 ml of water, and 5 ml of DME was stirred under a nitrogen atmosphere at 85° C. for 3 hours. To the mixture was added water, and the mixture was extracted with MTBE. The obtained organic layer was dried over, sodium sulfate and concentrated under reduced pressure, the obtained residue was subjected to silica gel column chromatography to obtain 0.586 g of Intermediate 17 represented by the following formula.

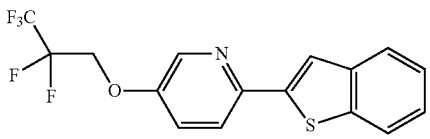 [SMILES: FC(F)(F)C(F)(F)COc1ccc(-c2cc3ccccc3s2)nc1]

Intermediate 17: ¹H-NMR (CDCl₃) δ: 8.38 (1H, d), 7.86 (1H, dd), 7.79 (1H, q), 7.74 (1H, s), 7.38-7:32 (4H, m), 4.52 (2H, dd).

Reference Production Example 14

A mixture of 3.0 g of Intermediate 19, 10 mL of 1,4-dioxane, 1:3 g of tris(dibenzylideneacetone)dipalladium (0), 1.7 g of xantphos, 3.7 mL of diisopropylethylamine, and 0.81 mL of ethanethiol was stirred, under reflux for 90 minutes. To the mixture was added water, and the mixture was extracted with MTBE. The obtained organic layer was dried over sodium sulfate; and concentrated under reduced pressure. The obtained residue was subjected to silica gel column chromatography to obtain 0.85 g of Intermediate 20 represented by the following formula.

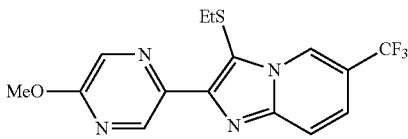

Intermediate 20: ¹H-NMR (CDCl³) δ:9.17 (1H, d), 8.92 (1H, s), 8.41 (1H, d), 7.79 (1H, d), 7.45 (1H, dd), 4.06 (3H, s), 2.87 (2H, q), 1.18 (3H, t).

Reference Production Example 15

A mixture of 0.85 g of Intermediate 20 and 20 ML of 12 N hydrochloric acid was stirred at 80° C. for 1 hour. The mixture was allowed to cool to room temperature, alkalified by adding a saturated sodium hydrogen carbonate aqueous solution, and extracted with ethyl acetate. The obtained organic layer was dried over anhydrous sodium sulfate and concentrated under reduced pressure, to obtain 1.28 g of crude product of intermediate 21 represented by the following formula.

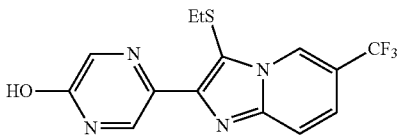

Intermediate 21: ¹H-NMR (CDCl₃) δ: 10.60 (1H, br s), 8.88 (1H, s), 8.43 (1H, s), 8.09 (1H, s), 7.74 (1H, d), 7.45 (1H, d), 2.86 (2H, d), 1.19 (3H, t), Reference Production Example 16

A mixture of 1.28 g of the crude product of Intermediate 21 obtained in Reference Production Example 15, 5 mL of phosphorus oxychloride, and 10 mL of toluene was stirred at 100° C. for 2 hours. The obtained mixture was allowed to cool to room temperature and concentrated under reduced pressure. To the obtained residue was added water, and the mixture was extracted with chloroform. The Obtained organic layer was dried over anhydrous sodium sulfate and concentrated under reduced pressure, to obtain 0.74 g of Intermediate 22 represented by the following formula.

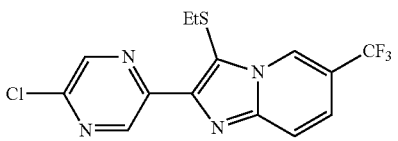

Intermediate 22: ¹H-NMR (CDCl₃) δ: 9.42 (1H, d), 8.94 (1H, s), 8.76 (1H, d), 7.81 (1H, d), 7.49 (1H, dd), 2.92 (2H, q), 1.19 (3H, t).

Reference Production Example 17

Intermediate 23 represented by the following formula was obtained according to the method described in Reference Production Example T2, using Intermediate 22 in place of intermediate 14.

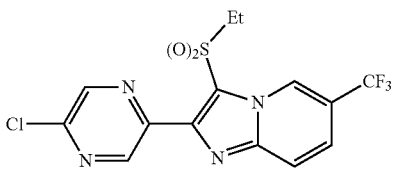

Intermediate 23: ¹H-NMR (CDCl₃) δ: 9.64 (1H, t), 9.13 (1H, t), 8.68 (1H, d), 7.91 (1H, d), 7.67 (1H, dd), 3.89 (2H, q), 1.43 (3H, t).

Reference Production Example 18

Under a nitrogen atmosphere, a mixture of 509 mg of Intermediate 16, 400 mg of bis(pinacolato)diboron, 100 mg of [1,1-bis(diphenylphosphino)]palladium dichloride, 340 mg of potassium acetate, and 5 mL of dioxane was, stirred at 80° C. for 1 hour. The obtained mixture was allowed to cool to room temperature and concentrated under reduced pressure. To the obtained residue were added 5 mL of acetone and 2 mL of water, and 1.44 g of oxone was added thereto under ice-cooling. The obtained mixture was stirred at room temperature for 3 hours. To the obtained mixture was added saturated saline, and the mixture was extracted with ethyl acetate. The obtained organic layer was dried over anhydrous sodium sulfate and concentrated under reduced pressure, to obtain 0.5 g of Intermediate 38 represented by the following formula, as a crude product.

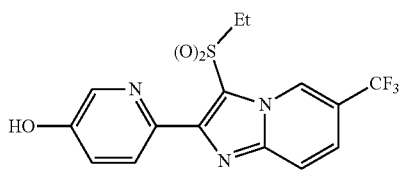

Intermediate 38 LCMS (measurement condition C): RT+1:63 min (252 nm) MS found: 372.6 [M+H].

Reference Production Example 19

A mixture of 1.0 g of Intermediate 62, 274 mg of tetrakis(triphenylphosphine)palladium, 753 mg of sodium carbonate, 437 mg of pyrimidin-5-ylboronic acid, 4 mL of water, and 16 mL of 1,4-dioxane was stirred at 100° C. for 16 hours under a nitrogen atmosphere. To the obtained mixture was added water, and the mixture was extracted with ethyl acetate. The obtained organic layer was dried over sodium sulfate and concentrated under reduced pressure. The obtained residue was subjected to alumina column chromatography/to obtain 700 mg of Intermediate 28 represented by the following formula:

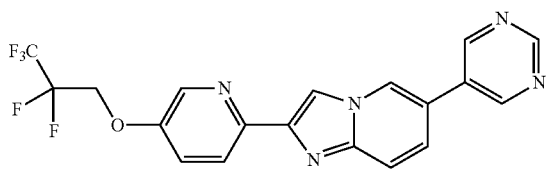 [SMILES: FC(F)(F)C(F)(F)COc1ccc(-c2cn3cc(-c4cncnc4)ccc3n2)nc1]

Intermediate 28: $^1$H-NMR (CDCl$_3$) δ: 5.02 (2H, t, J=13.6 Hz), 7.55-7.68 (2H, m, 7.76 (2H, S), 8.12 (1H, d, J=8.6 Hz), 8.43 (2H, d, J=17.2 Hz), 9.15-9.22 (3H, m).

Reference Production Example 20

Compounds produced according to the method described in Reference Production Example 19 and physical property values thereof are shown below. Compounds represented by Formula (A-1) in which a combination of T, G$^1$, G$^2$, G$^3$, and G$^4$ is any one of the combinations described in Table 18.

TABLE 18

| Intermediate | T | G$^1$ | G$^2$ | G$^3$ | G$^4$ |
|---|---|---|---|---|---|
| 29 | OCH$_2$CF$_2$CF$_3$ | CH | CCH$_3$ | CH | CH |
| 30 | OCH$_2$CF$_2$CF$_3$ | CH | CH | Cc-Pr | CH |

Intermediate 29: LCMS (measurement condition 8): RT=3:43 min (260 nm), MS found: 357.8 [M+H].

Intermediate 30:1 CMS (measurement condition B): RT=3.57 min (260 nm). MS found: 383.7 [M+H], Reference Production Example 21

Compounds produced according to the method described in Reference Production Example 3 and physical property values thereof are shown below.

Compounds represented by Formula (A-#) in which a combination of G$^1$, G$^2$, G$^3$, and G$^4$ is any one of the combinations described in Table 19.

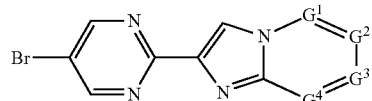

TABLE 19

| Intermediate | G$^1$ | G$^2$ | G$^3$ | G$^4$ |
|---|---|---|---|---|
| 39 | CH | CH | CH | CH |
| 40 | CH | CCF$_3$ | CH | CH |
| 66 | N | CCF$_3$ | CH | CH |

Intermediate 39: $^1$H-NMR (CDCl$_3$) δ: 6.83 (1H, t), 7.20 (1H, t), 7.68 (1H, d), 8.14 (1H, d), 8.34 (1H, s), 8.84 (2H, s).

Intermediate 40: $^1$H-NMR (CDCl$_3$) δ: 7.36 (1H, d), 7.80 (1H, d), 8.45 (1H, s), 8.53 (1H, s), 8.87 (2H, s).

Intermediate 66: $^1$H-NMR (CDCl$_3$) δ: 7.38 (1H, d), 8.19 (1H, d), 8.82 (1H, s), 8.91 (2H, s).

Reference Production Example 22

Compounds produced according to the method described in Reference Production Example 19 and physical property values thereof are shown, below.

Compounds represented by Formula (A-9) in which a combination of T, G$^1$, G$^2$, G$^3$, and G$^4$ is any one of the combinations described in Table 20.

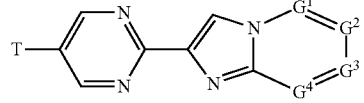

TABLE 20

| Intermediate | T | G$^1$ | G$^2$ | G$^3$ | G$^4$ |
|---|---|---|---|---|---|
| 41 | 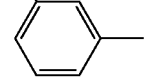 | CH | CH | CH | CH |
| 42 | 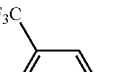 | CH | CH | CH | CH |
| 43 | 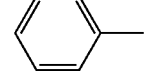 | CH | CCF$_3$ | CH | CH |

TABLE 20-continued

| Intermediate | T | G¹ | G² | G³ | G⁴ |
|---|---|---|---|---|---|
| 44 | 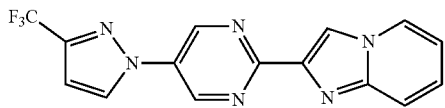 | CH | CCF₃ | CH | CH |

Intermediate 41: ¹H-NMR (CDCl₃) δ: 7.31-7.34 (1H, m), 7.46-7.54 (4H, m), 7.61 (1H, d), 7.77 (1H, d), 8:48-8.53 (2H, m), 9.01 (2H, s).

Intermediate 42: ¹H-NMR (CDCl₃) δ: 7.36-7.40 (2H, m), 7.54-7.59 (2H, m), 8.53-8.56 (2H, m), 8.77 (2H, d), 9.09 (2H, s).

Intermediate 43: ¹H-NMR(CDCl₃) δ: 735-7.38 (1H, dd), 7.65-7.69 (1H, m), 7.72-7.74 (1H, m), 7.76-7.89 (3H, m), 8.52 (1H, s), 8.56 (1H, s), 9.05 (2H, s).

Intermediate 44: ¹H-NMR (CDCl₃) δ: 7.38 (1H, m), 7.54-7.59 (1H, m), 7:83 (1H, d), 8.15 (1H, s), 8.54-8.57 (2H, m), 8.99 (1H, s), 9.08 (2H, s).

Reference Production Example 23

To a mixture of 900 mg of intermediate 39, 883 mg of 3-(trifluoromethyl)imidazole, and 10 mL of DMF were added sequentially 3.2 g of cesium carbonate, 0.1 mL of trans-N,N'-dimethylcyclohexane-1,2-diamine, and 0.125 g of copper iodide, and the mixture was stirred at 140° C. for 24 hours. The mixture was cooled to room temperature, water was added thereto, and the mixture was extracted with ethyl acetate. The obtained organic layer was washed with saturated saline, dried over anhydrous sodium sulfate, and concentrated under reduced pressure. The obtained residue was subjected to alumina chromatography (hexane:ethyl acetate=3:2) to obtain 700 mg of intermediate 45 represented by the following formula.

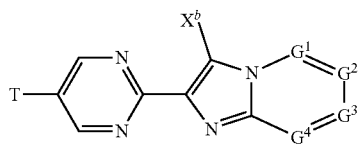

Intermediate 45: ¹H-NMR (CDCl₃) δ: 6:83-6.87 (2H, m), 7.25 (1H, s) 7.71 (1H, d, J=9.2 Hz), 8.05 (1H, s), 8.17 (1H, d, J=6.4 Hz), 8.41 (1H, s), 9.18 (2H, s).

Reference Production Example 24

Compounds produced according to the method described in Reference Production Example 23 and physical properly values thereof are shown below.

Compounds represented by Formula (A-9) in which a combination off. G¹, G², G³, and G⁴ is any one of the combinations described in Table 21,

TABLE 21

| Intermediate | T | G¹ | G² | G³ | G⁴ |
|---|---|---|---|---|---|
| 46 | F₃C-pyrazole | CH | CCF₃ | CH | CH |

Intermediate 46: ¹H-NMR (CDCl₃) δ:6.84 (1H, s), 7.38 (1H, d), 7.82 (1H, d), 8.07 (1H, s), 8.54 (2H, d), 9.22 (2H, s).

Reference Production Example 25

A mixture of 2.5 g of Intermediate 40, 10=9 mL of 2,2,3,3,3-pentafluoropropanol, 692 mg of copper iodide, 1.3 g of 1,10-phenanthroline, 11.8 g of cesium carbonate, and 50 mL of xylene was stirred at 110° C. for 16 hours. To the mixture was added water, and the mixture was extracted with ethyl acetate. The obtained organic layer was dried over sodium sulfate and concentrated under reduced pressure. The obtained residue was subjected to silica gel column chromatography to obtain 1.2 g of Intermediate 47 represented by the following formula.

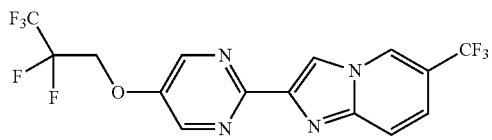 [SMILES: FC(F)(F)c1ccc2nc(-c3ncc(OCC(F)(F)C(F)(F)F)cn3)cn2c1]

Intermediate 47: ¹H-NMR (CDCl₃) δ:4.58 (2H, t, J=11.6 Hz), 7.35 (1H, d, J=9.2 Hz), 7.80 (1H, d, J=9.3 Hz), 8:38 (1H, s), 853-8.56 (3H, m).

Reference Production Example 26

Compounds produced according to the method described in Reference Production Example 25 and physical property values thereof are shown below.

Compounds represented by Formula (A-9) in which a combination of T, G¹, G², G³, and G⁴ is any one of the combinations described in Table 22.

TABLE 22

| Intermediate | T | G¹ | G² | G³ | G⁴ |
|---|---|---|---|---|---|
| 48 | OCH₂CF₂CF₃ | N | CCF₃ | CH | CH |

Intermediate 48: ¹H-NMR (CDCl₃) δ: 4.59 (2H, t), 7.36 (1H, d), 8.18 (1H, d). 8.59 (1H, s), 8.77 (2H, s).

Reference Production Example 27

Compounds produced according to the method described in Reference Production Example 5 and physical property values thereof are shorn below.

Compounds represented by Formula (A-10) in which a combination of T, X^b, G¹, G², G³, and G⁴ is any one of the combinations described in Table 23.

(A-10)

$$\text{T} - \underset{\text{N}}{\overset{\text{X}^b}{\bigcirc}} - \underset{\text{N}}{\bigcirc} \underset{G^4}{\overset{G^1}{\underset{G^3}{\bigcirc}}} G^2$$

TABLE 23

| Intermediate | T | $X^b$ | $G^1$ | $G^2$ | $G^3$ | $G^4$ |
|---|---|---|---|---|---|---|
| 49 | 3-CF₃-phenyl | I | CH | CH | CH | CH |
| 50 | 5-CF₃-pyridin-3-yl | I | CH | CH | CH | CH |
| 51 | 3-CF₃-phenyl | I | CH | CCF₃ | CH | CH |
| 52 | 5-CF₃-pyridin-3-yl | I | CH | CCF₃ | CH | CH |
| 53 | 3-CF₃-pyrazol-1-yl | I | CH | CCF₃ | CH | CH |
| 54 | 3-CF₃-pyrazol-1-yl | I | CH | CCF₃ | CH | CH |
| 55 | OCH₂CF₂CF₃ | I | CH | CCF₃ | CH | CH |
| 56 | OCH₂CF₂CF₃ | I | N | CCF₃ | CH | CH |

Intermediate 49: ¹H-NMR (CDCl₃) δ: 7.43-7.56 (4H, m), 7.66 (2H, d), 7.82 (1H, d), 8.71 (1H, s), 9.14 (2H, s).

Intermediate 50: ¹H-NMR (CDCl₃) δ: 7.67 (1H, d), 7.91 (1H, d), 7.98 (2H, d), 8.74-8.79 (3H, m), 9.45 (2H, s).

Intermediate 51: ¹H-NMR (CDCl₃) δ: 7.45 (1H, d), 7:68-7.70 (1H, m), 7.73 (1H, s), 7.84 (2H, s), 7.89 (1H, s) 8.72 (1H, s), 9.15 (2H, s).

Intermediate 52: ¹H-NMR (CDCl₃) δ: 7.46-7.48 (1H, m), 7.83 (1H, s), 8.02 (1H, s), 8.18 (1H, s), 8.72 (1H, m), 9.01 (1 If, s)>9.12<1H, s), 9.17 (1H, s).

Intermediate 53: ¹H-NMR (CDCl₃) δ: 6.81-6.84 (1H, m), 6.99 (1H, t), 7.32 (1H, t), 7.72 (1H, d), 8.08 (1H, s), 835 (1H, d), 9.29 (2H, s).

Intermediate 54: ¹H-NMR (CDCl₃) δ: 6.85 (1H, s), 7.45-7.50 (1H, m), 7.82 (1H, d), 8.09 (1H, s), 8.71 (1H, s), 9.28-9.33 (2H, s).

Intermediate 55: ¹H-NMR (CDCl₃) δ: 4.60 (2H, t), 7.43 (1H, d), 7.79<1H, d), 8.67-8.68 (3H, m).

Intermediate 56: ¹H-NMR (CDCl₃) δ: 4.61 (2H, t), 7.43 (1H, d), 8.11 (1H, d), 8.67 (2H, s).

Reference Production Example 28

Intermediate 57 represented by the following formula was obtained according to the method described in Reference Production Example 3, using 6-methoxypyridazin-3-amine in place of Intermediate 3.

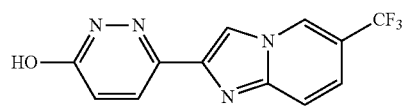 [SMILES: Oc1ccc(-c2cn3cc(C(F)(F)F)ccc3n2)nn1]

Intermediate 57: ¹H-NMR (CDCl₃) δ: 7.08 (1H, d), 736 (1H d), 7.73 (1H, d), 8.12 (1H, s), 8.16 (1H, d), 8.52 (1H, s), 10.93 (1H, brs).

Reference Production Example 29

Intermediate 58 represented by die following formula was obtained according to the method described in Reference Production Example 5, using intermediate 57 in place of Intermediate 4.

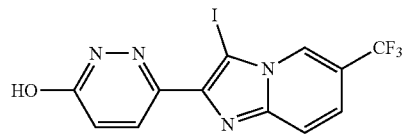 [SMILES: Oc1ccc(-c2nc3ccc(C(F)(F)F)cn3c2I)nn1]

Intermediate 58: ¹H-NMR (DMSO-d₆) δ:1.94 (1H, d), 7.64 (1H, d), 7:86 (1H, d), 8.11 (1H, d), 8.70 (1H, br s), 13.38 (1H, brs).

Reference Production Example 30

Intermediate 59 represented by the following formula was obtained according td the method described in Reference Production Example 14, using Intermediate 58 in place of Intermediate 19,

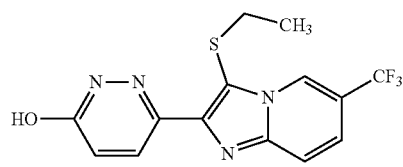 [SMILES: CCSc1c(-c2ccc(O)nn2)nc2ccc(C(F)(F)F)cn12]

Intermediate 59: LCMS (measurement condition D): RT=1.64 min (260 nm), MS found: 341 [M+H], Intermediate 60 represented by the following formula was obtained according to the method described in Reference Production Example 16, using Intermediate 59 in place of Intermediate 21.

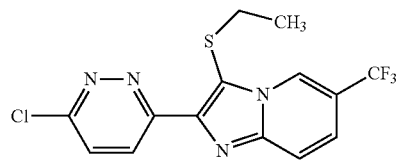 [SMILES: CCSc1c(-c2ccc(Cl)nn2)nc2ccc(C(F)(F)F)cn12]

Intermediate 60: ¹H-NMR (DMSO-d₆) δ: 1.07 (3H, t), 2.99-3.05 (2H, m), 7.74 (1H, d), 7.97 (1H, d), 8.07 (1H, d), 8.42 (1H, d), 9.05 (1H, br s).

Reference Production Example 32

Intermediate 61 represented by the following formula was obtained according to the method described in Reference Production Example 12, using Intermediate 60 in place of Intermediate 14.

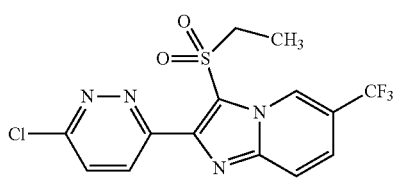 [SMILES: CCS(=O)(=O)c1c(-c2ccc(Cl)nn2)nc2ccc(C(F)(F)F)cn12]

Intermediate 61: ¹H-NMR (DMSO-ds) δ: 1.31-1:38 (3H, m), 3:964.05 (2H, m), 7.97-7.99 (1H, m), 8:15 (2H, d), 8.30 (1H, d), 9.45 (1H, s).

Reference Production Example 33

To a mixture of 0.50 g of Intermediate 63 and 5 mL of methanol was added dropwise 0.3 mL of sodium methoxide (25% methanol solution) under ice-cooling, and the mixture was stirred at room temperature for 16 hours. To the mixture was added water, and the mixture was extracted with ethyl acetate. The obtained organic layer was washed with saturated saline, dried over anhydrous sodium sulfate, and concentrated under reduced pressure. The obtained residue was subjected to silica gel chromatography to obtain 0.38 g of Intermediate 65 represented by the following formula.

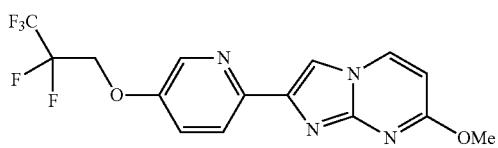 [SMILES: COc1ccn2cc(-c3ccc(OCC(F)(F)C(F)(F)F)cn3)nc2n1]

Intermediate 65: ¹H-NMR (CDCl₃) δ:3.95 (3H, s), 5.00 (2H, t), 6.64 (1H, d), 7.65 (lit, d), 8.01 (1H, d), 8.12 (1H, s), 8.41 (1H, s), 8.75 (1H, d).

Production Example 1

To a mixture of 0.84 g of Intermediate 4 and 6 mL of 1,4-dioxane were added 0.29 g of tris(dibenzylideneacetone) dipalladium (0), 0.36 g of xantphos 0.8 mL of diisopropylethylamine, and 0.2 mL of ethanethiol, and the mixture was refluxed for 90 minutes. To the mixture was added water, and the mixture was extracted with MTBE. The obtained organic layer was dried over sodium sulfate and concentrated under reduced pressure. The obtained residue was subjected to silica gel column chromatography (hexane: ethyl acetate=4:1) to obtain 0⅜g of Compound 1 of the present invention represented by the following formula.

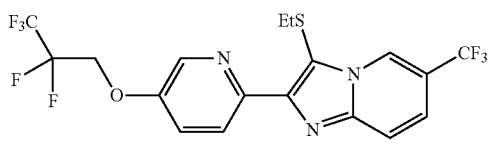

Compound of the present invention: ¹H-NMR (CDCl₃) δ: 8.93 (1H, s), 8.56 (1H, d), 8.40 (1H, d), 7.77 (1H, dd), 7.44 (1H, dd), 7.40 (1H, dd), 4.56 (2H, td), 2.90 (2H, q), 1.16 (3H, t).

Production Example 2

Compounds produced according to die method described m Production Example 1 and physical property values thereof are shown below.

Compounds represented by Formula (A-3) in which a combination, of T, $R^2$, $G^1$, $G^2$, $G^3$, and $G^4$ is any one of the combinations described in Table 24. In Tables 24 and 25, Comp means a compound of the present invention.

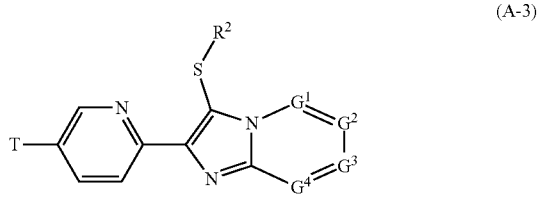

(A-3)

TABLE 24

| Comp | T | $R^2$ | $G^1$ | $G^2$ | $G^3$ | $G^4$ |
|---|---|---|---|---|---|---|
| 2 | OCH₂CF₂CF₃ | CH₂CH₃ | CH | CH | CCF₃ | CH |
| 5 | OCH₂CF₂CF₃ | CH₂CH₃ | CH | CH | CH | CH |
| 24 | OCH₂CF₂CF₃ | CH₂CH₃ | CH | CF | CH | CH |
| 27 | OCH₂CF₂CF₃ | CH₂CH₃ | CH | CH₃ | CH | CH |
| 30 | OCH₂CF₂CF₃ | CH₂CH₃ | CH | 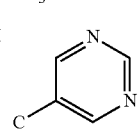 | CH | CH |
| 32 | OCH₂CF₂CF₃ | CH₂CH₃ | CH | CH | CBr | N |
| 34 | OCH₂CF₂CF₃ | CH₂CH₃ | CH | Cc-Pr | CH | CH |
| 39 | OCH₂CF₂CF₃ | CH₂CH₃ | N | CCF₃ | CH | CH |
| 41 | OCH₂CF₂CF₃ | CH₂CH₃ | CH | CCF₃ | CH | N |
| 43 | OCH₂CF₂CF₃ | CH₂CH₃ | CH | CH | CCF₃ | N |
| 68 | OCH₂CF₂CF₃ | CH₂CH₃ | CH | CH | COCH₃ | N |

Compound 2 of the present invention: ¹H-NMR (CDCl₃) δ: 8.68 (1H, d), 8.55 (1H, t), 8.39-8.37 (1H, m) 7.97 (1H, t), 7.40 (1H, dd), 7.11 (1H, dd), 4.56 (2H, td), 2.91 (2H, q), 1.15 (3H, t).

Compound 5 of the present invention: ¹H-NMR (CDCl₃) δ: 8:56 (2H, dq), 8.40 (1H, dd), 7.69 (1H, dt), 7.38 (1H, dd), 7.30 (1H, ddd), 6.94 (1H, td), 4.54 (2H, td), 2.84 (2H, q), 1.14 (3H, t).

Compound 24 of the present invention: ¹H-NMR (CDCl₃) δ: 8:54 (1H, d), 8.50 (1H, ddd), 8.37 (1H, dd) 7.66 (1H, ddd), 7.38 (1H, dd), 7.24-7.19 (1H, m), 4.54 (2H, td), 2.86 (2H, q), 1.15 (3H, t).

Compound 27 of the present invention: LC-MS (measurement condition A): RT=3.72 min (260 nm), MS found: 417:8 [M+H].

Compound 30 of the present invention: LC-MS (measurement condition B): RT=3.41 min (260 nm), MS found: 482.0 [M+H].

Compound 32 of the present invention: LC-MS (measurement condition B): RT=2.17 min (260 nm), MS found: 484.1 [M+2H], Compound 34 of the present invention: LC-MS (measurement condition B): RT=3.97 min (260 nm), MS found: 443.8 [M+H].

Compound 39 of foe present invention: ¹H-NMR (CDCl₃) δ: 1.17 (3H, t), 3.00-3.06 (2H, m), 4.55 (2H, t), 7.38-7.43 (2H, m), 8.16 (1H, d), 8.44 (1H, d), 8.56 (1H, d).

Compound 41 of the present invention: ¹H-NMR (CDCl₃) δ: 1.15 (3H, t), 3.01 (2H, q), 4.51 (2H, t), 7.41-7.43 (1H, m), 8.42 (1H, m), 8.54 (1H, m), 8.77 (1H, s), 9.15 (1H, s).

Compound 43 of the present invention: ¹H-NMR (CDCl₃) δ: 1.16 (3H, t), 3.03-3.05 (2H, m), 4.54 (2H, t), 7.29-7.31 (1H, m), 7.40 (1H, d), 8.44 (1H, d), 8.53 (1H, s), 9.04 (1H, d).

Compound 68 of foe present invention: LC-MS (measurement condition A): RT=3.52 min (260 nm), MS found: 434.7 [M+H].

Compound 17 of the present invention represented by the following formula

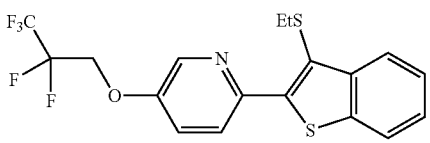

Compound 17 of the present invention: $^1$H-NMR (CDCl$_3$) δ: 8.84 (1H, dd), 8.49 (1H, dd), 8.08-8:05 (1H, m), 7.90-7.81 (4H, m), 4.49 (2H, t), 2.80 (2H, q), 1.13 (3H, t).

Production Example 3

To a mixture of 0.54 g of Compound it of the present invention and 6 mL of chloroform was added 0.6 g of 70% mCPBA under ice-cooling, and the mixture was stirred at room temperature for 6 hours. To the mixture was added a saturated sodium hydrogen carbonate aqueous solution, and then a sodium thiosulfate aqueous solution was added thereto. The mixture was extracted with chloroform. The obtained organic layer was dried over sodium sulfate and concentrated under reduced pressure. The obtained residue was subjected to silica gel column chromatography (hexane: ethyl acetate=2:1) to obtain 0.47 g of Compound 3 Of the present invention represented by the following formula.

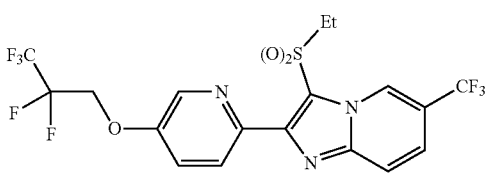

Compound 3 of the present invention: $^1$H-NMR (CDCl$_3$) δ: 9.67 (1H, d), 8.46 (1H, d), 8.12 (1H, d), 7.85 (1H, d), 7.62 (1H, dd), 7.43-7.40 (1H, m), 4.55 (2H, td), 4.00 (2H, q), 1.41 (3H, t).

Production Example 4

Compounds produced according to the method described in Production Example 3 and physical property values thereof are shown below, Compounds represented by Formula (A-4) in which a combination of T, R$^2$, G$^1$, G$^2$, G$^3$, and G$^4$ is any one of the combinations described in Table 25,

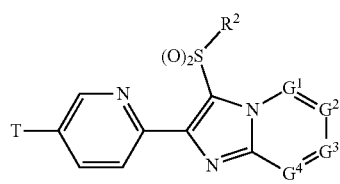

(A-4)

TABLE 25

| Comp | T | R$^2$ | G$^1$ | G$^2$ | G$^3$ | G$^4$ |
|---|---|---|---|---|---|---|
| 4 | OCH$_2$CF$_2$CF$_3$ | CH$_2$CH$_3$ | CH | CH | CCF$_3$ | CH |
| 6 | OCH$_2$CF$_2$CF$_3$ | CH$_2$CH$_3$ | CH | CH | CH | CH |
| 14 | OCH$_2$CF$_2$CF$_3$ | CH$_2$CH$_3$ | CH | CBr | CH | CH |
| 25 | OCH$_2$CF$_2$CF$_3$ | CH$_2$CH$_3$ | CH | CF | CH | CH |
| 28 | OCH$_2$CF$_2$CF$_3$ | CH$_2$CH$_3$ | CH | CCH$_3$ | CH | CH |
| 31 | OCH$_2$CF$_2$CF$_3$ | CH$_2$CH$_3$ | CH | | pyrimidine | CH | CH |
| 33 | OCH$_2$CF$_2$CF$_3$ | CH$_2$CH$_3$ | CH | CH | CBr | CH |
| 35 | OCH$_2$CF$_2$CF$_3$ | CH$_2$CH$_3$ | CH | CH | Cc-Pr | CH |
| 40 | OCH$_2$CF$_2$CF$_3$ | CH$_2$CH$_3$ | N | CCF$_3$ | CH | CH |
| 42 | OCH$_2$CF$_2$CF$_3$ | CH$_2$CH$_3$ | CH | CCF$_3$ | CH | N |
| 44 | OCH$_2$CF$_2$CF$_3$ | CH$_2$CH$_3$ | CH | CH | CCF$_3$ | N |
| 69 | OCH$_2$CF$_2$CF$_3$ | CH$_2$CH$_3$ | CH | CH | COCH$_3$ | N |

Compound 4 of the present invention: $^1$H-NMR (CDCl$_3$) δ: 9.41 (1H, d), 8.46 (1H, d), 8.11 (1H, d), 8.05 (1H, s), 7.52-7.40 (1H, m), 7.20 (1H, dd), 4.55 (2H, t), 4.00 (2H, q), 1.40 (3H, t).

Compound 6 of the present invention: $^1$H-NMR (CDCl$_3$) δ: 9.25 (1H, d), 8.45 (1H, d), 8.07 (1H, d), 7.76 (1H, dd), 7.50-7.45 (1H, m), 7.40 (1H, dd), 7.05 (1H, td), 4.54 (2H, t), 3.92 (2H, q), 1.39 (3H, t).

Compound 14 of the present invention: $^1$H-NMR (CDCl$_3$) δ: 9.42 (1H, dd), 8.44 (1H, d), 8.07 (1H, d), 7.64 (1H, dd), 7.54 (1H, dd), 7:40 (1H, dd), 4.54 (2H, td), 3.95 (2H, q), 1.40 (3H, t).

Compound 25 of the present invention: $^1$H-NMR (CDCl$_3$) δ: 9.26 (1H+dd), 8.44 (1H, d), 8.07 (1H, d), 7.73 (1H, dd), 7.40 (2H, dq), 4.54 (2H, dd), 3.95 (2H, q), 1.39 (3H, t).

Compound 28 of the present invention: $^1$H-NMR (CDCl$_3$) δ: 1.37 (3H, t), 2.40 (3H, s), 3.87 (2H, q), 4.52 (2H, t), 7.30 (1H, d), 7.35-7.38 (1H, m), 7.63 (1H, d), 8.02 (1H, d), 8.42 (1H, d), 9.00 (1H, s).

Compound 31 of the present invention: $^1$H-NMR (CDCl$_3$) δ: 1.41 (3H, t), 3.99 (2H, q), 4.54 (2H, t), 7.40 (1H, d), 7.66 (1H, d), 7.90 (1H, d), 8.12 (1 K d), 8.45 (1H, s), 9.01 (2H, s), 9.30 (1H, s), 9.53 (1H, s).

Compound 33 of the present invention: $^1$H-NMR (CDCl$_3$) δ:1.36 (3H, t), 3.93 (2H, q), 4.53 (2H, t), 7.12 (I K d), 7.38 (1H, d), 7.91 (1H, s), 8:05 (1H, ti), 8.43 (1H, s), 9.12 (1H, d).

Compound 35 of the present invention: $^1$H-NMR (CDCl$_3$) δ: 0.84 (2H, t), 1.12-1.14 (2H, m), 1.34 (3H, t), 1.98-2.03 (1H, m), 3.84-3.90 (2H, m) 4.52 (2H, t), 6.70 (1H, d), 7.36-7.37 (2H, m), 8.03 (1H, d), 8.41 (1H, d), 9.06 (1H, d).

Compound 40 of the present invention: $^1$H-NMR (CDCl$_3$) δ:1.40 (3H, t), 3.70 (2H, q), 4.54 (2H, t), 7.37-7.39 (1H, m), 7.62 (1H, d), 7.96 (1H, d), 8.29 (1H, d), 8.50 (1H, d).

Compound 42 of the present invention: $^1$H-NMR (CDCl$_3$) δ: 1.41 (3H, z), 4.10 (2H, q), 4.55 (2H, t), 7.41-7.43 (1H, m), 8.32 (1H, d), 8.46-8.47 (1H, m), 8.92 (1H, s), 9.95 (1H, s).

Compound 44 of the present invention: $^1$H-NMR (CDCl$_3$) δ: 1.39 (3H, t), 4.10 (2H, q), 4.55 (2H, t), 7.39-7.44 (2H, m), 8.32 (1H, d), 8:46 (1H, d), 9.82 (1H, d).

Compound 69 of the present invention: $^1$H-NMR (CDCl$_3$) δ: 1.31-1.38 (3H, m), 3.98-4.03 (2H, m), 4.11 (3H, s), 4.52 (2H, z), 6.58 (1H, d), 7.33-7.54 (1H, m), 8.22 (1H d), 8.41 (1H, d), 9.28 (1H, d).

Compound 18 of the present invention represented by the following formula

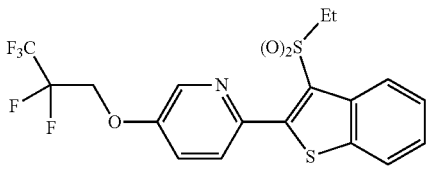

Compound 18 of the present invention: $^1$H-NMR (CDCl$_3$) δ: 8.61 (1H, d), 8.43 (1H, d), 82-5 (1H, d), 7.90-7.67 (4H, m), 4:56 (2H, t), 3.39 (2H, q), 1:28 (3H, t).

Production Example 5

A mixture of 0.26 g of Intermediate 16, 0.05 g of [1,1'-bis(diphenylphosphino)ferrocene]palladium (II) dichloride, 0.38 g of tripotassium phosphate, 9.38 g of 4-fluorophenylboronic acid, 0.3 mL of water, and 3 mL of DME was stirred under a nitrogen atmosphere at 85° C. for 3 hours. To the mixture was added water, and the mixture was extracted with MTBE. The obtained organic layer was dried over sodium sulfate and concentrated under reduced pressure. The obtained residue was subjected to silica gel column chromatography (hexane:ethyl acetate=6:1) to obtain 0.20 g of Compound 7 of the present invention represented, by the following formula.

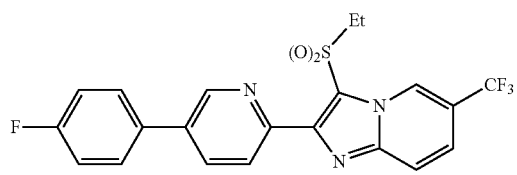

Compound 7 of the present invention: $^1$H-NMR (CDCl$_3$) δ: 9.72 (1H, s), 8.91 (1H, dd), 8:20 (1H, dd), 8.01 (1H, dd), 7.88 (1H, d), 7.65 7.62 (3H, m), 7.11 (2H, tt), 4.09 (2H, q), 1.44 (3H, t).

Production Example 6

The compounds produced according to the method described in Production Example 5 and the physical property values thereof are shown below Compounds represented by Formula (A-5) in which a combination of R$^2$, G$^1$, G$^2$, G$^3$, G$^4$, and G$^5$ is any one of the combinations described in Table 26.

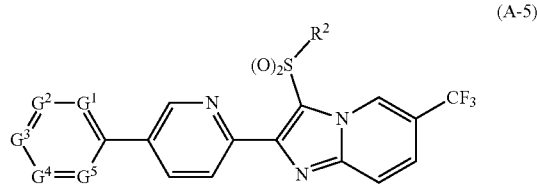

TABLE 26

| Comp | R$^2$ | G$^1$ | G$^2$ | G$^3$ | G$^4$ | G$^5$ |
|---|---|---|---|---|---|---|
| 8 | CH$_2$CH$_3$ | CH | CH | CCF$_3$ | CH | CH |
| 9 | CH$_2$CH$_3$ | CH | CCF$_3$ | CH | CH | CH |
| 10 | CH$_2$CH$_3$ | CH | CCF$_3$ | CH | CCF$_3$ | CH |
| 11 | CH$_2$CH$_3$ | CH | CH | CCF$_3$ | N | CH |
| 12 | CH$_2$CH$_3$ | CH | CCF$_3$ | CH | N | CH |

Compound 8 of the present invention: $^1$H-NMR (CDCl$_3$) δ: 9.71 (1H, s), 8.96 (1H, dd), 8.24 (1H, dd), 8.07 (1H, dd), 7.89 (1 FI, d), 7.74-7.63 (1H, m), 7.27-7.22 (4H, m), 4.10 (2H, q), 1.47 (3H, t).

Compound 9 of the present invention $^1$H-NMR (CDCl$_3$) δ: 9.72 (1H, s), 8.97 (1H, t), 8:25 (1H, d), 8.08 (1H, dd), 7:91-7.81 (3H, m), 7.72 (1H, t), 7:65 (2H, q), 4.10 (2H, q), 1.45 (3H, t).

Compound 10 of the present invention: $^1$H-NMR (CDCl$_3$) δ:9.71 (0.1H, d), 8:99 (1H, dd), 8.29 (1H, dd), 8.12 (1H, s), 8.11 (2H, t), 7.96 (1H, s), 7.90 (1H, d), 7.65 (1H, dd), 4.09 (2H, q), 1.46 (3H, t), Compound 11 of the present invention: $^1$H-NMR (CDCl$_3$) δ: 9.71 (1H, d), 9.04 (1H, d), 8.98 (1H, dd), 8.30 (2H, dd), 8.10 (1H, dd), 7.86 (2H, dd), 7.65 (1H, dd), 4.09 (2H, q), 1.46 (3H, t).

Compound 12 of the present invention: $^1$H-NMR (CDCl$_3$) δ:9.71 (1H, s), 9.12 (1H, d), 8.98 (2H, dt), 8.30 (1H, dd), 8.20-8.19 (1H, m), 8.11 (1H, dd), 7:90 (1H, d), 7.65 (1H, dd), 4.09 (2H, q), 1.46 (3H, t).

Production Example 7

Intermediate 13 was obtained according to the method described in Reference Production Example 3, using Intermediate 12 in place of intermediate 3 mid using 7.2 g of 5-bromo-2-aminopyridine in place of 5-(trifluoromethyl)-2-aminopyridine.

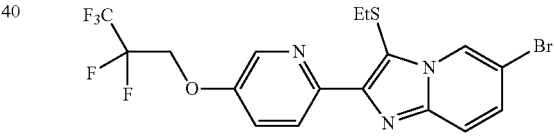

Compound 13 of the present invention: $^1$H-NMR (CDCl$_3$) δ: 8.70 (1H, dd), 8.54 (1H, d), 8.37 (1H, d), 7:57 (1H, dd), 7.37 (2H, td), 4.54 (2H, dd), 2.87 (2H, q), 1.15 (3H, t).

Production Example 8

Compound 15 of the present invention represented by the following formula was obtained according to the method described in Production Example 5, using Compound 14 of the present invention lit place of Intermediate 16.

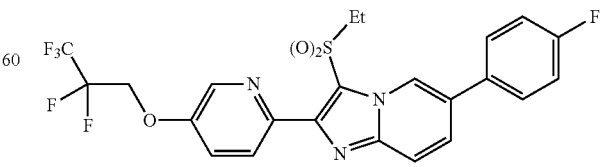

Compound 15 of the present invention: $^1$H-NMR (CDCl$_3$) δ:9.41 (1H, dd), 8.46 (1H, d), 8.10 (1H, d), 7.81 (1H, dd), 1.15 (2H, dd), 7.69 (1H, dd), 7.60-7.57 (2H, m), 7.41 (1H, dd), 4.58-4.52 (2H, m), 3.95 (2H, q), 1.41 (3H, t).

Production Example 9

Compounds produced according to the method described in Production Example 8 and physical property values, thereof are shown below.
Compounds represented by Formula (A-6) in which a combination of $R^2$. $G^1$, $R^{3b}$, $R^{3c}$, and $G^4$ is a combination described in Table 27.
Formula (A-6):

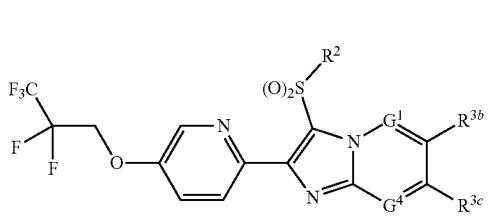

(A-6)

TABLE 27

| Comp | $R^2$ | $G^1$ | $R^{3b}$ | $R^{3c}$ | $G^4$ |
|------|-------|-------|----------|----------|-------|
| 16 | CH₂CH₃ | CH | cyclopropyl | H | CH |
| 37 | CH₂CH₃ | CH | H | 4-F-phenyl | CH |
| 38 | CH₂CH₃ | CH | H | pyrimidinyl | CH |

Compound 16 of the present invention: ¹H-NMR (CDCl₃) δ: 9.03 (1H, d), 8:43 (1H, d), 8.04 (1H, d), 7.65 (1H, d), 7.38 (1H, dd), 7:17 (1H, dd), 4.54 (2H, t), 3.87 (2H, q), 2.03-1.96 (1H, m), 1.38 (3H, t), 1.08-1.03 (2H, m), 0.76 (2H, dd).
Compound 37 of the present invention: ¹H-NMR (CDC₃) δ:1.39 (3H, t), 3.93-3.95 (2H, m), 4.53 (2H, t), 7.19-7.24 (3H, m), 7.38-7.40 (1H, m), 7.65 (2H, s), 7.86 (1H, s), 8.08-8.10 (1H, m), 8.44 (1H, s), 9.25 (1H, d).
Compound 38 of the present invention: ¹H-NMR (CDCl₃) δ: 1.40 (3H, t), 3.95-4.01 (2B, m), 4.54 (2H, t), 7.2-5 (1H, s), 7.40-7.41+(1H, m), 7.97 (1H, i>), 8.10 (1H, d), 8.46 (1H, s), 9.07. (2H, s), 9.31 (1H, s), 9.40 (1H, d).

Production Example 10

A mixture of 200 mg of Intermediate 23,480 mg of cesium carbonate, 210 mg of 2,2,3,3-tetrafluoropropanol, and 4 mL of N-methylpyrrolidone (hereinafter referred to as NMP) was stirred at 70° C. for 2 hours. After codling the obtained mixture to room temperature, water was added thereto and the mixture was extracted with ethyl acetate. The obtained organic layer was washed with saturated saline, dried over anhydrous sodium sulfate, and concentrated under reduced pressure. The obtained residue was subjected to silica gel chromatography (hexane:ethyl acetate=2:1) to obtain 200 mg of Compound 19 of the present invention as shown below.

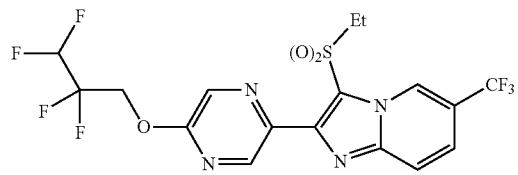

Compound 19 of the present invention: ¹H-NMR (CDCl₃) δ:9.62 (1H, s), 8.87 (1H, d), 8.40 (1H, d), 7.88 (1H, d), 7.65 (1H, dd), 6.02 (1H, tf) 4.85 (2H, t) 3.89 (2H, q), 1.42 (3H, t).

Production Example 11

Compounds produced according to the method described in Production Example 10 and physical property values thereof are shown below.
Compounds represented by Formula (A-7) in which a combination of T, $R^2$, $G^1$, $G^2$, $G^3$, and $G^4$ is a combination described in Table 28.

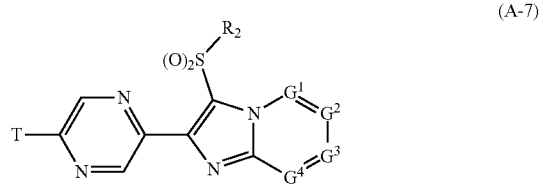

(A-7)

TABLE 28

| Comp | T | $R^2$ | $G^1$ | $G^2$ | $G^3$ | $G^4$ |
|------|---|-------|-------|-------|-------|-------|
| 20 | OCH₂CF₂CF₃ | CH₂CH₃ | CH | CCF₃ | CH | CH |

Compound 20 of the present invention: ¹H-NMR (CDCl₃) δ: 9.63 (Hi, s), 8.87 (1H, d), 8.43 (1H, d), 7.89 (1H, d)#7.65 (1H, dd), 4:93 (2H, t), 3:90 (2H, d), 1.42 (3H, t).

Production Example 12

To a mixture of 0.50 g of Intermediate 38# cesium carbonate 0.42 g, and 5 mL of DMF was added dropwise 0.34 g of 2,2,3,3-tetrafluoropropyl trifluoromethanesulfonate under ice-cooling, and the mixture was stirred at room temperature for 3 hours. To the mixture was added water, and the mixture was extracted with MTBE. The obtained organic layer was washed with saturated saline, dried over anhydrous sodium sulfate, and concentrated under reduced pressure. The obtained residue was subjected to silica gel chromatography (hexane:ethyl acetate=4:1) to obtain 0.39 g of Compound 21 of the present invention represented by tire following formula.

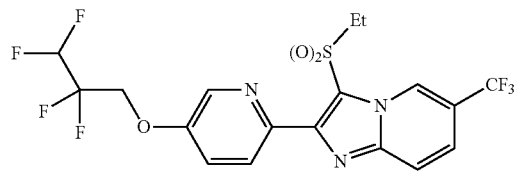

Compound 21 of the present invention: $^1$H-NMR (CDCl$_3$) δ: 9.67 (1H, d), 8.45 (1H, dd), 8.11 (1H, dd), 7.85 (1H, d), 7.61 (1H, dd), 7.40 (1H, dd), 4.47 (2H, q), 4.00 (2H, q), 1.41 (4H, q).

Production Example 13

Compounds produced according to the method described in Production Example 12 and physical property values thereof are shown below. Compounds represented by Formula (A-4) in which a combination of T, R$^2$, G$^1$, G$^2$, G$^3$, and G$^4$ is any one of the combinations described in Table 29.

TABLE 29

| Comp | T | R$^2$ | G$^1$ | G$^2$ | G$^3$ | G$^4$ |
|---|---|---|---|---|---|---|
| 22 | OCH$_2$CF$_2$CF$_2$CF$_3$ | CH$_2$CH$_3$ | CH | CH | CCF$_3$ | CH |
| 23 | OCH$_2$CF$_2$CFHCF$_3$ | CH$_2$CH$_3$ | CH | CH | CCF$_3$ | CH |
| 26 | OCH$_2$CF$_2$CF$_2$H | CH$_2$CH$_3$ | CH | CF | CH | CH |

Compound 22 of the present invention: $^1$H-NMR (CDCl$_3$): δ: 9.67 (1H, s), 8.47 (1H, d), 8.13 (1H, d), 7.85 (1H, d), 7:62 (1H, dd), 7.42 (1H, dd), 4.59 (2H, t), 4.00 (2H, q), 1.41 (3H, t).

Compound 23 of the present invention: $^1$H-NMR (CDCl$_3$) δ: 9.67 (1H, s), 8.45 (1H, d), 8.12 (1H, d), 7.85 (1H, d), 1.62 (1H, dd), 7.41 (1H, dd), 5.29-5.10 (1H, m), 4.58-4.39 (2H, m), 4.04-3.97 (2H, m), 1.42 (3H, t).

Compound 26 of the present invention: $^1$H-NMR (CDCl$_3$) δ: 926 (1H dd), 8.43 (1H, d), 8.06 (1H, d), 7.74-7.70 (1H, m), 739 (2H, ddd), 6.08 (1H, tt), 4.48 (2H, td), 3.95 (2H, q), 1.39 (3H, t).

Production Example 14

Compounds produced according to the method described in Production Example 23 and physical property values thereof are shown below.
Compounds represented by Formula (A-4) in which a combination of T, R$^2$, G$^1$, G$^2$, G$^3$, and G$^4$ is any one of the combinations described in Table 30,

TABLE 30

| Comp | T | R$^2$ | G$^1$ | G$^2$ | G$^3$ | G$^4$ |
|---|---|---|---|---|---|---|
| 29 | OCH$_2$CF$_2$CF$_3$ | CH$_2$CH$_3$ | CH | 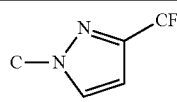 | CH | CH |
| 36 | OCH$_2$CF$_2$CF$_3$ | CH$_2$CH$_3$ | CH | CH | 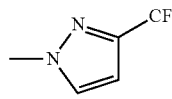 | CH |

Compound 29 of the present invention: $^1$H-NMR (CDCl$_3$) δ: 1.40 (3H, t), 3.98-4.00 (2H, m), 4.54 (2H, t), 6.80 (1H, d), 7.42 (1H, d), 7.86 (1H, m), 7.95-7.99 (2H m), 8.12 (1H, d), 8.45 (1H, s), 9.66 (1H, s).

Compound 36 of the present invention: (CDCl$_3$) δ: 1.3943H, t), 3.97 (2H, q), 4.54 (2E t)>6.82 (1H, d), 7.40 (1H, dd), 7.62 (1H, dd), 7.93-7.94 (1H, m) 8.08-8.11 (2H, m), 8.45 (1H, d), 9.36 (1H, d).

Production Example 15 compounds produced according to the method described in Production Example 2 and physical property values thereof are shown below.
Compounds represented by Formula (A-11) in which a combination of T, G$^1$, G$^2$, G$^3$, and G$^4$ is any one of the combinations described in Table 31.

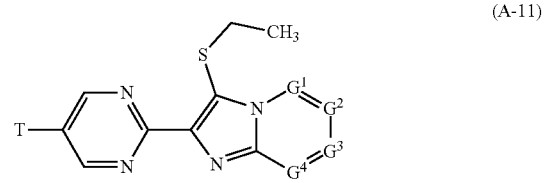

(A-11)

TABLE 31

| Comp | T | G$^1$ | G$^2$ | G$^3$ | G$^4$ |
|---|---|---|---|---|---|
| 45 | ![m-CF3-phenyl] | CH | CH | CH | CH |
| 47 | ![CF3-pyridyl] | CH | CH | CH | CH |
| 49 | ![CF3-pyrazolyl] | CH | CH | CH | CH |
| 51 | OCH$_2$CF$_2$CF$_3$ | CH | CCF$_3$ | CH | CH |

TABLE 31-continued

| Comp | T | G$^1$ | G$^2$ | G$^3$ | G$^4$ |
|---|---|---|---|---|---|
| 53 | ![CF3-pyrazolyl] | CH | CCF$_3$ | CH | CH |

TABLE 31-continued

| Comp | T | G¹ | G² | G³ | G⁴ |
|------|---|----|----|----|----|
| 55 | 3-CF₃, methyl-phenyl | CH | CCF₃ | CH | CH |
| 57 | 3-CF₃, 5-methyl-pyridine | CH | CCF₃ | CH | CH |
| 59 | OCH₂CF₂CF₃ | N | CCF₃ | CH | CH |

Compound 45 of the present invention: ¹H-NMR (CDCl₃) δ: 1.18-1.24 (3H, m), 4.0$ (2H, q), 735-7:43 (1H, m % 7.43-7.49 (2H, m) 7.52-7.56 (2H, m % 1:63-7.67 (2H, m), 7.81-7.85 (1H, m), 9.00 (1H, s), 9.16 (1H, s).

Compound 47 of the present invention: ¹H-NMR (DMSO-d₆) δ: 1.09 (3H, t), 3.04-3.09 (2H, m), 7.71: (1H, d), 7.94-7.99 (3H, m), 8.76 (2H, d), 9.04 (1H, s), 9.47 (2H, s).

Compound 49 of the present invention: ¹H-NMR (CDCl₃) δ: 1.18 (3H, t), 3.00 (2H, q), 6.83-6.84 (1H m % 6.97-6.99 (1>1, m), 7.33 (lilt), 7.75 (1H, d), 8.08 (1H, s), 8.63 (Hid), 9.31 (2H, s).

Compound 51 of the present invention: ¹H-NMR (CDCl₃) δ: 1:17 (3H, t), 3.01 (2H, q), 4.60 (2H, t) 7.43 (1H, d), 7.81 (1H, d), 8.67 (2H, s), 8.97 (1H, s).

Compound 53 of the present invention: ¹H-NMR (CDCl₃) δ: 119-1.24 (3H, m), 3.05 (2H, t), 6.85 (1H, s), 7.46 (1H, d), 7.85 (1H, d), 8.09 (1H, s), 9.00 (1H, s), 9.33 (2H, s).

Compound 55 of the present invention: ¹H-NMR (CDCl₃) δ: 1.21 (3H, t), 3.10 (2H, t), 7.45 (1H, d), 7.68-7.74 (1H, m), 7.82-7.89 (3H, m), 8.54 (1H, d), 9.01-9.05 (1H, m), 9.17 (2H, s).

Compound 57 of the present invention: ¹H-NMR (CDCl₃) δ: 1.15-1.28 (3H, m), 3.06-3.11 (2H, m), 133.7:50 (1H, m), 7.84 (1H, t), 8.15-8.18 (1H, m), 8.54-8.59 (1H, m), 8.99-9.01 (1H, m), 9.08-9.11 (2H, s), 9.19 (1H, s).

Compound 59 of the present invention: ¹H-NMR (CDCl₃) δ: 118 (3H, t), 3:13 (2H, q), 4.61 (2H, t), 7.42 (1H, d), 8.20 (1H, d), 8.69 (2H, s).

Production Example 16

Compounds produced according to the method described in Production Example 3 and physical property values thereof are shown below.

Compounds represented by Formula (A-12) in which a combination of T, G¹, G², G³, and G⁴ is any one of the combinations described in Table 32.

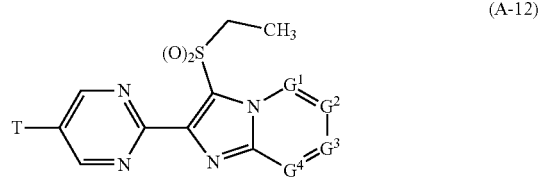

(A-12)

TABLE 32

| Comp | T | G¹ | G² | G³ | G⁴ |
|------|---|----|----|----|----|
| 46 | 3-CF₃, methyl-phenyl | CH | CH | CH | CH |
| 48 | 3-CF₃, 5-methyl-pyridine | CH | CH | CH | CH |
| 50 | N-methyl-3-CF₃-pyrazole | CH | CH | CH | CH |
| 52 | OCH₂CF₂CF₃ | CH | CCF₃ | CH | CH |
| 54 | N-methyl-3-CF₃-pyrazole | CH | CCF₃ | CH | CH |
| 56 | 3-CF₃, methyl-phenyl | CH | CCF₃ | CH | CH |
| 58 | 3-CF₃, 5-methyl-pyridine | CH | CCF₃ | CH | CH |
| 60 | OCH₂CF₂CF₃ | N | CCF₃ | CH | CH |

Compound 46 of the present invention: ¹H-NMR (CDCl₃) δ: 1.47 (3H, t), 4.07 (2H, q), 7.49-7.56 (3H, m), 7.62-7.67 (3H, m), 7.96 (1H, d), 9.13 (2H, s), 9.69 (1H, s).

Compound 48 of the present invention: ¹H-NMR (DMSO-d₆) δ: 1.36 (3H, t), 4.05 (2H, q), 7.95-8.00 (31i m), 8.12 (1H, d), 8.77 (2H, d), 9.41 (1H, s), 9.49 (2H, s).

Compound 50 of the present invention: ¹H-NMR (CDCl₃) δ: 144 (3H, t), 3:95 (2H, t)₅ 6.85 (1H, s), 7.09-7.11 (1H, m), 7.49-7.53 (1H, d)₅ 7-86 (1H, d), 8.10 (1H, s), 9.23-9.31 (3H, m).

Compound 52 of the present invention: ¹H-NMR (CDCl₃) δ:1.43 (3H, t), 3.96 (2H, q), 4.61 (2H, t), 7:62 (1H, d), 7.93 (1H, d), 8.65 (2H, s), 9.63 (1H, s).

Compound 54 of the present invention: ¹H-NMR (CDCl₃) δ:1.46 (3H, t)₃ 4.00 (2H, q), 6.87 (1H, d), 7.65 (1H, dd), 7.96 (1H, d), 8.12 (1H d), 9.33 (2H, s), 9.65 (1H, s).

Compound 56 of the present invention: ¹H-NMR (CDCl₃) δ: 1.46 (3H, t), 4.65 (2H, q), 7.63-7.71 (2H, m), 7.76-7.77 (1H, m), 7.85 (1H, d), 7.90 (1H, s), 7.97 (1H, d), 9.15 (2H, s), 9.68 (1H, s).

Compound 58 of the present invention: ¹H-NMR (CDCl₃) δ:1.47 (3H, t), 4.04 (2H, q), 7.65 (1H, d), 7.98 (1H, d), 7.19 (1H, s), 9.03 (1H, s), 9.12 (1H, s), 9.18 (2H, s), 9.67 (Ills).

Compound 60 of the present invention: ¹H-NMR (CDCl₃) δ: 1.47 (3H, t), 3.73 (2H, q), 4.61 (2H, t), 7.63 (1H, d), 8.32 (1H, d), 8.64 (2H, s).

Production Example 17

Compounds produced according to the method described in Production Example 10 and physical property values thereof are shown below.

Compounds represented by Formula (A-13) in which a combination of T, $R^2$, $G^1$, $G^2$, $G^3$, and $G^4$ is a combination described in Table 33.

(A-13)

TABLE 33

| Comp | T | $R^2$ | $G^1$ | $G^2$ | $G^3$ | $G^4$ |
|---|---|---|---|---|---|---|
| 61 | $OCH_2CF_2CF_3$ | $CH_2CH_3$ | CH | $CCF_3$ | CH | CH |
| 62 | $OCH_2CF_2CF_2H$ | $CH_2CH_3$ | CH | $CCF_3$ | CH | CH |
| 63 | $OCH_2CF_2CFHCF_3$ | $CH_2CH_3$ | CH | $CCF_3$ | CH | CH |
| 64 | $OCH_2CF_2CF_2CF_3$ | $CH_2CH_3$ | CH | $CCF_3$ | CH | CH |

Compound 61 of the present invention: H-NMR (CDCl$_3$) δ: 1.32 (3H, t), 3.99 (2H, q), 5.40 (2H, t), 7-63 (1H, d), 7.96 (1H, d), 8.13 (1H, d), 8.25 (1H, d), 9.44 (1H, s).

Compound 62 of the present invention: $^1$H-NMR (DMSO-d$_6$) δ: 1.32 (3H, t), 4.00 (2H, q), 5.17 (2H, t), 6.60-6.89 (1H, m), 7.58 (1H, d), 7.96 (1H, dd), 8.13 (1H, d), 8.23 (1H, d), 944 (1H, s).

Compound 63 of the present invention: $^1$H-NMR (DMSO-d$_6$) δ: 1.33 (3H, t), 4.00 (2H, q), 5.14-5.1.8 (2H, m), 6.23-6.24 (1H, m), 7.58 (1H, d), 7.94 (1H, d), 8.13 (114, d), 8.25 (1H, d), 9.45 (1H, s).

Compound 64 of the present invention: $^1$H-NMR (DMSO-d$_6$): δ: 1.32 (3H, t), 4.00 (2H, q), 5.43 (2H, t), 7.63 (1H, d), 7.96 (1H, d), 8.14 (1H, d), 8.25 (1H, d), 9.44 (1H, s).

Production Example 18

Compounds produced according to the method described in Reference Production Example 15 and physical property values thereof are shown below.

Compound 70 of the present invention represented by the following formula was obtained according to the method described in Reference Production Example 15, using Compound 69 Of the present invention in place of Intermediate 20.

Compound 70 of the present invention: LC-MS (measurement condition B): RT=2.78 min (260 nm), MS found: 453.2 [M+H],

Production Example 19

Compounds produced according to the method described in Production Example 5 and physical property values thereof are shown below. Compounds represented by Formula (A-13) in which a combination of T, R, $G^1$, $G^2$. $G^3$ and $G^4$ is any one of the combinations described in Table 34.

TABLE 34

| Comp | T | $R^2$ | $G^1$ | $G^2$ | $G^3$ | $G^4$ |
|---|---|---|---|---|---|---|
| 65 | (3-CF$_3$-phenyl) | $CH_2CH_3$ | CH | $CCF_3$ | CH | CH |
| 66 | (4-CF$_3$-pyridyl) | $CH_2CH_3$ | CH | $CCF_3$ | CH | CH |
| 67 | (CF$_3$-pyrazolyl) | $CH_2CH_3$ | CH | $CCF_3$ | CH | CH |

Compound 65 of the present invention: $^1$H-NMR (DMSO-d$_6$) δ:1.37 (3H, t), 4.11 (2H, q), 7:86 (1H, t), 7.96-8.00 (2H, m), 8:12 (1H, d), 8.58-8.64 (3H, m), 9.48 (1H, s).

Compound 66 of the present invention: $^1$H-NMR (DMSO-d$_6$) δ: 1.37 (3H, t), 4.09-4.11 (2H, m), 7.89 (1H, d), 8.17 (1H, d), 8.42 (1H, d), 8.73 (1H, d), 9.00 (1H, s), 9.19 (1H, s), 9.47 (1H, s), 9.73 (1H, s).

Compound 67 of the present invention: $^1$H-NMR (CDCl$_3$) δ: 1.47 (3H, t), 4.04 (2H, q)$_4$ 6.82 (1H+d), 7.67 (18, dd), 7.90 (1H, d), 8.40. (2H, qz), 8.90 (1H, d), 9.67 (1H, s).

Next, formulation examples of the compounds of the present invention are shown. Parts represent parts by weight.

Formulation Example 1

10 parts of any one of Compounds 1 to 70 of the present invention are mixed with a mixture of 35 parts of xylene and 35 parts of DMR, and 14 parts of polyoxyethylene styrylphenyl ether and 6 parts of calcium dodecylbenzenesulfohate are added thereto. The resultant is mixed to obtain each formulation.

Formulation Example 2

4 parts of sodium laurylsulfate, 2 parts of calcium ligninsulfonate, 20 parts of synthetic hydrated silicon oxide fine powder, and 54 parts of diatomaeecus earth are mixed, and 20 parts of any one of Compounds 1 to 70 of the present invention is, further added thereto. The resultant is mixed to obtain each formulation.

Formulation Example 3

To 2 parts of any one of Compounds 1 to 70 of the present invention are added 1 part of synthetic hydrated silicon oxide fine powder, 2 parts of calcium ligninsulfonate, 30 parts of bentonite, and 65 parts of kaolin clay, and the resultant is mixed. Then, to the mixture is added an appropriate amount of water. The mixture is further stirred, granulated by a granulator, and air-dried to obtain each formulation.

Formulation Example 4

1 part of any one of Compounds 1 to 70 of the present invention is mixed with an appropriate amount of acetone, and 5 parts of synthetic hydrated silicon oxide fine powder, 0.3 parts of isopropyl acid phosphate, and 93.7 parts of kaolin, clay are added thereto. The resultant is sufficiently stirred and mixed, and acetone is removed by evaporation to obtain each formulation.

Formulation Example 5

35 parts of a mixture of polyoxyethylene alkyl ether sulfate ammonium salt and white carbon (weight ratio 1i 1), 20 parts of any one of Compounds 1 to 70 of the present invention, and 45 parts of water are thoroughly mixed to obtain a formulation.

Formulation Example 6

0.1 parts of any one of Compounds ho 70 of the present invention is mixed with a mixture of 5 parts of xylene and 5 parts of trichloroethane. The mixture is mixed with 89.9 parts of kerosene to obtain each formulation.

Formulation Example 7

10 mg of any one of Compounds 1 to 70 of the present invention is mixed with 0.5 nil of acetone. This solution is added dropwise to 5 g of solid feed powder for animals (Breeding Solid Feed Powder CE-2, manufactured by Japan Clea Co, Ltd.) and the resultant is mixed uniformly. Then, the acetone is dried by evaporation to obtain each poison bait.

Formulation Example 8

0.1 parts of any one of Compounds 1 to 70 of the present invention and 49.9 parts of NEO-CHIOZOL (manufactured by Chuo Kasei Co., Ltd.) are put in an aerosol can, and an aerosol valve is mounted thereon. Then the can is filled with 25 parts of dimethyl ether and 25 parts of LPG and shaken, and an actuator is mounted thereon to obtain an oily aerosol.

Formulation Example 9

Ah aerosol container is filled with a mixture of 0.6 parts of any one of Compounds 1 to 70 of the present invention, 0.01 parts of 2,6-di-tert-butyl-4-methylphenol, 5 parts of xylene, 339 parts of kerosene, and 1 part of an emulsifier {RHEODOL MO-60 (manufactured by Kao Corporation)}, and 50 parts of distilled water, and a valve is mounted thereon. Then, the container is filled with 40 parts of a propellant (LPQ) under pressure through the valve to obtain an aqueous aerosol.

Formulation Example 10

0.1 g 6f any one of compounds 1 to 70 Of the present invention is mixed with 2 ml of propylene glycol, and the mixture is impregnated into a ceramic plate of 4.0 cm×4.6 cm having a thickness of 1.2 cm, to obtain a heating type smoking agent.

Formulation Example 14

5 parts of any one of Compounds 1 to 70 Of the present invention and 95 parts of dm ethylene-methyl methacrylate copolymer (a proportion of methyl methacrylate relative to the total weight of the copolymer: 10% by weight, Acryft WD301, manufactured by Sumitomo Chemical Co., Ltd.) are melt-kneaded with a closed pressurizing kneader (manufactured by Moriyama Works), and the obtained kneaded matter is extruded from an extrusion molding machine through a molding die to obtain a rod-shaped molded body having a length of 15 cm and a diameter of 3 mm.

Formulation Example 12

5 parts of any one of Compounds 1 to 70 of the present invention and 95 parts, of a soft vinyl chloride resin are melt-kneaded with a closed pressurizing kneader (manufactured by Moriyama Works), and the obtained kneaded matter is extended from an extrusion molding machine through a molding die to obtain rod-shaped molded body having a length of 15 cm and a diameter of 3 mm.

Formulation Example 13

100 mg of anyone of Compounds 1 to 70 of the present invention, 68.75 mg of lactose, 237.5 mg of corn starch, 43.75 mg of microcrystalline cellulose, 18.75 mg of polyvinylpyrrolidone, 28.75 mg of sodium carboxy methyl starch, and 2.5 mg of magnesium stearate are mixed, and the obtained mixture, is compressed to an appropriate size to obtain a tablet.

Formulation Example 14

25 mg of any one of Compounds 1 to 70 of the present invention 60-mg of lactose, 25 mg of corn starch, 6 mg of carmellose calcium an appropriate amount of 5% hydroxypropyl methylcellulose are mixed, and a hard shell gelatin capsule or a hydroxypropylmethyl cellulose capsule is filled with the obtained mixture to obtain an encapsulated formulation.

Formulation Example 15

To 100 mg of any one of Compounds 1 to 70 of the present invention, 500 mg of fumaric acid, 2,000 mg of sodium chloride, 150 mg of methylparaben, 50 mg of propylparaben, 25,000 mg of granulated sugar, 13,000 mg of sorbitol (70% solution), 100 mg of Veegum K (Vanderbilt Co.), 35 mg of a perfume, and 500 mg of a colorant is added distilled water so as to make a final volume of 100 ml, and the resultant is mixed to obtain a suspension for oral administration, Formulation Example 16

5% by weight of any one of Compounds 1 to 70 of the present invention is mixed with 5% by weight of an emulsifier, 3% by weight of benzyl alcohol, and 30%, by weight of propylene glycol, and a phosphate buffer is, added thereto so that a pH of the solution is 6.0 to 6.5. Then, water as a remaining portion is added thereto to obtain a liquid formulation for oral administration.

Formulation Example 17

5% by weight of aluminum distearate is added in 57% by weight of fractionated palm oil and 3% by weight of polysorbate 85, and dispersed therein by heating. 25% by weight of saccharin is dispersed in an oily vehicle obtained by cooling this dispersion to room temperature. To the resultant is dispensed 10% by weight of any one of Compounds 1 to 70, to obtain a pasty formulation for oral administration.

Formulation Example 18

5% by weight of any one of Compounds 1 to 70 Of the present invention is mixed with 95% by weight of limestone powder, and a wet granulation method is used to obtain a granule for oral administration.

Formulation Example 19

5 parts of any one of Compounds 1 to 70 of the present invention are mixed with 80 parts of diethylene glycol monoethyl ether, and the mixture is mixed with 15 parts of propylene carbonate to obtain a spot-on solution.

Formulation Example 20

10 parts of any one of Compounds 1 to 70 of the present invention are mixed with 70 parts of diethylene glycol monoethyl ether, and the mixture is mixed with 20 parts of 2-octyl dodecanol to obtain a pour-On solution.

Formulation Example 21

To 0.5 parts of any one of Compounds 1 to 70 of the present invention are added 60 parts of NIKKOL™ TEALS-42 (Nikko Chemicals Co., Ltd., 42% aqueous solution of triethanolamine lauryl sulfate) and 20 parts of propylene glycol, and the mixture is sufficiently stirred and mixed until the mixture becomes a uniform solution. Then, 19.5 parts of water are added t hereto, and tire resultant is further sufficiently stirred and mixed to obtain a shampoo formulation as a uniform solution.

Formulation Example 22

0.15% by weight of any one of Compounds 1 to 70 of the present invention, 95% by weight of an animal feed, and 4-85% by weight of a mixture of dibasic calcium phosphate, diatomaceous earth, Aerosil, and carbonate (or chalk) are thoroughly stirred and mixed to obtain a feed premix for animals.

Formulation Example 23

7.2 g of any one of Compounds 1 to 70 of the present invention is mixed with 92.8 g of VOSCO™ S-55 (manufactured by Maruishi Pharmaceutical Co., Ltd.) at 100° C. poured into a suppository mold, and cooled and solidified to obtain a suppository.

Next, the efficacy of the compound of the present invention against harmful arthropods is shown by test examples. In the following test examples, the test is earned put in a state in which escape of insects is prevented and at a temperature of 25°Q.

Test Example 1

A test compound is made into a formulation according to the method described in Formulation Example 5, and water containing 0:03% by volume of a spreading agent is added thereto to prepare a diluted solution containing a predetermined concentration of the test compound.

Approximately 30 *Aphis gossypii* (all stages) are inoculated into cucumber (*Cucumis sativiis*) seedlings (at a second main leaf development stage) which has been planted in a container. One day later, the diluted solution is sprayed on the seedlings at a rate of 10 mL/seedling. After 5 additional days, the number of surviving insects is investigated and a controlling value is calculated according to the following expression, Controlling value (%)={1−($Cb \times Tai$)/($Cai \times Tb$)}×100

Symbols in the expression represent the following, meanings.
Cb: Number of test insects in a non-treated section
Cai: Number of surviving insects at the time of investigating anon-treated section
Tb: Number of test insects in a treated section
Tai: Number of surviving insects at the time of investigating a treated section
Here, tire non-treated section means a section where the same operation as the treated section is performed except that the test compound is not used.

As a result of carrying out the test according to Test Example f using the following compounds of tire present invention as test compounds at a predetermined concentration of 500 ppm, the following compounds of the present invention all showed a controlling value of 90% or more.

Compounds of the present invention: 3, 4, 6, 10, 14, 15, 16, 18, 19, 20, 21 to 29, 31, 33, 35, 37, 40, 44, 50, 52, 60, 66, and 67

Test Example 2

A test compound is made into a formulation according to the method described, in Formulation Example 5, and water containing 0.03% by volume of a spreading agent is added thereto to prepare a diluted solution containing a predetermined concentration of the test compound.

The diluted solution is sprayed at a rate of 10 mL/seedling to a rice (*Oryza sativa*) seedling (at a second leaf development stage) which has been planted in a container. Later, twenty 3-instar larvae of brown rice planthopper are released thereinto. After 6 days, the number of surviving insects is investigated and a mortality rate of insects is determined by the following expression.

Mortality rate of insects (%)={1−number of surviving insects/20}×100

As a result of carrying out the test according to Test Example 2 using the following compounds of the present invention as test compounds at predetermined concentration of 500 ppm, the following compounds of the present invention all showed a mortality rate of insects of 90% or more.

Compounds of the present invention: 10, 16, 19, and 21

Test Example 3

A test compound is made into a formulation according to the method described in Formulation Example 5, and water is added thereto to prepare a diluted solution containing a predetermined concentration of the test compound.

7.7 g of artificial feed (Insecta LF, manufactured by Nosan Corporation) is placed in a container, and 2 mL of the diluted solution is irrigated thereto. Five 4-instar larvae of tobacco cutworm are released onto the artificial feed. After 5 days, the number of surviving insects is counted, and a mortality rate of insects is calculated by the following expression, Mortality rate of insects (%)=(1−number of surviving insects/5)×100

As a result of carrying out the test according to Test Example 3 using the following compounds of the present invention as test compounds at a predetermined concentration of 500 ppm, the following compounds of the present invention all showed a mortality rate of insects of 80% or more, Compounds of the present invention: 3, 4, 6, 7, 11, 14, 15, 16, 19, 20, 21 to 23, 25, 26, 28, 29, 31, 33, 35 to 37, 40, 44, 50, 52, 54, 58, and 60 to 64

Test Example 4

A test compound is made into a formulation according to the method described in Formulation Example 5, and water containing 0.03% by volume of a spreading agent is added thereto to prepare a diluted solution containing a predetermined concentration of the test compound.

The diluted solution is sprayed at a rate of 20 mL/seedling to a cabbage (*Brassicae oleracea*) seedling (at a second to third main leaf development stage) which has been planted in a container. Then, stem and leaf of this seedling are cut off and put in a container with after paper spread. Five Z-instar larvae of diamondback moths are released thereinto. After 5 days, the number of surviving insects is counted and a mortality rate of insects is calculated by the following expression.

Mortality rate of insects %=(1−number of surviving insects/5)×100

As a result of carrying out the test according to Test Example 4 using the following compounds of the present invention as test compounds at a predetermined concentration of 500 ppm, the following compounds of the present, invent ion all showed a mortality rate of insects of 80% or more.

Compounds of the present invention: 3, 4, 6, 7, 8, 10, 11, 12, 14, 15, 16, 18, 19, 20 to 26, 28, 29, 31, 33, 35, 37, 40, 42 to 44, 50, 52, 56, 58, and 60 to 64

Test Example 5

1 mg of each test compound is dissolved in 50 µL of a mixed solution of polyoxyethylene sorbitan monococoate: acetone=5.95 (volume ratio). To the resultant is added water containing 0.03% by volume of a spreading agent, to prepare a diluted solution containing a predetermined concentration of the test compound.

Seeds of corn (*Zea mays*) are seeded onto a tray lined with wet Kimwipes, After the corn has grown for 5 days, die entire seedlings are immersed into the diluted solution for 30 seconds. Thereafter, two seedlings are put in a petri dish (diameter of 90 mm), and ten 2-instar larvae of western corn rootworm are released thereinto. Five days later, the number of dead insects is counted, and a mortality rate of insects is calculated by the following expression.

Mortality rate of insects (%)=(number of dead insects/10)×100.

As a result of carrying out the test according to Test Example 5 using the following compounds of the present invention as test compounds at a predetermined concentration of 500 ppm, the following compounds of the present invention all showed a mortality rate of insects of 80% or more.

Compounds of the present invention: 1, 2, 3, 4, 5, 6, 15, 16, 19, 20 to 26, 28, 33, 38, 44, 52, and 60 to 64

Test Example 6

A test compound is made into a formulation according to the method described in Formulation Example 5, and water is added thereto to prepare a diluted solution containing a predetermined concentration of the test compound.

A container is lined with a filter paper having a diameter of 5.5 cm. 30 mg of sucrose is put on the filter paper and then 0.7 mL of the diluted solution is added thereon. Ten female-adult housefly are released into the container. After 24 hours, the number of dead insects is counted, and a mortality rate of insects is calculated by the following expression.

Mortality rate of insects (%)=(number of dead insects/number of test insects)×100

As a result of carrying out the test according to Test Example 6 using the following compounds of the present invention as test compounds at a predetermined concentration of 500 ppm, the following compounds of the present invention all showed a mortality rate of insects of 100,%.

Compounds of the present invention: 3, 4, 21, 22, 24, 33, 35, 40, 52, 61, and 62

INDUSTRIAL APPLICABILITY

The compound of the present invention exhibits excellent controlling effects against harmful arthropods.

The invention claimed is:
1. A compound represented by Formula (I):

in the formula,

Q represents a group represented by Formula Q1, a group represented by Formula Q2, or a group represented by Formula Q3,

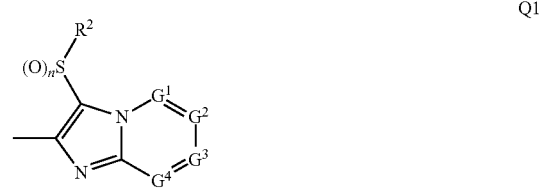

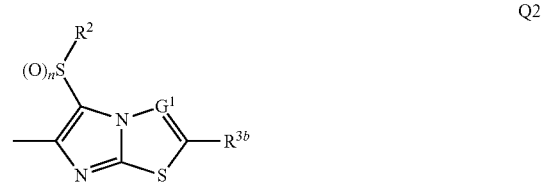

-continued

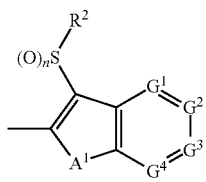
Q3

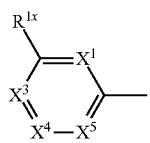
T-1

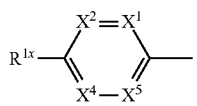
T-2 n represents 0, 1, or 2, $G^1$ represents a nitrogen atom or $CR^{3a}$, $G^2$ represents a nitrogen atom or $CR^{3b}$, $G^3$ represents a nitrogen atom or $CR^{3c}$, $G^4$ represents a nitrogen atom or $CR^{3d}$, $R^{3a}$, $R^{3b}$, $R^{3c}$, and $R^{3d}$ each independently represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a 5- or 6-membered aromatic heterocyclic group optionally having one or more substituents selected from Group H, $OR^{12x}$, $NR^{11}R^{12}$, $NR^{11a}R^{12a}$, $NR^{29}NR^{11}R^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15x}R^{16x}$, $NR^{24}NR^{11}C(O)NR^{15x}R^{16x}$, $N=CHNR^{15x}R^{16x}$, $N=S(O)_xR^{15}R^{16}$, $C(O)OR^{17}$, $C(O)R^{13}$, $C(O)NR^{15x}R^{16x}$, $C(O)NR^{11}S(O)_2R^{23}$, $CR^{30}=NOR^{17}$, $NR^{11}CR^{24}=NOR^{17}$, a cyano group, a nitro group, a hydrogen atom, or a halogen atom, x represents 0 or 1, $A^1$ represents $NR^5$, an oxygen atom, or a sulfur atom, $A^2$ represents a nitrogen atom or $CR^{4a}$, $A^3$ represents a nitrogen atom or $CR^{4b}$, $A^4$ represents a nitrogen atom or $CR^{4c}$, $R^{4a}$, $R^{4b}$, and $R^{4c}$ each independently represents a hydrogen atom, a C1-C6 chain hydrocarbon group optionally having one or more halogen atoms, a nitro group, $OR^{18}$, $NR^{18}R^{19}$, a cyano group, or a halogen atom, T represents a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by Formula T-1, a group represented by Formula T-2, a group represented by Formula T-3, a group represented by Formula T-4, a group represented by Formula T-5, a group represented by Formula T-6, a group represented by Formula T-7, a group represented by Formula T-8, a group represented by Formula T-9, a group represented by Formula T-10, a group represented by Formula T-11, or a group represented by Formula T-12,

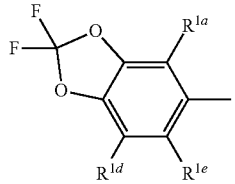
T-3

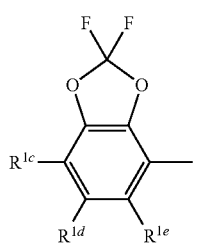
T-4

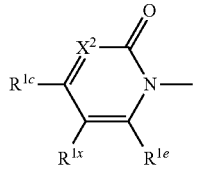
T-5

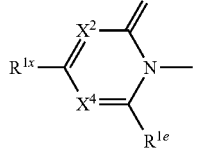
T-6

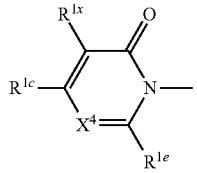
T-7

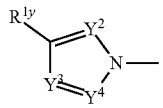
T-8

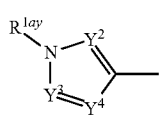
T-9

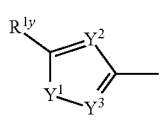
T-10

-continued

T-11

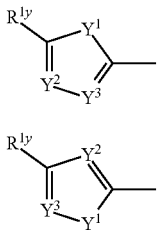

T-12

X$^1$ represents a nitrogen atom or CR$^{1a}$,
X$^2$ represents a nitrogen atom or CR$^{1b}$,
X$^3$ represents a nitrogen atom or CR$^{1c}$,
X$^4$ represents a nitrogen atom or CR$^{1d}$,
X$^5$ represents a nitrogen atom or CR$^{1e}$,
R$^{1x}$ represents OR$^7$, OS(O)$_2$R$^7$, S(O)$_m$R$^7$, NR$^1$R$^{29}$, NR$^8$S(O)$_2$R$^7$, a C1-C5 chain hydrocarbon group having one or more halogen atoms, or a halogen atom,
R$^{1a}$, R$^{1b}$, R$^{1c}$, R$^{1d}$, and R$^{1e}$ each independently represents a hydrogen atom, a C1-C6 chain hydrocarbon group optionally having one or more halogen atoms, a C3-C6 cycloalkyl group optionally having one or more halogen atoms, or a halogen atom,
Y$^1$ represents NR$^{25}$, an oxygen atom, or a sulfur atom,
Y$^2$ represents a nitrogen atom or CR$^{26}$,
Y$^3$ represents a nitrogen atom or CR$^{27}$,
Y$^4$ represents a nitrogen atom or CR$^{28}$,
R$^5$ and R$^{25}$ each independently represents a hydrogen atom, a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl) C1-C6 alkyl group optionally having one or more halogen atoms,
R$^{26}$, R$^{27}$, and R$^{28}$ each independently represents a hydrogen atom, a C1-C6 chain hydrocarbon group optionally having one or more halogen atoms, a C3-C6 cycloalkyl group optionally having one or more halogen atoms, or a halogen atom,
R$^{1y}$ represents OR$^7$, OS(O)$_2$R$^7$, S(O)$_m$R$^7$, NR$^8$S(O)$_2$R$^7$, a cyano group, a C1-C5 chain hydrocarbon group having one or more halogen atoms, or a halogen atom,
R$^{1ay}$ and R$^7$ each independently represents a C1-C6 chain hydrocarbon group having one or more halogen atoms,
R$^8$ represents a hydrogen atom, or a C1-C6 chain hydrocarbon group optionally having one or more halogen atoms,
m represents 0, 1, or 2,
R$^1$ represents a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-05 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, or a C3-C7 cycloalkyl group having one or more substituents selected from Group G,
R$^2$ represents a cyclopropyl group, a cyclopropylmethyl group, or a C1-C6 alkyl group optionally having one or more halogen atoms,
R$^{11}$, R$^{17}$, R$^{19}$, R$^{24}$, and R$^{29}$ each independently represents a hydrogen atom, or a C1-C6 chain hydrocarbon group optionally having one or more halogen atoms,
R$^{30}$ represents a hydrogen atom, a halogen atom, OR$^{31}$, NR$^{32}$R$^{33}$, or a C1-C6 chain hydrocarbon group optionally having one or more halogen atoms,
R$^{18}$ and R$^{31}$ each independently represents a C1-C6 chain hydrocarbon group optionally having one or more halogen atoms,
R$^{32}$ and R$^{33}$ each independently represents a hydrogen atom, or a C1-C6 chain hydrocarbon group optionally having one or more halogen atoms,
R$^{12}$ represents a hydrogen atom, S(O)$_2$R$^{23}$, a C1-C6 chain hydrocarbon group optionally having one or more halogen atoms, or a C1-C6 alkyl group having one substituent selected from Group F,
R$^{12x}$ represents a C1-C6 chain hydrocarbon group optionally having one or more halogen atoms, a C1-C6 alkyl group having one substituent selected from Group F, a C3-C7 cycloalkyl group optionally having one or more substituents selected from Group J, a C3-C7 cycloalkenyl group optionally having one or more substituents selected from Group J, a phenyl group, a 6-membered aromatic heterocyclic group, in which the phenyl group and the 6-membered aromatic heterocyclic group each independently optionally has one or more substituents selected from Group D,
S(O)$_2$R$^{23}$, or a hydrogen atom,
R$^{23}$ represents a C1-C6 chain hydrocarbon group optionally having one or more halogen atoms, or a phenyl group optionally having one or more substituents selected from Group D,
R$^{11a}$ and R$^{12a}$, together with the nitrogen atom to which R$^{11a}$ and R$^{12a}$ are bonded, represent a 3- to 7-membered non-aromatic heterocyclic group optionally having one or more substituents selected from Group E,
R$^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, a phenyl group optionally having one or more substituents selected from Group D, or a 5- or 6-membered aromatic heterocyclic group optionally having one or more substituents selected from Group D,
R$^{14}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl C1-C3 alkyl group, in which the phenyl moiety in the phenyl C1-C3 alkyl group optionally has one or more substituents selected from Group D,
R$^{15}$ and R$^{16}$ each independently represents a C1-C6 alkyl group optionally having one or more halogen atoms,
R$^{15x}$ represents a C1-C6 alkyl group optionally having one or more halogen atoms, or a hydrogen atom,
R$^{16x}$ represents a C1-C6 chain hydrocarbon group optionally having one or more substituents selected from Group F, a C3-C7 cycloalkyl group optionally having one or more substituents selected from Group J, or a hydrogen atom,
Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom, Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, in which $R^{21}$ and $R^{22}$ each independently represents a C1-C6 alkyl group optionally having one or more halogen atoms, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group, Group F: a group consisting of a C1-C6 alkoxy group optionally having one or more halogen atoms, an amino group, $NHR^{21}$, $NR^{21}R^{22}$, a cyano group, a phenyl group optionally having one or more substituents selected from Group D, a 5- or 6-membered aromatic heterocyclic group optionally having one or more substituents selected from Group D, a C3-C7 cycloalkyl group optionally having one or more halogen atoms, and a 3- to 7-membered non-aromatic heterocyclic group optionally having one or more substituents selected from Group C, Group G: a group consisting of a halogen atom and a C1-C6 haloalkyl group, Group H: a group consisting of a halogen atom, a nitro group, a cyano group, an amino group, a 5- or 6-membered aromatic heterocyclic group, a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, and $C(O)OR^{10}$, Group J: a group consisting of a C1-C6 alkyl group optionally having one or more halogen atoms, a halogen atom, and a cyano group, $R^9$ represents a C1-C6 alkyl group optionally having one or more halogen atoms, or a C3-C6 cycloalkyl group optionally having one or more halogen atoms, and $R^{10}$ represents a hydrogen atom, a C1-C6 alkyl group optionally having one or more halogen atoms, or a C3-C6 cycloalkyl group optionally having one or more halogen atoms.

2. The compound according to claim 1, which is represented by Formula (I):

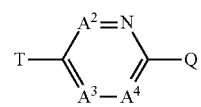

(I)

in the formula,

Q is a group represented by Formula Q1, a group represented by Formula Q2, or a group represented by Formula Q3,

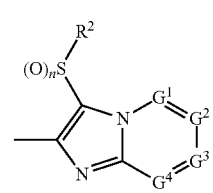

Q1

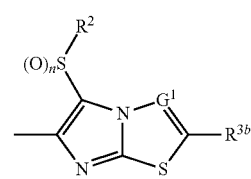

Q2

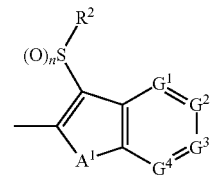

Q3 n is 0, 1, or 2, $G^1$ is a nitrogen atom or $CR^{3a}$,
$G^2$ is a nitrogen atom or $CR^{3b}$,
$G^3$ is a nitrogen atom or $CR^{3c}$,
$G^4$ is a nitrogen atom or $CR^{3d}$, $R^{3a}$, $R^{3b}$, $R^{3c}$, and $R^{3d}$ are each independently a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a 5- or 6-membered aromatic heterocyclic group optionally having one or more substituents selected from Group H, $OR^{12}$, $NR^{11}R^{12}$, $NR^{11a}R^{12a}$, $NR^{29}NR^{11}R^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15}R^{16}$, $NR^{24}NR^{11}C(O)NR^{15}R^{16}$, $N=CHNR^{15}R^{16}$, $N=S(O)_xR^{15}R^{16}$, $C(O)OR^{17}$, a cyano group, a nitro group, a hydrogen atom, or a halogen atom, x is 0 or 1, $A^1$ is $NR^5$, an oxygen atom, or a sulfur atom,
$A^2$ is a nitrogen atom or $CR^{4a}$,
$A^3$ is a nitrogen atom or $CR^{4b}$,
$A^4$ is a nitrogen atom or $CR^{4c}$, $R^{4a}$, $R^{4b}$, and $R^{4c}$ are each independently a hydrogen atom, a C1-C6 chain hydrocarbon group optionally having one or more halogen atoms, a nitro group, $OR^{18}$, $NR^{18}R^{19}$, a cyano group, or a halogen atom, T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, OR$^1$, S(O)$_m$R$^1$, OS(O)$_2$R$^1$, CH$_2$OR$^1$, NR$^1$R$^{29}$, C(O)R$^1$, C(O)NR$^1$R$^{29}$, NR$^{29}$C(O)R$^1$, N=CR$^1$R$^{30}$, a group represented by Formula T-1, a group represented by Formula T-2, a group represented by Formula T-3, a group represented by Formula T-4, a group represented by Formula T-5, a group represented by Formula T-6, a group represented by Formula T-7, a group represented by Formula T-8, a group represented by Formula T-9, a group represented by Formula T-10, a group represented by Formula T-11, or a group represented by Formula T-12,

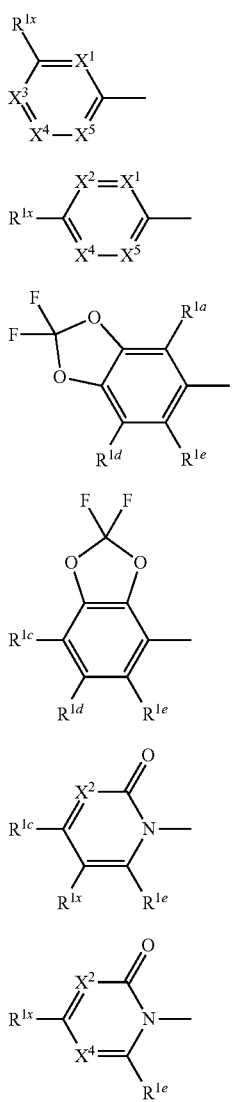

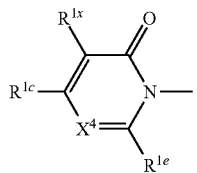

T-7

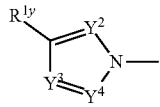

T-8

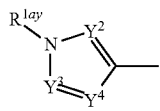

T-9

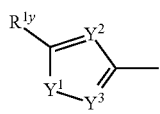

T-10

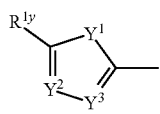

T-11

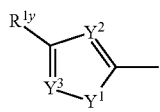

T-12

$X^1$ is a nitrogen atom or CR$^{1a}$,
$X^2$ is a nitrogen atom or CR$^{1b}$,
$X^3$ is a nitrogen atom or CR$^{1c}$,
$X^4$ is a nitrogen atom or CR$^{1d}$,
$X^5$ is a nitrogen atom or CR$^{1e}$,
R$^{1x}$ is OR$^7$, OS(O)$_2$R$^7$, S(O)$_m$R$^7$, NR$^1$R$^{29}$, NR$^8$S(O)$_2$R$^7$, a C1-C5 chain hydrocarbon group having one or more halogen atoms, or a halogen atom,
R$^{1a}$, R$^{1b}$, R$^{1c}$, R$^{1d}$, and R$^{1e}$ are each independently a hydrogen atom, a C1-C6 chain hydrocarbon group optionally having one or more halogen atoms, a C3-C6 cycloalkyl group optionally having one or more halogen atoms, or a halogen atom,
Y$^1$ is NR$^{25}$, an oxygen atom, or a sulfur atom,
Y$^2$ is a nitrogen atom or CR$^{26}$,
Y$^3$ is a nitrogen atom or CR$^{27}$,
Y$^4$ is a nitrogen atom or CR$^{28}$,
R$^5$ and R$^{25}$ are each independently a hydrogen atom, a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl) C1-C6 alkyl group optionally having one or more halogen atoms,
R$^{26}$, R$^{27}$, and R$^{28}$ are each independently a hydrogen atom, a C1-C6 chain hydrocarbon group optionally having one or more halogen atoms, a C3-C6 cycloalkyl group optionally having one or more halogen atoms, or a halogen atom,
R$^{1y}$ is OR$^7$, OS(O)$_2$R$^7$, S(O)$_m$R$^7$, NR$^8$S(O)$_2$R$^7$, a cyano group, a C1-C5 chain hydrocarbon group having one or more halogen atoms, or a halogen atom, $R^{1ay}$ and $R^7$ are each independently a C1-C6 chain hydrocarbon group having one or more halogen atoms, $R^8$ is a hydrogen atom, or a C1-C6 chain hydrocarbon group optionally having one or more halogen atoms, m is 0, 1, or 2, $R^1$ is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, or a C3-C7 cycloalkyl group having one or more substituents selected from Group G, $R^2$ is a cyclopropyl group, a cyclopropylmethyl group, or a C1-C6 alkyl group optionally having one or more halogen atoms, $R^{11}$, $R^{17}$, $R^{19}$, $R^{24}$, and $R^{29}$ are each independently a hydrogen atom, or a C1-C6 chain hydrocarbon group optionally having one or more halogen atoms, $R^{30}$ is a hydrogen atom, a halogen atom, $OR^{31}$, $NR^{32}R^{33}$, or a C1-C6 chain hydrocarbon group optionally having one or more halogen atoms, $R^{18}$ and $R^{31}$ are each independently a C1-C6 chain hydrocarbon group optionally having one or more halogen atoms, $R^{32}$ and $R^{33}$ are each independently a hydrogen atom or a C1-C6 chain hydrocarbon group optionally having one or more halogen atoms, $R^{12}$ is a hydrogen atom, $S(O)_2R^{23}$, a C1-C6 chain hydrocarbon group optionally having one or more halogen atoms, or a C1-C6 alkyl group having one substituent selected from Group F, $R^{23}$ is a C1-C6 chain hydrocarbon group optionally having one or more halogen atoms, or a phenyl group optionally having one or more substituents selected from Group D, $R^{11a}$ and $R^{12a}$, together with the nitrogen atom to which $R^{11a}$ and $R^{12a}$ are bonded, are a 3-to 7-membered non-aromatic heterocyclic group optionally having one or more substituents selected from Group E, $R^{13}$ is a hydrogen atom, a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, a phenyl group optionally having one or more substituents selected from Group D, or a 5- or 6-membered aromatic heterocyclic group optionally having one or more substituents selected from Group D, $R^{14}$ is a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl C1-C3 alkyl group, in which the phenyl moiety in the phenyl C1-C3 alkyl group optionally has one or more substituents selected from Group D, $R^{15}$ and $R^{16}$ are each independently a C1-C6 alkyl group optionally having one or more halogen atoms, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom, Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, in which $R^{21}$ and $R^{22}$ each independently represents a C1-C6 alkyl group optionally having one or more halogen atoms, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group, Group F: a group consisting of a C1-C6 alkoxy group optionally having one or more halogen atoms, an amino group, $NHR^{21}$, $NR^{21}R^{22}$, a cyano group, a phenyl group optionally having one or more substituents selected from Group D, a 5- or 6-membered aromatic heterocyclic group optionally having one or more substituents selected from Group D, a C3-C7 cycloalkyl group optionally having one or more halogen atoms, and a 3- to 7-membered non-aromatic heterocyclic group optionally having one or more substituents selected from Group C, Group G: a group consisting of a halogen atom and a C1-C6 haloalkyl group, Group H: a group consisting of a halogen atom, a nitro group, a cyano group, an amino group, a 5- or 6-membered aromatic heterocyclic group, a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, and $C(O)OR^{10}$, $R^9$ is a C1-C6 alkyl group optionally having one or more halogen atoms, or a C3-C6 cycloalkyl group optionally having one or more halogen atoms, and $R^{10}$ is a hydrogen atom, a C1-C6 alkyl group optionally having one or more halogen atoms, or a C3-C6 cycloalkyl group optionally having one or more halogen atoms.

3. The compound according to claim 1,
wherein Q is a group represented by Formula Q1.

4. The compound according to claim 1,
wherein $A^2$ is $CR^{4a}$ and $A^4$ is $CR^{4c}$.

5. The compound according to claim 1,
wherein $A^2$ is $CR^{4a}$, $A^3$ is $CR^{4b}$, and $A^4$ is $CR^{4c}$.

6. The compound according to claim 1,
wherein $A^2$ is $CR^{4a}$, $A^3$ is a nitrogen atom, and $A^4$ is $CR^{4c}$.

7. The compound according to claim 1,
wherein T is a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{29}$.

8. The compound according to claim 1,
wherein T is $OR^1$, and $R^1$ is a C1-C5 alkyl group having three or more fluorine atoms.

9. The compound according to claim 1,
wherein $R^{3a}$, $R^{3b}$, $R^{3c}$, and $R^{3d}$ are each independently a C1-C6 alkyl group optionally having one or more halogen atoms, a phenyl group, a pyridyl group, a pyrimidinyl group, a pyrazolyl group, a triazolyl group, in which the phenyl group, the pyridyl group, the pyrimidinyl group, the pyrazolyl group, and the triazolyl group each independently optionally has one or more substituents selected from Group H, an amino group, $NR^{11}C(O)OR^{14}$, a hydrogen atom, or a halogen atom, and $R^{4a}$ and $R^{4c}$ are hydrogen atoms.

10. The compound according to claim 1,
wherein $G^1$ and $G^4$ are CH's, $G^2$ is $CR^{3b}$, $G^3$ is $CR^{3c}$, $R^{3b}$ and $R^{3c}$ are each independently a C1-C6 alkyl group optionally having one or more halogen atoms, or a hydrogen atom, and $R^{4a}$ and $R^{4c}$ are hydrogen atoms.

11. The compound according to claim 1,
wherein $R^2$ is an ethyl group.

12. A harmful-arthropod-controlling composition, comprising:
the compound according to claim 1; and
an inactive carrier.

13. A method for controlling a harmful arthropod, comprising:
applying an effective amount of the compound according to claim 1 to the harmful arthropod or a habitat of the harmful arthropod.

14. A composition comprising:
one or more ingredients selected from the group consisting of Group (a), Group (b), Group (c), and Group (d); and
the compound according to claim 1,
Group (a): a group consisting of insecticidal active ingredients, acaricidal active ingredients, and nematicidal active ingredients,
Group (b): fungicidal active ingredients,
Group (c): plant growth-regulating ingredients and
Group (d): phytotoxicity-decreasing ingredients.

* * * * *